(12) United States Patent
Hong et al.

(10) Patent No.: US 6,500,846 B1
(45) Date of Patent: Dec. 31, 2002

(54) CDK INHIBITORS HAVING FLAVONE STRUCTURE

(75) Inventors: Chang Yong Hong, Daejeon (KR); Tae Sik Park, Daejeon (KR); Young Kwan Kim, Daejeon (KR); Jin Ho Lee, Daejeon (KR); Jong Hyun Kim, Daejeon (KR); Dong Myung Kim, Daejeon (KR); Ho Sun Son, Daejeon (KR); Sang Woong Kim, Daejeon (KR); Eunice Eun Kyeong Kim, Daejeon (KR)

(73) Assignee: LG Chemical, Ltd., Seuol (KR)

( * ) Notice: Subject to any disclaimer, the term of this patent is extended or adjusted under 35 U.S.C. 154(b) by 0 days.

(21) Appl. No.: 09/786,227

(22) PCT Filed: Aug. 31, 1999

(86) PCT No.: PCT/KR99/00499

§ 371 (c)(1),
(2), (4) Date: Mar. 1, 2001

(87) PCT Pub. No.: WO00/12496

PCT Pub. Date: Mar. 9, 2000

(30) Foreign Application Priority Data

Sep. 1, 1998 (KR) ............................................. 98/35837
Apr. 9, 1999 (KR) ............................................. 99/12523
Apr. 15, 1999 (KR) ............................................. 99/13225

(51) Int. Cl.$^7$ .................... A61K 31/352; C07D 311/30; A61P 43/00
(52) U.S. Cl. ....................... 514/321; 514/452; 514/457; 546/197; 549/285; 549/288
(58) Field of Search .......................... 546/197; 549/285, 549/288; 514/321, 452, 457

(56) References Cited

FOREIGN PATENT DOCUMENTS

JP         05178745         *     7/1993

* cited by examiner

*Primary Examiner*—Joseph K. McKane
*Assistant Examiner*—Andrea D Small
(74) *Attorney, Agent, or Firm*—Peter F. Corless; John B. Alexander; Edwards & Angell, LLP

(57) ABSTRACT

The present invention relates to a novel flavone derivative, pharmaceutically acceptable salt, hydrate, solvate and isomer thereof which is useful as an inhibitor against Cyclin Dependent Kinase (CDK), a process for preparation thereof, and a composition of anti-cancer agent or agent for treating neurodegenerative disease comprising this compound as an active ingredient.

7 Claims, No Drawings

CDK INHIBITORS HAVING FLAVONE STRUCTURE

This application is a 371 of PCT/KR99/00499 Aug. 31, 1999.

TECHNICAL FIELD

The present invention relates to a novel flavone derivative represented by the following formula (1):

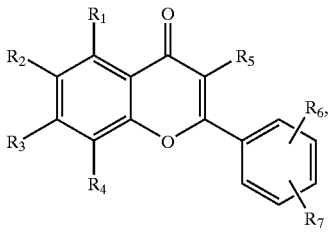

(1)

in which

R$_1$, R$_3$ and R$_4$ each independently represent hydrogen, halogen, hydroxy, alkyl, lower alkoxy, amino or nitro, R$_2$ represents hydrogen, halogen, hydroxy, lower alkyl, lower alkoxy, amino, nitro or

wherein

A represents amino which may be optionally substituted with alkyl, cycloalkyl, aralkyl, acyl, or aryl which is optionally substituted with one or two substituents selected from the group consisting of halogen, cyano, nitro and amino; or 1,2,3,4-tetrahydroisoquinoline which may be optionally substituted with halogenoalkylcarbonyl; or alkyl, aryl, aralkyl or heteroaryl each of which may be optionally substituted with one or two substituents selected from the group consisting of alkyl, halogenoalkyl, halogen, dialkylamino, phenyl, nitro, amino, isooxazole, pyridine, carboxy, morpholine, methylpiperazine and cyano, Y represents SO$_2$ or CO, B represents hydrogen or alkyl, R$_5$ represents hydrogen or hydroxy, and R$_6$ and R$_7$ are substituted at o-, m- or p-position from each other and each independently represents hydrogen, hydroxy, halogen or lower alkoxy or together represent lower alkylenedioxy, pharmaceutically acceptable salt, hydrate, solvate and isomer thereof which is useful as an inhibitor for Cyclin Dependent Kinase (hereinafter, referred to as "CDK"), In addition, the present invention relates to a process for preparing the flavone derivative of formula (1) and also relates to an anti-cancer agent or an agent for treating neurodegenerative disease characterized by comprising the compound of formula (1) as an active ingredient.

BACKGROUND ART

Researches on cell division process in molecular level have been extensively performed from the late 1980's through study of division of frog oocytes, analysis several yeast cell growth or characterization of induced mutants by radiation and study of the tumor suppressor Rb. In the 1990's, it is discovered that small molecular cell growth regulator controls cell division process (i.e. growth, differentiation, cytogenesis, aging and apoptosis etc.) through its own regulatory function. These results were very useful for more precise understanding of the pathology of several diseases.

A representative example is cancer. In transformation process from normal cells to cancer cells, it was frequently observed that cell growth regulator loses its own function. That is to say, in cancer cells, the cell growth regulator shows an abnormal activity, which is deeply associated with invasion/metastasis which is crucial in the cancerpathology. Particularly, cell cycle deregulation is recognized to be a direct cause of cancer since cancer occurs in experimental animal when overexpression or knock-out of cell growth regulator is induced by using tranformed animal.

The cell growth is under positive or negative regulation in the same manner as other biological regulations. The major pathway of cell cycle regulation known up to now is based on CDK activity and as a result of studies on many cancer cells and carcinogenesis mechanisms, it was confirmed that problems of positive or negative regulation on CDK activity result in carcinogenesis in many cases. That is, cancer may occur when positive or negative regulation and timely regulation which is important for cell growth regulation are disrupted.

The representative CDKs of mammals are CDK4 (Cyclin dependent kinase 4) which shows its activity in mid-G1 phase of cell cycle, CDK2 which shows its activity in mid-1 and S phases, CDC2 (CDK1) which shows its activity in G2-M phase, and so on. It is known that CDK4 and CDK2 activities are regulated by check point of G1-S cell cycle and CDC2 activity by check point of G2-M. In many cancer cells, abnormalities appear in the regulatory mechanism of CDK4, CDK2 and CDC2 (CDK 1) and in fact, it was confirmed that induced abnormalities cause cancer in the transformed animal. Therefore, CDK4, CDK2 and CDC2 (CDK1) among several kinds of CDKs are suitable as a target of anti-cancer agents.

The results of studies on relation between these CDKs and carcinogtenesis will be explained in more detail in the following.

The relation between the abnormal regulation of CDK4 activity and carcinogenesis is observed in several cancer tissues. The deletion of p16 and p15 genes in several kinds of cancer is reported and particularly, overexpression of cyclin D1 is observed, which has close relation with the fact that breast cancer has a metastatic proper and which suggests that malignant phenotype may be expressed when CDK4 activity is deregulated.

Furthermore, it was reported that p16 knocked-out mouse has such a high carcinogenesis rate as p53 knocked-out mouse, which suggests that malfunction of p16 on CDK4 regulation is a cause of carcinogenesis. It gives the possibility that p16 plays a role in the downstream in NIH 3T3 cell with overexpressed ras or src. Reversely it was observed that modified phenotype wherein p16 or p21 is transformed with ras is repaired into wild phenotype. From these experimental results, deregulation of CDK4 activity may be a cause of carcinogenesis and play a role in maintenance of phenotype of cancer cell. Therefore, CDK4 inhibitors may have anti-cancer effects.

It was reported that overexpression of cyclin E is observed in some breast cancers, deeply associated with metastasis of breast cancer, inhibits cell apoptosis under low serum condition and induces anchorage independent growth, and that hyperproliferation (neoplasia) of mammary epithelial cells is observed in transformed animal with overexpressed CDK2 by MMTV promoter, which suggests that CDK2 activity is related with the progress or maintenance of cell transformation and CDK2 inhibitors may also have anti-cancer effects.

It is recently discovered that CDK5 among these CDKs may cause neurodegenerative diseases by phosphorylation of tau protein of the brain. Therefore, CDK5 inhibitor may be useful as an agent for treating neurodegenerative diseases (e.g. Alzheimer's disease). CDK2 inhibitors may have inhibitory effects on CDK5 in that CDK2 and CDK5 are homologous in the same family (Ref.: John Leu et al., "Neuronal CDC2-like kinase", TIBS, January 1995, pp33~37).

Furthermore, it is discovered that CDC2 (CDK1), CDK3, CDK6 and CDK7 play an important role in each phase of cell division. These are classified into CDKs family. In addition, to cyclin D1 and E, cyclin A, B, C, D2, D3, D4, F and G are also calssified into the same family.

On the basis of the above-mentioned research, efficient inhibitors of these CDKs may be useful as anti-cancer or anti-neurodegenerative agents. Therefore, recently, these inhibitors have been developed.

As effective CDK inhibitors developed hitherto, there exists Flavopiridol, compound of the formula (2)

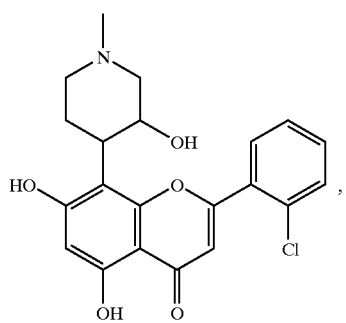

(2)

which is under clincal trials [Ref.: EP 0,241,003 and 0,336, 061]. In addition, a purine derivative of the formula (3)

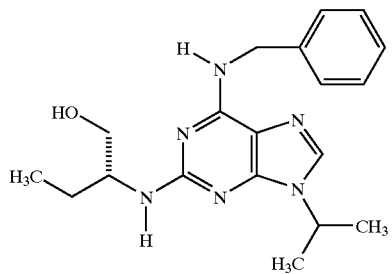

(3)

has been recently developed [Ref: WO 97/16447].

However, the CDK inhibitors developed up to now could not have satisfactory effects.

So, the present inventors have made widespread and concentrative researches on CDK inhibitors and as a result, found that the above flavone derivative of formula (1) which has a quite different structure from any other known CDK inhibitors inhibits CDKs effectively and finally. complete the present invention.

DISCLOSURE OF THE INVENTION

The object of the present invention is to provide a novel flavone derivative of formula (1), pharmaceutically acceptable salt, hydrate, solvate and isomer thereof having an inhibitory activity for CDK.

Another object of the present invention is to provide a process for preparing the compound of formula (1). Still another object of the present invention is to provide an anti-cancer agent and an agent for treating neurodegenerative disease each of which is characterized by comprising as an active ingredient the compound of formula (1) with a pharmaceutically acceptable carrier.

In this specification, CDKs includes all of CDK2, CDK4, CDC2 (CDK1), CDK3, CDK5, CDK6, CDK7 etc., and cyclin includes cyclin D1, E, A, B, C, D2, D3, D4, F, and G.

DETAILED DESCRIPTION OF THE INVENTION

The present invention is explained in detail hereinafter.

The present invention relates to a novel flavone derivative represented by the following formula (1):

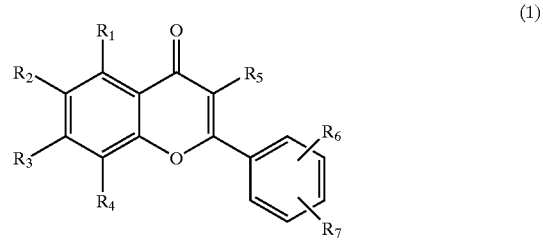

(1)

in which $R_1$, $R_3$ and $R_4$ each independently represent hydrogen, halogen. hydroxy, alkyl, lower alkoxy, amino or nitro.

$R_2$ represents hydrogen, halogen, hydroxy, lower alkyl, lower alkoxy, amino, nitro or

wherein

A represents amino which may be optionally substituted with alkyl, cycloalkyl, aralkyl, acyl, or aryl which is optionally substituted with one or two substituents selected from the group consisting of halogen, cyano, nitro and amino; or 1,2,3,4-tetrahydroisoquinoline which may be optionally substituted with halogenoalkylcarbonyl; or alkyl, aryl, aralkyl or heteroaryl each of which may be optionally substituted with one or two substituents selected from the group consisting of alkyl, halogenoalkyl, halogen, dialkylamino, phenyl, nitro, amino, isooxazole, pyridine, carboxy, morpholine, methylpiperazine and cyano, Y represents $SO_2$ or CO, B represents hydrogen or alkyl, $R_5$ represents hydrogen or hydroxy, and $R_6$ and $R_7$ are substituted at o-, m- or p-position from each other and each independently represents hydrogen, hydroxy, halogen or lower alkoxy or together represent lower alkylenedioxy, pharmaceutically acceptable salt, hydrate, solvate and isomer thereof which has efficacies on treating cancer or neurodegenerative disease through a mechanism of inhibiting CDKs activity, In addition, the present invention relates to a process for preparing the flavone derivative of formula (1) and also relates to an anti-cancer agent or an agent for treating neurodegenerative disease each of which is characterized by comprising the compound of formula (1) as an active ingredient.

Among the compound of formula (1) according to the present invention, the preferred compounds include those wherein (1) $R_1$, $R_2$, $R_3$ and $R_4$ each independently represent hydrogen, halogen. hydroxy, lower alkoxy or nitro (provided that two or more of these four substituents are hydrogen),
$R_5$ represents hydrogen or hydroxy, and
$R_6$ and $R_7$ are substituted at o-, m- or p-position from each other and each independently represents hydrogen, hydroxy, halogen or lower alkoxy or together represent lower alkylenedioxy, or (2) $R_1$ represents hydrogen, hydroxy, lower alkoxy or amino,
$R_2$ and $R_3$ each independently represent hydrogen, halogen, hydroxy, lower alkyl, lower alkoxy or amino,
$R_4$ represents hydrogen, halogen, hydroxy or lower alkoxy,
$R_5$ represents hydroxy, and
$R_6$ and $R_7$ represent 3-hydroxy and 4-hydroxy respectively, or (3) $R_1$, $R_3$ and $R_4$ each independently represent hydrogen, halogen, hydroxy, alkyl or amino (provided that two or more of these three substituents are hydrogen),
$R_2$ represents

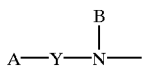

wherein
A represents amino which may be optionally substituted with alkyl, cycloalkyl, aralkyl, acyl, or amyl which is optionally substituted with one or two substituents selected from the group consisting of halogen, cyano, nitro and amino; or 1,2,3,4-tetrahydroisoquinoline which may be optionally substituted with halogenoalkylcarbonyl; or alkyl, aryl, aralkyl or heteroaryl each of which may be optionally substituted with one or two substituents selected from the group consisting of alkyl, halogenoalkyl, halogen, dialkylamino, phenyl, nitro, amino, isooxazole, pyridine, carboxy, morpholine, methylpiperazine and cyano,
Y represents $SO_2$ or CO,
B represents hydrogen or alkyl,
$R_5$ represents hydroxy, and
$R_6$ and $R_7$ represent 3-hydroxy and 4-hydroxy respectively.

More preferred compounds include those wherein
(1) $R_1$, $R_2$, $R_3$ and $R_4$ each independently represent hydrogen, chloro, hydroxy, methoxy or nitro(provided that two or more of these four substituents are hydrogen),
$R_5$ represents hydrogen or hydroxy, and
$R_6$ and $R_7$ are substituted at o-, m- or p-position from each other and each independently represents hydrogen, hydroxy, chloro or methoxy or together represent methylenedioxy, or (2) $R_1$ represents hydrogen, hydroxy or lower alkoxy,
$R_2$ represents hydrogen, halogen, hydroxy, lower alkyl, lower alkoxy or amino,
$R_3$ represents hydrogen, hydroxy, lower alkyl, lower alkoxy or amino,
$R_4$ represents hydrogen, halogen or hydroxy,
$R_5$ represents hydroxy, and
$R_6$, and $R_7$ represent 3-hydroxy and 4-hydroxy respectively, or (3) $R_1$, $R_3$ and $R_4$ each represent hydrogen,
$R_2$ represents

wherein
A represents amino which may be optionally substituted with cycloalkyl; or 1,2,3,4-tetrahydroisoquinoline which may be optionally substituted with halogenoalkylcarbonyl; or alkyl, aryl, aralkyl or heteroaryl each of which may be optionally substituted with one or two substituents selected from the group consisting of alkyl, halogenoalkyl, halogen, dialkylamino, phenyl. nitro, amino isooxazole, pyridine carboxy, morpholine and methylpiperazine,
Y represents $SO_2$,
B represents hydrogen,
$R_5$ represents hydroxy, and
$R_6$ and $R_7$ represent 3-hydroxy and 4-hydroxy respectively, or (4) $R_1$, $R_3$ and $R_4$ each represent hydrogen
$R_2$ represents

wherein
A represents amino which may be optionally substituted with cycloalkyl, aralkyl, acyl, or aryl which is optionally substituted with one or two substituents selected from the group consisting of halogen, cyano, nitro and amino; or alkyl or aryl each of which may be optionally substituted with halogen,
Y represents CO,
B represents hydrogen,
$R_5$ represents hydroxy, and
$R_6$ and $R_7$ represent 3-hydroxy and 4-hydroxy respectively.

Most preferred compounds include those wherein
(1) $R_1$ represents hydrogen, hydroxy or methoxy,
$R_2$ represents hydrogen, bromine, hydroxy, methyl or amino,
$R_3$ represents hydrogen, hydroxy, methyl, methoxy or amino,
$R_4$ represents hydrogen, halogen or hydroxy,
$R_5$ represents hydroxy, and
$R_6$ and $R_7$ represent 3-hydroxy and 4-hydroxy respectively, or (2) $R_1$, $R_3$ and $R_4$ each represent hydrogen,
$R_2$ represents

wherein
A represents 1,2,3,4-tetrahydroisoquinoline which may be optionally substituted with halogenoalkylcarbonyl or aryl or heteroaryl each of which may be optionally substituted with one or two substituents selected from the group consisting of alkyl, halogenoalkyl, halogen, dialkylamino, phenyl, nitro, amino, isooxazole, pyridine, carboxy, morpholine and methylpiperazine,
Y represents $SO_2$,
B represents hydrogen,
$R_5$ represents hydroxy, and
$R_6$ and $R_7$ represent 3-hydroxy and 4-hydroxy respectively, or (3) $R_1$, $R_3$ and $R_4$ each represent hydrogen,
$R_2$ represents

wherein
A represents amino which is substituted with aryl which is substituted with one or two substituents selected from the group consisting of halogen, cyano, nitro and amino,
Y represents CO,
B represents hydrogen,
$R_5$ represents hydroxy, and
$R_6$ and $R_7$ represent 3-hydroxy and 4-hydroxy respectively.

Typical examples of the flavone derivative of formula (1) according to the present invention are
compound 1) 2-(4-chloro-phenyl)-7-methoxy-chromen-4-one,
compound 2) 7-methoxy-2-phenyl-chromen-4-one,
compound 3) 7-hydroxy-2-phenyl-chromen-4-one.
compound 4) 2-(benzo[1,3]dioxol-5-yl)-3-hydroxy-5-methoxy-chromen-4-one,
compound 5) 2-(benzo[1,3]dioxol-5-yl)-3-hydroxy-6-methoxy-chromen-4-one,
compound 6) 2-(benzo[1,3]dioxol-5-yl)-3-hydroxy-7-methoxy-chromen-4-one,
compound 7) 3-hydroxy-7-methoxy-2-(4-methoxy-phenyl)-chromen-4-one,
compound 8) 2-(4-chloro-phenyl)-3-hydroxy-7-methoxy-chromen-4-one,
compound 9) 6-chloro-3-hydroxy-2-(4-methoxy-phenyl)-8-nitro-chromen-4-one,
compound 10) 6,8-dichloro-3-hydroxy-2-(4-methoxy-phenyl)-chromen-4-one,
compound 11) 3-hydroxy-2-(4-methoxy-phenyl)-chromen-4-one,
compound 12) 6-chloro-2-(3,4-dihydroxyphenyl)-3-hydroxy-4H-chromen-4-one,
compound 13) 6-bromo-2-(3,4-dihydroxyphenyl)-3-hydroxy-4H-chromen-4-one,
compound 14) 2-(3,4-dihydroxyphenyl)-3,6-dihydroxy-4H-chromen-4-one,
compound 15) 6-amino-2-(3,4-dihydroxyphenyl)-3-hydroxy-4H-chromen-4-one,
compound 16) 2-(3,4-dihydroxyphenyl)-3-hydroxy-6-methoxy-4H-chromen-4-one,
compound 17) 6-fluoro-2-(3,4-dihydroxyphenyl)-3-hydroxy-4H-chromen-4-one,
compound 18) 6-methyl-2-(3,4-dihydroxyphenyl)-3-hydroxy-4H-chromen-4-one,
compound 19) 6,8-dichloro-2-(3,4-dihydroxyphenyl)-3-hydroxy-4H-chromen-4-one,
compound 20) 6,8-dibromo-2-(3,4-dihydoxyphenyl)-3-hydroxy-4H-chromen-4-one,
compound 21) 6,8-difluoro-2-(3,4-dihydroxyphenyl)-3-hydroxy-4H-chromen-4-one,
compound 22) 6-chloro-2-(3,4-dihydroxyphenyl)-3-hydroxy-7-methyl-4H-chromen4-one,
compound 23) 2-(3,4-dihydroxyphenyl)-3-hydroxy-7-methoxy4H-chromen-4-one,
compound 24) 2-(3,4-dihydroxyphenyl)-3,8-dihydroxy-7-methoxy-4H-chromen-4-one,
compound 25) 2-(3,4-dihydroxyphenyl)-3,8-dihydroxy-4H-chromen-4-one,
compound 26) 2-(3,4-dihydroxyphenyl)-6,7-dimethyl-3-hydroxy-4H-chromen-4-one,
compound 27) 2-(3,4-dihydroxyphenyl)-3-hydroxy-5-methoxy-4H-chromen-4-one,
compound 28) N-[2-(3,4-dihydroxyphenyl)-3-hydroxy-4-oxo-4H-chromen-6-yl]-4-methylbenzenesulfonamide,
compound 29) 4-bromo-N-[2-(3,4-dihydroxyphenyl)-3-hydroxy-4-oxo-4H-chromen-6-yl]benzenesulfonamide,
compound 30) 3-bromo-N-[2-(3,4-dihydroxyphenyl)-3-hydroxy-4-oxo-4H-chromen-6-yl]benzenesulfonamide,
compound 31) N-[2-(3,4-dihydroxyphenyl)-3-hydroxy-4-oxo-4H-chromen-6-yl]-2-naphthalenesulfonamide,
compound 32) N-[2-(3,4-dihydroxyphenyl)-3-hydroxy-4-oxo-4H-chromen-6-yl]-5-(dimethylamino)-1-naphthalenesulfonamide,
compound 33) N-[2-(3,4-dihydroxyphenyl)-3-hydroxy-4-oxo-4H-chromen-6-yl]-2-(1-naphthyl)-1-ethanesulfonamide,
compound 34) 4,5-dibromo-N-[2-(3,4-dihydroxyphenyl)-3-hydroxy-4-oxo-41-1-chromen-6-yl]-2-thiophenesulfonamide,
compound 35) N-[2-(3,4-dihydroxyphenyl)-3-hydroxy-4-oxo-4H-chromen-6-yl]-[1,1'-diphenyl]-4-sulfonamide,
compound 36) N-[2-(3,4-dihydroxyphenyl)-3-hydroxy-4-oxo-4H-chromen-6-yl]-5-(isooxazolyl)-2-thiophenesulfonamide,
compound 37) N-[2-(3,4-dihydroxyphenyl)-3-hydroxy-4-oxo-4H-chromen-6-yl]-5-(2-pyridinyl)-2-thiophenesulfonamide,
compound 38) N-[2-(3,4-dihydroxyphenyl)-3-hydroxy-4-oxo-4H-chromen-6-yl]-3,4-difluorobenzenesulfonamide,
compound 39) N-[2-(3,4-dihydroxyphenyl)-3-hydroxy-4-oxo-4H-chromen-6-yl]-4-(trifluoromethyl)benzenesulfonamide,
compound 40) 4-chloro-N-[2-(3,4-dihydroxyphenyl)-3-hydroxy-4-oxo-4H-chromen-6-yl]-3-nitrobenzenesulfonamide, compound 41) 3-chloro-N-[2-(3,4-dihydroxyphenyl)-3-hydroxy-4-oxo-4H-chromen-6-yl]-1-propanesulfonamide, compound 42) N-[2-(3,4-dihydroxyphenyl)-3-hydroxy-4-oxo-4H-chromen-6-yl]-2,4-difluorobenzenesulfonamide, compound 43) N-[2-(3,4-dihydroxyphenyl)-3-hydroxy-4-oxo-4H-chromen-6-yl]-4-fluorobenzenesulfonamide, compound 44) N-[2-(3,4-dihydroxyphenyl)-3-hydroxy-4-oxo-4H-chromen-6-yl]-2-(2,2,2-trifluoroacetyl)-1,2,3,4-tetrahydro-7-isoquinolinesulfonamide, compound 45) 4-({[2-(3,4-dihydroxyphenyl)-3-hydroxy-4-oxo-4H-chromen-6-yl]amino}sulfonyl)benzoic acid, compound 46) N-[2-(3,4-dihydroxyphenyl)-3-hydroxy-4-oxo-4H-chromen-6-yl]-1,2,3,4-tetrahydro-7-isoquinolinesulfonamide, compound 47) N-cyclohexyl-N'-[2-(3,4-dihydroxyphenyl)-3-hydroxy-4-oxo-4H-chromen-6-yl]-sulfide, compound 48) N-[2-(3,4-dihydroxyphenyl)-3-hydroxy-4-oxo-4H-chromen-6-yl]-4-(4-morpholinyl)-3-nitrobenzenesulfonamide, compound 49) N-[2-(3,4-dihydroxyphenyl)-3-hydroxy-4-oxo-4H-chromen-6-yl]-4-(4-methyl-1-piperazinyl)-3-nitrobenzenesulfonamide, compound 50) 3-amino-N-[2-(3,4-dihydroxyphenyl)-3-hydroxy-4-oxo-4H-chromen-6-yl]-4-(4-methyl-1-piperazinyl)benzenesulfonamide, compound 51) N-[2-(3,4-dihydroxyphenyl)-3-hydroxy-4-oxo-4H-chromen-6-yl]acetamide, compound 52) N-[2-(3,4-dihydroxyphenyl)-3-hydroxy-4-oxo-4H-chromen-6-yl]benzamide, compound 53) 4-chloro-N-[2-(3,4-dihydroxyphenyl)-3-hydroxy-4-oxo-4H-chromen-6-yl]benzamide, compound 54) N-benzyl-N'-[2-(3,4-dihydroxyphenyl)-3-hydroxy-4-oxo-4H-chromen-6-yl]urea, compound 55) N-(4-bromophenyl)-N'-[2-(3,4-dihydroxyphenyl)-3-hydroxy-4-oxo-4H-chromen-6-yl]urea, compound 56) N-[2-(3,4-dihydroxyphenyl)-3-hydroxy-4-oxo-4H-chromen-6-yl]-N'-phenylurea, compound 57) N-benzoyl-N'-[2-(3,4-dihydroxyphenyl)-3-hydroxy-4-oxo-4H-chromen-6-yl]urea, compound 58) N-(3-bromophenyl)-N'-[2-(3,4-dihydroxyphenyl)-3-hydroxy-4-oxo-4H-chromen-6-yl]urea, compound 59) N-(2,4-dichlorophenyl)-N'-[2-(3,4-dihydroxyphenyl)-3-hydroxy-4-oxo-4H-chromen-6-yl]-urea, compound 60) N-(3-cyanophenyl)-N'-[2-(3,4-dihydroxyphenyl)-3-hydroxy-4-oxo-4H-chromen-6-yl]urea, compound 61) N-[2-(3,4-dihydroxyphenyl)-3-hydroxy-4-oxo-4H-chromen-6-yl]-N'-(4-nitrophenyl)urea, compound 62) N-(4-aminophenyl)-N'-[2-(3,4-dihydroxyphenyl)-3-hydroxy-4-oxo-4H-chromen-6-yl]urea, compound 63) 2-(3,4-dihydroxyphenyl)-3-hydoxy-4H-chromen-4-one, compound 64) 2-(3,4-dihydroxyphenyl)-3,7-dihydroxy-4H-chromen-4-one, compound 65) 2-(3,4-dihydroxyphenyl)-3,5,7-trihydroxy-4H-chromen-4-one, and compound 66) 2-(3,4-dihydroxyphenyl)-3,7,8-trihydroxy-4H-chromen-4-one.

The above compound of formula (1) may also form a pharmaceutically acceptable salt. Such a salt includes non-toxic acid addition salt containing pharmaceutical acceptable anion, for example a salt with inorganic acids such as hydrochloric acid, sulfuric acid, nitric acid, phosphoric acid, hydrobromic acid, hydroiodic acid, etc., a salt with organic carboxylic acids such as tartaric acid, formic acid, citric acid, acetic acid, trichloroacetic acid, trifluoroacetic acid, gluconic acid, benzoic acid, lactic acid, fumaric acid, maleic acid, etc., or a salt with sulfonic acids such as methanesulfonic acid, benzenesulfonic acid, p-toluenesulfonic acid, naphthalenesulfonic acid, etc. The compound of formula (1) may also exist in the form of hydrate or solvate.

Since the compounds according to the present invention may have asymmetric carbon centers, they can be present in the form of racemate, diastereomer or mixtures thereof. Therefore, the present invention also includes all these isomers and their mixtures.

The compound of the formula (1) according to the present invention may be prepared by process described in the following.

First, the compound of formula (1) wherein $R_5$ is hydrogen, namely the compound of the following formula (1a):

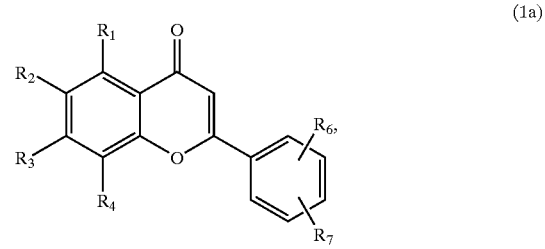

(1a)

wherein $R_1$, $R_2$, $R_3$, $R_4$; and $R_7$ are defined as previously described, or a salt thereof may be prepared characterized by a) cyclizing a compound of the following formula (4):

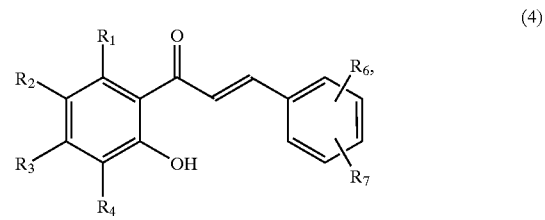

(4)

wherein $R_1$, $R_2$, $R_3$, $R_4$, $R_6$ and $R_7$ are defined as previously described, in the presence of trifluoroacetic acid to give a compound of the following formula (5):

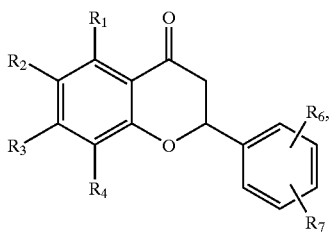

(5)

wherein $R_1$, $R_2$, $R_3$, $R_4$, $R_6$ and $R_7$ are defined as previously described, then reducing the resulting compound of formula (5) in the presence of a reducing agent in a solvent or b) cyclizing a compound of the following formula (6):

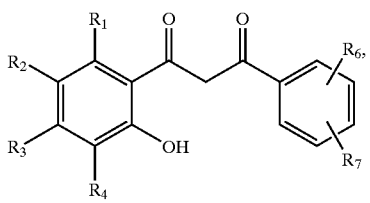

(6)

wherein $R_1$, $R_2$, $R_3$, $R_4$, $R_6$ and $R_7$ are defined as previously described, in the presence of sodium acetate in a solvent.

The processes are depicted in the following Schemes (1) and (2).

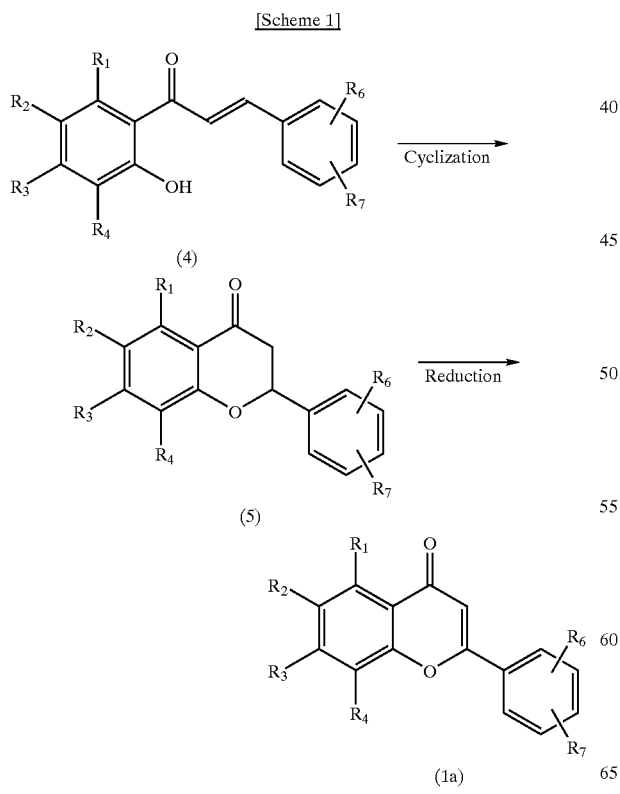

[Scheme 1]

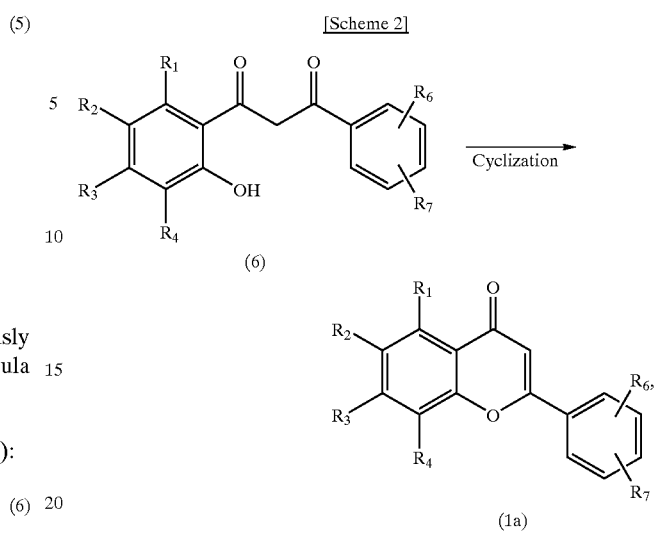

[Scheme 2]

wherein $R_1$, $R_2$, $R_3$, $R_4$, $R_6$ and $R_7$ are defined as previously described.

In the reaction depicted in Scheme (1), the compound of formula (5) is prepared from cyclization of the compound of formula (4) during which the compound (4) is heated under reflux in the presence of trifluoroacetic acid. This reaction is carried out for an enough time, usually for a day, to complete the reaction depending on the kind of reactant. After the cyclization is completed, the chromane derivative of formula (5) thus obtained is oxidized with a oxidizing agent in a solvent to produce the chromene derivative of above formula (1a). As the solvent, one or more selected from the group consisting of benzene and toluene may be preferably used. As the oxidizing agent, 2,3-dichloro-5,6-dicyano-1,4-benzoquinone (DDQ) is used preferably.

In the reaction according to Scheme (2), the compound of formula (1a) wherein $R_5$ is hydrogen is prepared by cyclizing the compound of formula (6) in the presence of sodium acetate in a solvent. At this time, acetic acid is preferably used as the solvent.

Second, the compound of formula (1) wherein $R_5$ is hydroxy, namely the compound of following formula (1b):

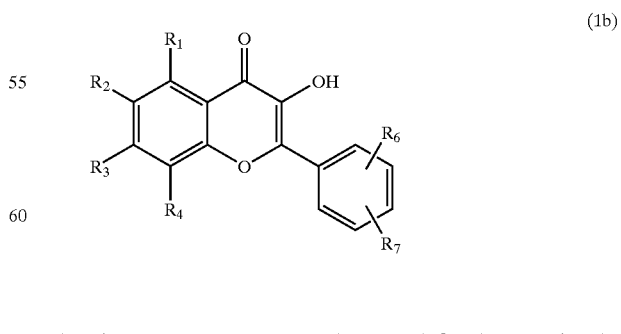

(1b)

wherein $R_1$, $R_2$, $R_3$, $R_4$, $R_6$ and $R_7$ are defined as previously described, or a salt thereof may be prepared characterized by cyclizing the compound of following formula (4):

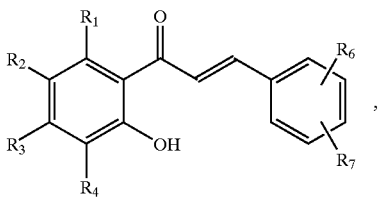

(4)

wherein $R_1$, $R_2$, $R_3$, $R_4$, $R_6$ and $R_7$ are defined as previously described, in the presence of a base and hydrogen peroxide in a solvent.

Especially, the compound of formula (1b) wherein $R_6$ and $R_7$ together represent methylenedioxy, namely the compound of formula (1cc):

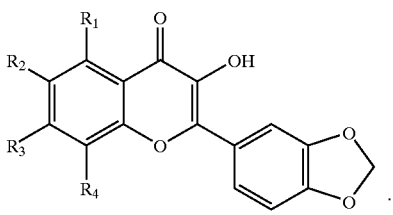

(1cc)

wherein $R_1$, $R_2$, $R_3$ and $R_4$ are defined as previously described, can be prepared from the compound of following formula (4a):

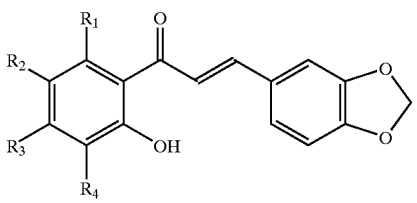

(4a)

wherein $R_1$, $R_2$, $R_3$ and $R_4$ are defined as previously described, according to the above method.

The process of the above reaction is depicted in the following Scheme (3).

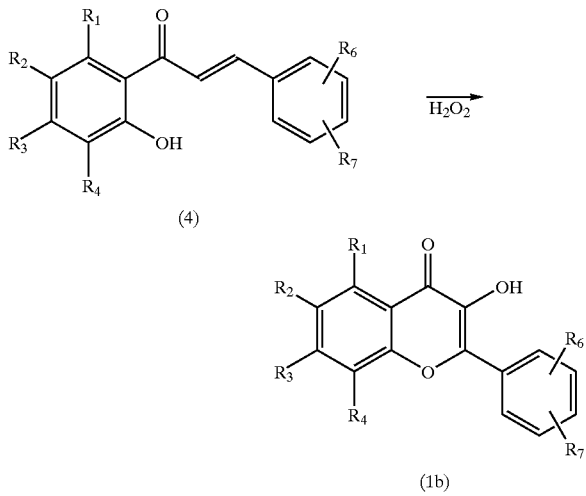

wherein $R_1$, $R_2$, $R_3$, $R_4$, $R_6$ and $R_7$ are defined as previously described.

In the reaction according to the Scheme (3), the compound of formula (1b) is prepared by cyclizing compound of formula (4) in the presence of hydrogen peroxide. In this process, a solvent and a base are used. As the solvent, the one which does not adversely affect the reaction, such as for example, one or more selected from the group consisting of methanol and ethanol, particularly methanol is used. The base includes one or more selected from the group consisting of sodium hydroxide and potassium hydroxide. Particularly an aqueous sodium hydroxide solution having a concentration of 10% is preferable. This reaction should be conducted inevitably by using hydrogen peroxide which is used in excess amount, preferably in an amount of 5 to 10 times molar equivalents with respect to the compound of formula (4). Suitably, it is used in an aqueous solution of 30%. The reaction may be promoted by optionally adding acid catalyst, such as hydrochloric acid. The reaction is usually carried out at room temperature or under warming, and about 3 hours are usually required to complete the reaction at room temperature.

Deprotection reaction may also be carried out to remove the amino- or hydroxy-protecting group which exists optionally.

That is to say, the compound of formula (1) wherein one or more of the substituents $R_1$, $R_2$, $R_3$ and $R_4$ are hydroxy or amino may be prepared characterized by selectively deprotecting the hydroxy or amino group which is protected by lower alkyl or alkanoyl in the presence of boron tribromide or by hydrolyzing with aqueous sulfuric acid solution or alcohol solvent.

Moreover, the compound of formula (1) wherein $R_2$ is

namely the compound of the following formula (1h):

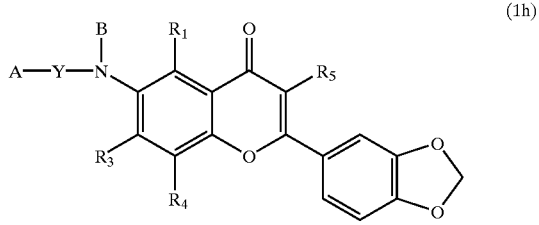

(1h)

wherein $R_1$, $R_3$, $R_4$, $R_5$ and A, Y, B are defined as previously described, may be prepared by reacting the compound of formula (9):

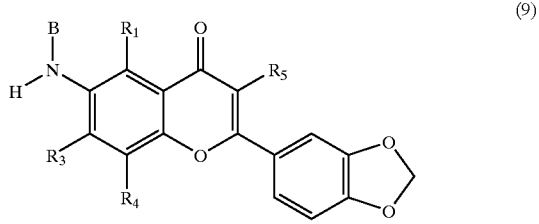

(9)

wherein $R_1$, $R_3$, $R_4$, $R_5$ and B are defined as previously described, with the compound of formula (10):

A—Y—X (10)

wherein A and Y are defined as previously described and X is a leaving group, or with the compound of formula (11):

A'—N=C=O (11)

wherein A' represents aralkyl, acyl or aryl which is optionally substituted with one or two substituents selected from the group consisting of halogen, cyano and nitro.

Especially, the compound of formula (1h) wherein $R_5$ is hydroxy, namely the compound of formula (1hh):

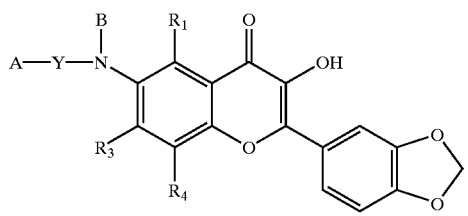
(1hh)

wherein $R_1$, $R_3$, $R_4$, A, Y and B are defined as previously described, can be prepared from the compound of formula (9a):

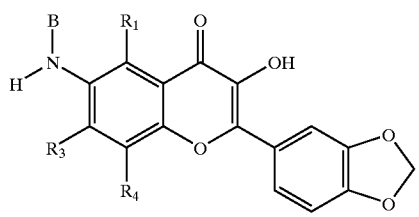
(9a)

wherein $R_1$, $R_3$, $R_1$ and B are defined as previously described, according to the above method.

The compound of formula (9), especially the compound of formula (9a) used in the above method can be prepared by process described in the following.

A compound of formula (4b):

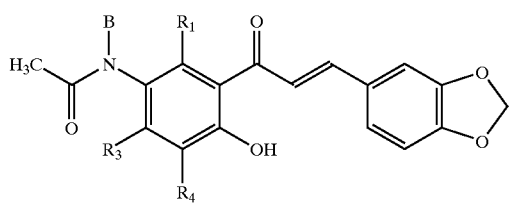
(4b)

wherein $R_1$, $R_3$, $R_4$ and B are defined as previously described, is prepared by reacting 2-hydroxyacetophenone derivative of formula (7a):

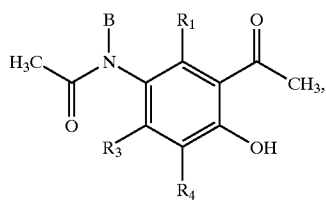
(7a)

wherein $R_1$, $R_3$, $R_4$ and B are defined as previously described, the piperonal of formula (8a):

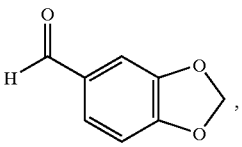
(8a)

and sodium hydroxide in the aqueous ethanol solution solvent, then thus obtained compound of formula (4b) is reacted with aqueous sodium hydroxide and hydrogen peroxide in methanol solvent to produce a compound of formula (1e):

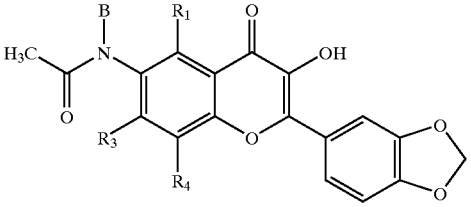
(1e)

wherein $R_1$, $R_3$, $R_4$ and B are defined as previously described.

Then, the above obtained compound of formula (1e) is hydrolyzed with aqueous sulfuric acid solution in alcoholic solvent to give a compound of formula (9a):

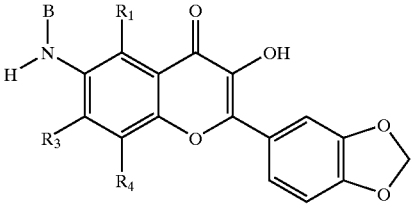
(9a)

wherein $R_1$, $R_3$, $R_4$ and B are defined as previously described.

The compound of formula (1) wherein one to six of the substituents $R_1$, $R_2$, $R_3$, $R_4$, $R_6$ and $R_7$ are hydroxy may be prepared characterized by selectively deprotecting one to six lower alkoxy groups or lower alkylenedioxy group in the compound of formula (1) in order to convert them into hydroxy of dihydroxy group in the presence of boron tribromide.

For example, the compound of formula (1) wherein $R_6$ and $R_7$ represent 3-hydroxy and 4-hydroxy respectively, namely compound of formula (1d):

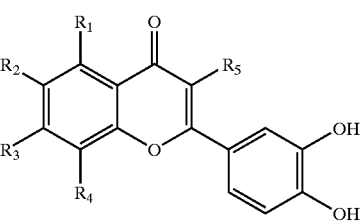
(1d)

wherein $R_1$, $R_2$, $R_3$, $R_.$, and $R_5$ are defined as previously described, may be prepared from the compound of formula (1c):

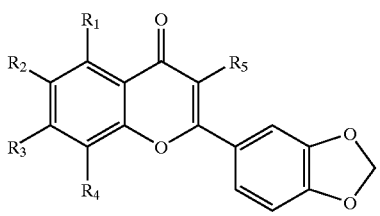

(1c)

wherein $R_1$, $R_2$, $R_4$, $R_4$, and $R_5$ are defined as previously described, according to the reaction as depicted in the following Scheme (4).

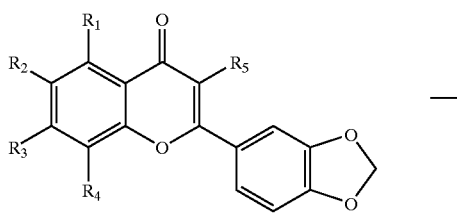

(1c)

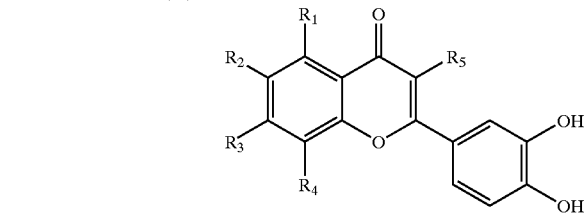

(1d)

wherein $R_1$, $R_2$, $R_3$, $R_4$, and $R_5$ are defined as previously described.

Especially, the compound formula (1d) wherein $R_5$ is hydroxy, namely the compound of formula (1dd):

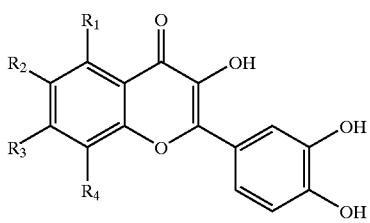

(1dd)

wherein $R_1$, $R_2$, $R_3$ and $R_4$ are defined as previously described, can be prepared from the compound of formula (1cc):

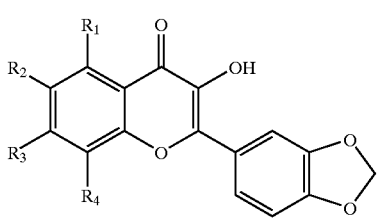

(1cc)

wherein $R_1$, $R_2$, $R_3$ and $R_4$ are defined as previously described, according to the above method.

In addition, the compound of formula (1cc) wherein $R_2$ is

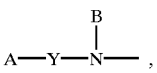

namely the compound of formula (1i):

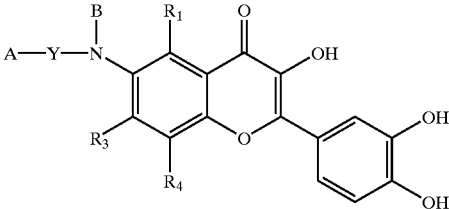

(1i)

wherein $R_1$, $R_3$, $R_4$, A, Y and B are defined as previously described, can be prepared from the compound of formula (1hh):

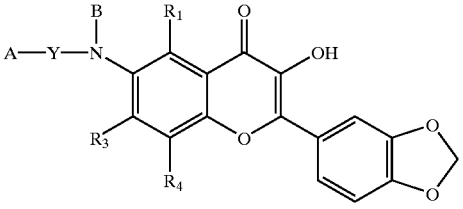

(1hh)

wherein $R_1$, $R_3$, $R_4$, A, Y and B are defined as previously described, according to the above method.

In the reaction according to Scheme 4, the compound of formula (1d) is prepared by opening the dioxolane ring of the compound of formula (1c) to convert it into dihydroxy group. The opening of dioxolane ring is accomplished by a reaction with boron tribromide which is usually used in an amount of 2 to 5 equivalents, preferably 3 equivalents or more, with respect to the compound of formula (1c). This opening reaction is preferably carried out in a solvent and as the solvent, one or more selected from the group consisting of methylenechloride, dioxane, benzene and toluene, preferably methylenechloride, may be mentioned. The reaction is usually carried out at room temperature or under warming and the reaction is completed at room temperature for about 2 hours.

The compound of formula (4) used as a starting material in the above process for preparation of the compound of formula (1) according to the present invention may be produced by reacting a 2-hydroxyacetophenone derivative of the following formula (7)

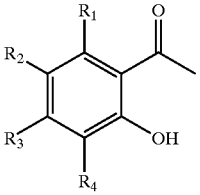

(7)

wherein $R_1$, $R_2$, $R_3$, and $R_4$ are defined as previously described, with a compound of the following formula (8):

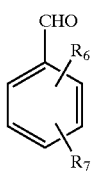

(8)

wherein $R_6$ and $R_7$ are defined as previously described, in the presence of a base in a solvent.

Especially, the compound of formula (4a) can be prepared by reacting the compound of the formula (7) with piperonal of formula (8a)

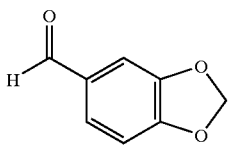

(8a)

according to the above method.

The above reaction is depicted in the following Scheme (5).

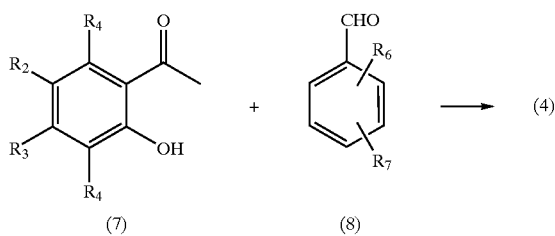

(4)

wherein $R_1$, $R_2$, $R_3$, $R_4$, $R_6$ and $R_7$ are defined as previously described.

In the reaction according to Scheme 5, the compound of formula (4) is prepared by coupling the 2-hydroxyacetophenone derivative of formula (7) with the compound of formula (8) in an amount of 1 to 3 equivalents, preferably 3 equivalents. As the solvent which can be used, one or more selected from the group consisting of water, methanol, ethanol, propanol, butanol and dioxane may be exemplified, and methanol, ethanol or aqueous ethanol solution (80%) is more preferable. As the base, one or more selected from the group consisting of sodium hydroxide, potassium hydroxide, calcium hydroxide, sodium carbonate, potassium carbonate and calcium carbonate, preferably sodium hydroxide, may be mentioned. The amount of base is not particularly restricted, however it is generally used in an amount of 2 to 5 equivalents, preferably 3 equivalents with respect to the compound of formula (7). The reaction is usually carried out at room temperature or under warming and reaction time is variable according to the kind of used solvent or base used, or reaction temperature. The reaction is usually completed at room temperature for about 15 hours.

In the processes as explained in above, the reaction conditions including the amount of reactants, reaction temperature, reaction time, etc. are easily determined depending on the reactants selected by a person having ordinary skill in this art. In general, as for solvent, any one can be used unless it adversely affect the reaction. The reaction temperature may be changeable in variety, however the reaction is preferably carried out at temperatures ranging from 0 to 120° C.

The free compound of formula (1) prepared in the reaction according to the present invention may be converted into the above-mentioned salt in a conventional manner well-known in the art. In addition, after the reaction is completed, the product may be isolated or purified by conventional work up procedures such as chromatography, recrystallization, etc.

The compound of the present invention prepared according to the above method has an inhibitory activity against CDK, and thus may be put to a good use as an anti-cancer agent. Accordingly, another object of the present invention is to provide an anti-cancer agent or an agent for treating neurodegenerative disease which comprises the compound of formula (1), pharmaceutically acceptable salt, hydrate, solvate or isomer thereof as an active ingredient together with pharmaceutically acceptable carrier.

In case the compound of the present invention is administered for clinical purpose, it is preferably administered in an amount ranging from 0.01 to 50 mg/kg of body weight a day. The total daily dosage may be administered in one time or over several times. However, the specific dosage for a specific patient can be varied according to the specific compound used, body weight of the subject patient, sex, hygienic condition, diet, time or method of administration, excretion rate, mixing ratio of the medicine, severity of the disease to be treated, etc.

The compound of the present invention may be administered in the form of injections or oral preparations. Injections such as sterilized aqueous or oily suspension for injection may be prepared by using suitable dispersing agent, humectant or suspension agent according to the known method. As solvents to be used for preparing injections, water, Ringer's fluid and isotonic NaCl solution can be mentioned, and sterilized fixing oil is also used as the solvent or suspension medium. Any non-stimulative fixing oil including mono- or di-glyceride can be used for this purpose, and also fatty acid such as oleic acid can be used for injection formulation.

As the solid preparation for oral administration, capsules, tablets, pills, powders and granules, preferably capsules and tablets can be mentioned. It is desirable for tablets and pills to be formulated into enteric-coated preparation. Solid preparations may be prepared by mixing the active compound of formula (1) according to the present invention with least one carrier selected from a group consisting of inert diluents(e.g. sucrose. lactose, starch, etc.), lubricants(e.g. magnesium stearate), disintegrators, and binders.

The present invention is more specifically explained by the following prepartions and examples. However, it should be understood that the present invention is not limited to these examples in any manner.

Preparation 1

Synthesis of 1-(3,5-Dichloro-2-hydroxy-phenyl)-3-(4-methoxy-phenyl)-propenone

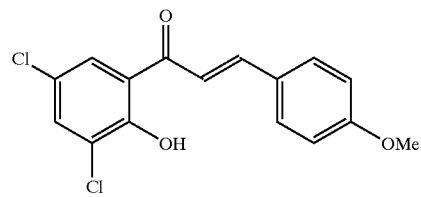

1.0 g (4.8 mmol) of 3',5'-dichloro-2'-hydroxyacetophenone was dissolved in 30 ml of methanol solvent, and then 0.53 g of NaOH (13.2 mmol) was added thereto. The mixture was stirred for 30 minutes. 0.61 g (4.8 mmol) of 4-methoxybenzaldehyde was added thereto, the mixture was heated to 50° C., and then it was stirred for 3 hours. After the reaction was completed, methanol was removed by distillation under reduced pressure. The residue was purified by silica gel column chromatography (eluent: n-hexane/ethylacetate=4/1, v/v) to give the title compound in a yield of 57%.

$^1$H NMR (500 MHz, CDCl$_3$): δ 8.52 (m, 1H), 7.60–7.02 (m, 5H), 6.22–6.00 (m, 2H), 3.90 (s, 3H); MS (FAB): 323 (M+H$^+$).

Preparation 2

Synthesis of 1-(2-Hydroxy-phenyl)-3-(4-methoxy-phenyl)-propenone

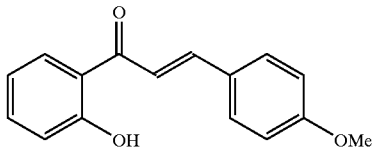

The title compound was obtained in a yield of 80% according to the same procedure as Preparation 1 using 1.0 g (7.3 mmol) of 2'-hydroxyacetophenone and 0.99 g (7.3 mmol) of 4-methoxybenzaldehyde.

$^1$H NMR (500 MHz, CDCl$_3$): δ 7.44–6.66 (m, 8H), 6.21–6.01 (m, 2H), 3.89 (s, 3H); MS (FAB): 255 (M+H$^+$).

Preparation 3

Synthesis of 3-(4-Chloro-phenyl)-1-(2-hydroxy-4-methoxy-phenyl)-propenone

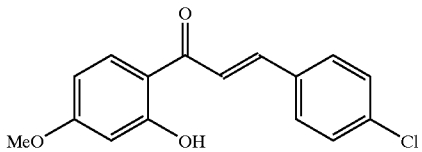

The title compound was obtained in a yield of 77% according to the same procedure as Preparation 1 using 1.0 g (6.0 mmol) of 2'-hydroxy-4'-methoxy acetophenone and 0.84 g (6.0 mmol) of 4-chlorobenzaldehyde.

$^1$H NMR (500 MHz, CDCl$_3$): δ 7.55–6.46 (m, 7H), 6.42–6.21 (m, 2H), 3.99 (s, 3H); MS (FAB): 289 (M+H$^+$).

Preparation 4

Synthesis of 2-(4-Chloro-phenyl)-7-methoxy-chroman-4-one

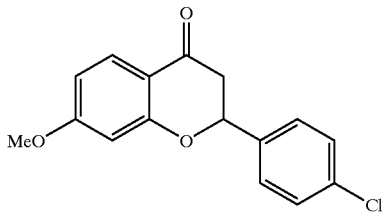

0.1 g (0.35 mmol) of 3-(4-chloro-phenyl)-1-(2-hydroxy-4-methoxy-phenyl)-propenone synthesized in Preparation 3 was refluxed in solvent of trifluoroacetic acid(TFA) for a day, and TFA was removed by distillation under reduced pressure. The residue was purified by silica gel column chromatography (eluent: n-hexane/ethylacetate=5/1, v/v) to give the title compound in a yield of 83%.

$^1$H NMR (500 MHz, CDCl$_3$): δ 7.86 (d, 1H, J=8.7 Hz), 7.42 (m, 4H), 6.62 (d, 1H, J=2.4 Hz), 6.49 (s, 1H), 5.45 (m, 1H), 3.90 (s, 3H), 2.98 (dd, 1H, J=12.7 Hz, J=16.6 Hz), 2.80 (dd, 1H, J=12.9 Hz, J=16.6 Hz); MS (FAB): 289 (M+H$^+$).

Preparation 5

Synthesis of 3-(Benzo[1,3]dioxol-5-yl)-1-(5-chloro-2-hydroxyphenyl)-2-propen-1-one

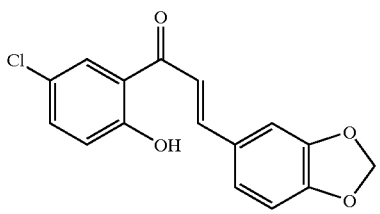

1 g (5.86 mmol) of 5-chloro-2-hydroxyacetophenone, 3 molar equivalents of piperonal, and 3 molar equivalents of sodium hydroxide was mixed in 15 ml of aqueous 80% ethanol solution, and then the mixture was stirred at room temperature for 15 hours. After the reaction was completed, 50 ml of water was added thereto, and the mixture was stirred for about 10 minutes. The obtained pale yellow solid was filtered, washed with water and diethylether, and dried to give 1.42 g (Yield 80%) of the title compound.

$^1$H NMR (CDCl$_3$, ppm); δ 9.80 (1H, br s), 7.84 (1H, s), 7.43 (2H, m), 7.33 (1H, s), 7.19 (1H, m), 6.98 (3H, m), 6.07 (2H, s); FAB MS (m/e)=303 [M$^+$+1],

Preparation 6

Synthesis of 3-(Benzo[1,3]dioxol-5-yl)-1-(5-bromo-2-hydroxyphenyl)-2-propen-1-one

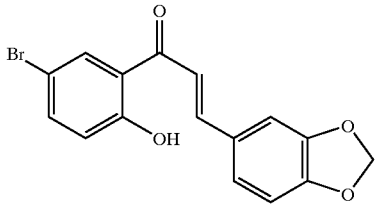

1.5 g (Yield 93%) of the title compound was obtained according to the same procedure as Preparation 5 except that 1 g (4.65 mmol) of 5-bromo-2-hydroxyacetophenone was used instead of 5-chloro-2-hydroxy acetophenone.

$^1$H NMR (CDCl$_3$, ppm); δ 7.99 (1H, s), 7.88 (1H, d), 7.55 (1H, d), 7.37 (1H, d), 7.21–7.17 (2H, m), 6.94 (1H, d), 6.88 (1H, d); FAB MS (m/e)=348 [M$^+$+1].

Preparation 7

Synthesis of 3-(Benzo[1,3]dioxol-5-yl)-1-(2-hydroxy-5-methoxyphenyl)-2-propen-1-one

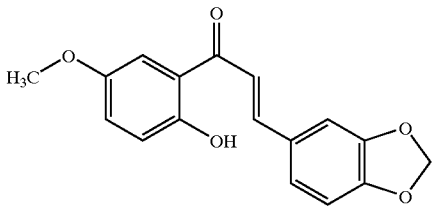

1.3 g (Yield 72%) of the title compound was obtained according to the same procedure as Preparation 5 except that 1 g (6.02 mmol) of 5-methoxy-2-hydroxyacetophenone was used instead of 5-chloro-2-hydroxy acetophenone.

$^1$H NMR (CDCl$_3$, ppm); δ 7.85 (1H, d), 7.40 (1H, d), 7.33 (1H, s), 7.15 (3H, m), 7.00–6.80 (3H, m), 6.07 (2H, s), 3.84 (3H, s); FAB MS (m/e)=299 [M$^+$+1].

Preparation 8

Synthesis of 3-(Benzo[1,3]dioxol-5-yl)-1-(5-fluoro-2-hydroxyphenyl)-2-propen-1-one

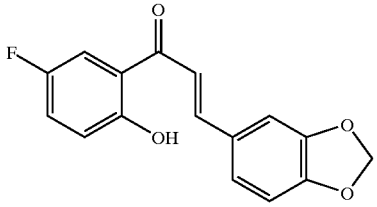

1.6 g (Yield 86%) of the title compound was obtained according to the same procedure as Preparation 5 except that 1 g (6.49 mmol) of 5-fluoro-2-hydroxyacetophenone was used instead of 5-chloro-2-hydroxy acetophenone.

$^1$H NMR (CDCl$_3$, ppm); δ 7.85 (1H, s), 7.80 (1H, d), 7.55 (1H, d), 7.37 (1H, d), 7.21–7.17 (2H, m), 6.94 (1H, d), 6.88 (1H, d); FAB MS (m/e)=287 [M$^+$+1].

Preparation 9

Synthesis of 3-(Benzo[1,3]dioxol-5-yl)-1-(5-methyl-2-hydroxyphenyl)-2-propen-1-one

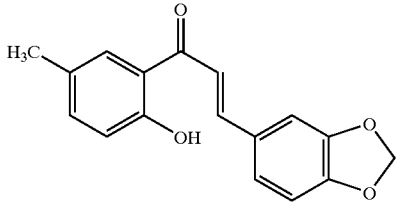

1.7 g (Yield 90%) of the title compound was obtained according to the same procedure as Preparation 5 except that 1 g (6.66 mmol) of 5-methyl-2-hydroxyacetophenone was used instead of 5-chloro-2-hydroxy acetophenone.

$^1$H NMR (CDCl$_3$, ppm); δ 7.73 (1H, s), 7.69 (1H, d), 7.55 (1H, d), 7.37 (1H, d), 7.15–7.25 (2H, m), 6.92 (1H, d), 6.85 (1H, d); FAB MS (m/e)=283 [M$^+$+1].

Preparation 10

Synthesis of 3-(Benzo[1,3]dioxol-5-yl)-1-(3,5-dichloro-2-hydroxyphenyl)-2-propen-1-one

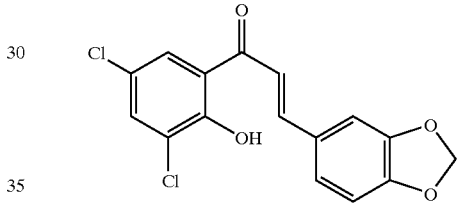

1.4 g (Yield 85%) of the title compound was obtained according to the same procedure as Preparation 5 except that 1 g (4.8 mmol) of 3,5-dichloro-2-hydroxyacetophenone was used instead of 5-chloro-2-hydroxyacetonenone.

$^1$H NMR (DMDO-d$_6$, ppm); δ 8.57 (1H, br s), 8.11 (1H, s), 8.06 (1H, d), 7.88 (1H, d), 7.78 (1H, s), 7.42 (1H, d), 7.04 (1H, d), 6.13 (2H, s); FAB MS (m/e)=337 [M$^+$+1].

Preparation 11

Synthesis of 3-(Benzo[1,3]dioxol-5-yl)-1-(3,5-dibromo-2-hydroxyphenyl)-2-propen-1-one

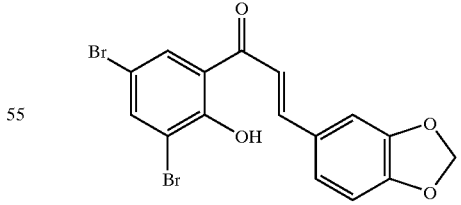

2.9 g (Yield 97%) of the title compound was obtained according to the same procedure as Preparation 5 except that 2 g (6.8 mmol) of 3,5-dibromo-2-hydroxyacetophenone was used instead of 5-chloro-2-hydroxyacetophenone.

$^1$H NMR (DMDO-d$_6$, ppm); δ 8.57 (1H, br s), 8.08 (1H, s), 8.01 (1H, d), 7.88 (1H, d), 7.78 (1H, s), 7.42 (1H, d), 7.04 (1H, d), 6.13 (2H, s); FAB MS (m/e)=427 [M$^+$+1].

Preparation 12

Synthesis of 3-(Benzo[1,3]dioxol-5-yl)-1-(3,5-difluoro-2-hydroxyphenyl)-2-propen-1-one

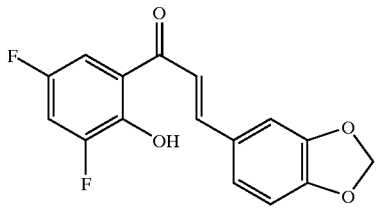

1.6 g (Yield 90%) of the title compound was obtained according to the same procedure as Preparation 5 except that 1 g(5.8 mmol) of 3,5-difluoro-2-hydroxyacetophenone was used instead of 5-chloro-2-hydroxyacetophenone.

$^1$H NMR (DMDO-$d_6$, ppm); δ 8.59 (1H, br s), 8.12 (1H, s), 8.01 (1H, d), 7.88 (1H, d), 7.78 (1H, s), 7.42 (1H, d), 7.04 (1H, d), 6.13 (211, s); FAB MS (m/e)=305 [M$^+$+1].

Preparation 13

Synthesis of 3-(Benzo[1,3]dioxol-5-yl)-1-(5-chloro-2-hydroxy-4-methylphenyl)-2-propen-1-one

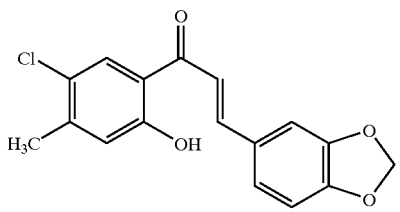

0.77 g (Yield 90%) of the title compound was obtained according to the same procedure as Preparation 5 except that 0.5 g (2.70 mmol) of 4-methyl-5-chloro-2-hydroxyacetophenone was used instead of 5-chloro-2-hydroxyacetophenone.

$^1$H NMR (CDCl$_3$, ppm); δ 7.85 (1N, d), 7.82 (1N, s), 7.38 (1H, d), 7.19 (2H, m), 6.86 (2H, m), 6.07 (2H, s), 2.41 (3H, s); FAB MS (m/e)=317 [M$^+$+1].

Preparation 14

Synthesis of 3-(Benzo[1,3]dioxol-5-yl)-1-(2-hydroxy-4-methoxyphenyl)-2-propen-1-one

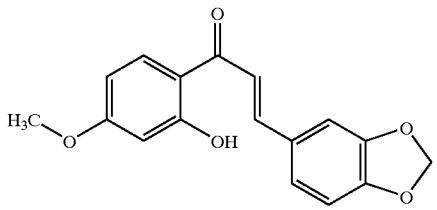

1.3 g (Yield 72%) of the title compound was obtained according to the same procedure as Preparation 5 except that 1 g (6.02 mmol) of 4-methoxy-2-hydroxyacetophenone was used instead of 5-chloro-2-hydroxyacetophenone.

$^1$H NMR (CDCl$_3$, ppm); δ 7.85 (1H, d), 7.40 (1H, d), 7.33 (1H, s), 7.15 (3H, m), 7.00–6.80 (3H, m), 6.07 (2H, s), 3.84 (3H, s); FAB MS (m/e)=299 [M$^+$+1].

Preparation 15

Synthesis of 3-(Benzo[1,3]dioxol-5-yl)-1-(2-hydroxy-3,4-dimethoxyphenyl)-2-propen-1-one

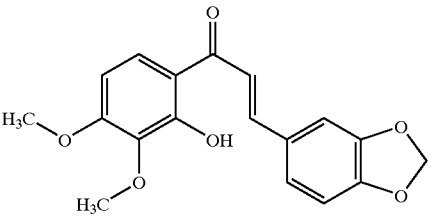

1.2 g (Yield 72%) of the title compound was obtained according to the same procedure as Preparation 5 except that 1 g (5.1 mmol) of 3,4-dimethoxy-2-hydroxyacetophenone was used instead of 5-chloro-2-hydroxyacetophenone.

$^1$H NMR (CDCl$_3$, ppm); δ 7.85 (1H, d), 7.40 (1H, d), 7.33 (1H, s), 7.15 (1H, m), 7.00–6.80 (3H, m), 6.07 (2H, s), 3.84 (6H, s); FAB MS (m/e)=329 [M$^+$+1].

Preparation 16

Synthesis of 3-(Benzo[1,3]dioxol-5-yl)-1-(2-hydroxy-3-methoxyphenyl)-2-propen-1-one

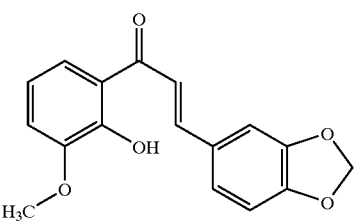

1.2 g (Yield 67%) of the title compound was obtained according to the same procedure as Preparation 5 except that 1 g (6.02 mmol) of 3-methoxy-2-hydroxyacetophenone was used instead of 5-chloro-2-hydroxyacetophenone.

$^1$H NMR (CDCl$_3$, ppm); δ 7.85 (1H, d), 7.40 (1H, m), 7.33 (1H, s), 7.15 (1H, m), 7.00–6.80 (3H, m), 6.07 (2H, s), 3.84 (3H, s); FAB MS (m/e)=299 [M$^+$+1].

Preparation 17

Synthesis of 3-(Benzo[1,3]dioxol-5-yl)-1-(2-hydroxy-4,5-dimethylphenyl)-2-propen-1-one

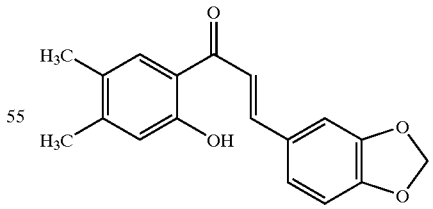

1.77 g (Yield 97%) of the title compound was obtained according to the same procedure as Preparation 5 except that 1 g (6.09 mmol) of 4,5-dimethyl-2-hydroxyacetophenone was used instead of 5-chloro-2-hydroxyacetophenone.

$^1$H NMR (CDCl$_3$, ppm); δ 7.75 (1H, s), 7.62 (1H, s), 7.38 (1H, d), 7.19 (2H, m), 6.86 (2H, m), 6.07 (2H, s), 2.41 (6H, s); FAB MS (m/e)=297 [M$^+$+1].

Preparation 18

Synthesis of 3-(Benzo[1,3]dioxol-5-yl)-1-(2-hydroxy-6-methoxyphenyl)-2-propen-1-one

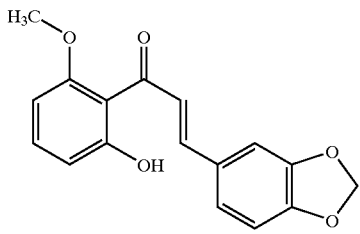

1.25 g (Yield 70%) of the title compound was obtained according to the same procedure as Preparation 5 except that 1 g (6.02 mmol of 6-methoxy-2-hydroxyacetophenone was used instead of 5-chloro-2-hydroxyacetophenone.

$^1$H NMR (CDCl$_3$, ppm); δ 7.80–6.71 (m, 6H), 6.22–6.00 (m, 2H), 5.90 (s, 2H), 3.83 (s, 3H); FAB MS (m/e)=299 [M$^+$+1].

Preparation 19

Synthesis of N-{3-[3-(Benzo[1,3]dioxol-5-yl)-2-propenoyl]-4-hydroxyphenyl}acetamide

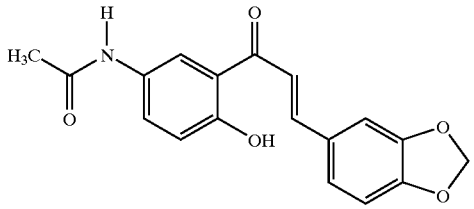

7.0 g (36.23 mmol) of 5-acetamido-2-hydroxyacetophenone, 3 molar equivalents of piperonal and 3 molar equivalents (4.32 g, 108 mmol) of of sodium hydroxide was mixtured in 50 ml of aqueous 80% ethanol solution, and then stirred at room temperature for 20 hours. After the reaction was completed, 100 ml of water was added thereto, and the mixture was further stirred for 10 minutes. The obtained white solid was filtered, washed with water and ethyl ether, and dried to give 9.46 g of the title compound in a yield of 80%.

$^1$H NMR (DMSO-d$_6$, ppm); δ 11.94 (1H, s), 9.86 (1H, s), 8.13 (1H, s), 7.80–7.67 (3H, m), 7.52 (1H, s), 7.32 (1H, d), 7.03 (1H, d), 6.95 (1H, d), 6.12 (2H, s), 2.02 (3H, s); FAB MS (m/e)=326 [M$^+$+1].

EXAMPLE 1

Synthesis of 2-(4-Chloro-phenyl)-7-methoxy-chromen-4-one (Compound 1)

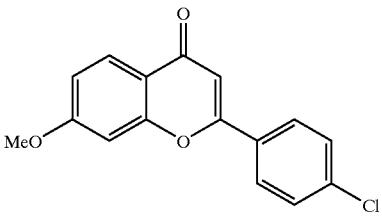

50 mg (0.17 mmol) of 2-(4-chloro-phenyl)-7-methoxy-chroman-4-one synthesized in Preparation 4 and 3.0 molar equivalents (0.12 g, 0.51 mmol) of 2,3-dichloro-5,6-dicyano-1,4-benzoquinone was refuxed in benzene solvent for a day, and then benzene was removed by distillation under reduced pressure. The residue was purified by silica gel column chromatography (eluent: n-hexane/ethylacetate= 5/1, v/v) to give the title compound in a yield of 79%.

$^1$H NMR (500 MHz, CDCl$_3$): δ 8.12 (d, 1H, J=9.3 Hz), 7.84 (d, 2H, J=8.8 Hz), 7.49 (d, 2H, 8.8 Hz), 7.00 (m, 2H), 6.72 (s, 1H), 3.95 (s, 3H); MS (FAB): 287 (M+H$^+$).

EXAMPLE 2

Synthesis of 7-Methoxy-2-phenyl-chromen-4-one (Compound 2)

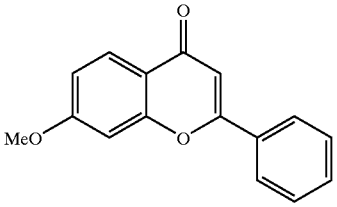

240 mg (0.89 mmol) of 1-(2-hydroxy-4-methoxy-phenyl)-3-phenyl-propan-1,3-dione was dissolved in acetic acid, and 0.73 g (8.9 mmol) of sodium acetate was added thereto. The mixture was refluxed overnight. Acetic acid was removed by distillation under reduced pressure, and then the residue was purified by silica gel column chromatography (eluent: n-hexane/ethylacetate=5/1, v/v) to give the title compound in a yield of 70%.

$^1$H NMR (500 MHz, CDCl$_3$): δ 8.20 (m, 1H), 7.91 (m, 2H), 7.55 (m, 3H), 6.97 (m, 3H), 3.90 (s, 3H); MS (FAB): 253 (M+H$^+$).

EXAMPLE 3

Synthesis of 7-Hydroxy-2-phenyl-chromen-4-one (Compound 3)

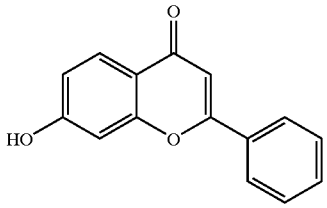

100 mg (0.4 mmol) of compound 7-methoxy-2-phenyl-chromen-4-one obtained in Example 2 was dissolved in methylenechloride, and 2.0 molar equivalents of $BBr_3$ was added thereto. The mixture was stirred for 1 hour. Methanol was added to the mixture, and then solvent was removed by distillation under reduced pressure. The residue was purified by silica gel column chromatography (eluent: methylenechloride/methanol=5/95, v/v) to give the title compound in a yield of 64%.

$^1$N NMR (500 MHz, $d_4$-MeOH): δ 8.04 (m, 1H), 7.90 (m, 2H), 7.61 (m, 3H), 6.92 (m, 2H), 6.72 (m, 1H); MS (FAB): 239 (M+H$^+$).

EXAMPLE 4

Synthesis of 2-(Benzo[1,3]dioxol-5-yl)-3-hydroxy-5-methoxy-chromen-4-one (Compound 4)

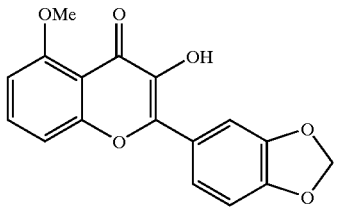

100 mg (0.35 mmol) of 3-(benzo[1,3]dioxol-5-yl)-1-(2-hydroxy-6-methoxyphenyl)-propenone obtained in Preparation 18 was dissolved in 5 ml of methanol, and then 6 ml of 10% NaOH and 3.9 ml of 30% $H_2O_2$ was added thereto. The mixture was stirred for 1 hour. 20 ml of water was added to the mixture, and then 10 ml of 10% HCl was added thereto, and then the mixture was extracted with ethylacetate. The extracted ethylacetate solution was distilled under reduced pressure, and the residue was purified by silica gel column chromatography (eluent n-hexane/ethylacetate=4/1, v/v) to give the title compound in a yield of 95%.

$^1$H NMR (500 MHz, $d_4$-MeOH): δ 7.70–6.72 (m, 6H), 6.00 (s, 2H), 3.92 (s, 3H); MS (FAB): 3 13 (M+H$^+$).

EXAMPLE 5

Synthesis of 2-(Benzo[1,3]dioxol-5-yl)-3-hydroxy-6-methoxy-chromen-4-one (Compound 5)

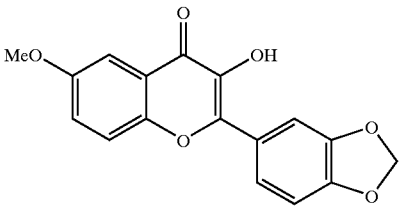

The reaction was conducted according to the same procedure as Example 4 except that 100 mg (0.35 mmol) of 3-(benzo[1,3]dioxol-5-yl)-1-(2-hydroxy-5-methoxy-phenyl)-propenone obtained in Preparation 7 was used as a starting material. Then the residue was purified by silica gel column chromatography (eluent: n-hexane/ethylacetate=4/1, v/v) to give the title compound in a yield of 90%.

$^1$H NMR (500 MHz, $d_4$-MeOH): δ 7.56–6.62 (m, 6H), 6.08 (s, 2H), 3.89 (s, 3H); MS (FAB): 313 (M+H$^+$).

EXAMPLE 6

Synthesis of 2-(Benzo[1,3]dioxol-5-yl)-3-hydroxy-7-methoxy-chromen-4-one (Compound 6)

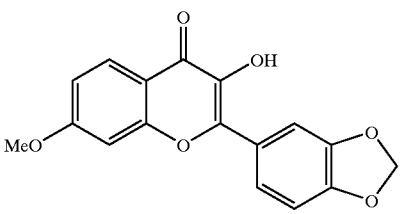

The reaction was conducted according to the same procedure as Example 4 except that 100 mg (0.35 mmol) of 3-(benzo[1,3]dioxol-5-yl)-1-(2-hydroxy-4-methoxy-phenyl)-propenone obtained in Preparation 14 was used as a starting material. Then the residue was purified by silica gel column chromatography (eluent: n-hexane/ethylacetate=4/1, v/v) to give the title compound in a yield of 85%.

$^1$H NMR (500 MHz, $d_4$-MeOH): δ 7.30–6.79 (m, 6H), 6.00 (s, 2H), 3.90 (s, 3H); MS (FAB): 313 (M+H$^+$).

EXAMPLE 7

Synthesis of 3-Hydroxy-7-methoxy-2-(4-methoxy-phenyl)-chromen-4-one (Compound 7)

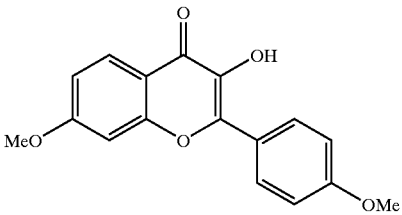

The reaction was conducted according to the same procedure as Example 4 except that 57 mg (0.2 mmol) of 1-(2-hydroxy-4-methoxy-phenyl)-3-(4-methoxy-phenyl)- propenone was used as a starting material. Then the residue was purified by silica gel column chromatography (eluent: n-hexane/ethylacetate=4/1, v/v) to give the title compound in a yield of 92%.

$^1$H NMR (500 MHz, $d_4$-MeOH): δ 7.60–6.70 (m, 7H), 3.90 (s, 3H), 3.87 (s, 3H); MS (FAB): 299 (M+H$^+$).

EXAMPLE 8

Synthesis of 2-(4-Chloro-phenyl)-3-hydroxy-7-methoxy-chromen-4-one (Compound 8)

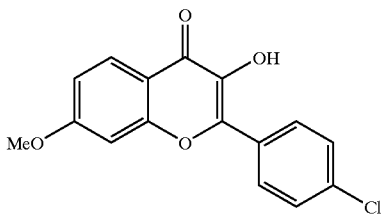

The reaction was conducted according to the same procedure as Example 4 except that 200 mg (0.69 mmol) of 3-(4-chloro-phenyl)-1-(2-hydroxy-4-methoxy-phenyl)-propenone obtained in Preparation 3 was used as a starting material. Then the residue was purified by silica gel column chromatography (eluent: n-hexane/ethylacetate=4/1, v/v) to give the title compound in a yield of 89%.

$^1$H NMR (500 MHz, $d_4$-MeOH): δ 7.50–6.80 (m, 7H), 3.92 (s, 3H); MS (FAB): 303 (M+H$^+$).

EXAMPLE 9

Synthesis of 6-Chloro-3-hydroxy-2-(4-methoxy-phenyl)-8-nitro-chromen-4one (Compound 9)

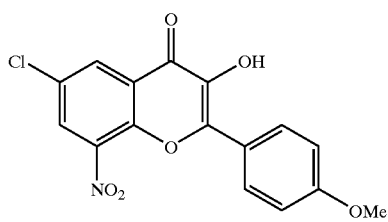

The reaction was conducted according to the same procedure as Example 4 except that 170 mg (0.51 mmol) of 1-(5-chloro-2-hydroxy-3-nitro-phenyl)-3-(4-methoxy-phenyl)-propenone was used as a starting material. Then the residue was purified by silica gel column chromatography (eluent: n-hexane/ethylacetate=2/1, v/v) to give the title compound in a yield of 76%.

$^1$H NMR (500 MHz, $d_4$-MeOH): δ 8.00 (s, 1H), 7.67 (m, 1H), 7.47–6.78 (m, 4H), 3.87 (s, 3H) MS (FAB): 348 (M+H$^+$).

EXAMPLE 10

Synthesis of 6,8-Dichloro-3-hydroxy-2-(4-methoxy-phenyl)-chromen-4-one (Compound 10)

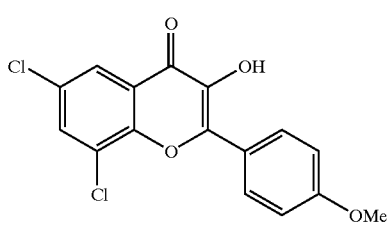

The reaction was conducted according to the same procedure as Example 4 except that 150mg (0.47 mmol) of 1-(3,5-dichloro-2-hydroxy-phenyl)-3-(4-methoxy-phenyl)-propenone obtained in Preparation 1 was used as a starting material. Then the residue was purified by silica gel column chromatography (eluent: n-hexane/ethylacetate=4/1, v/v) to give the title compound in a yield of 79%.

$^1$H NMR (500 MHz, d6-DMSO): δ 8.23–7.90 (m, 4H), 7.11 (m, 2H), 3.87 (s, 3H); MS (FAB): 337 (M+H$^+$).

EXAMPLE 11

Synthesis of 3-Hydroxy-2-(4-methoxy-phenyl)-chromen-4-one (Compound 11)

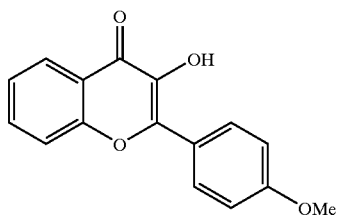

The reaction was conducted according to the same procedure as Example 4 except that 220 mg (0.87 mmol) of 1-(2-hydroxy-phenyl)-3-(4-methoxy-phenyl)-propenone obtained in Preparation 2 was used as a starting material. Then the residue was purified by silica gel column chromatography (eluent: n-hexane/ethylacetate=4/1, v/v) to give the title compound in a yield of 91%.

$^1$H NMR (500 MHz, $d_6$-DMSO): δ 8.20 (m, 3H), 7.81 (m, 2H), 7.45 (m, 1H), 7.18 (m, 2H), 3.91 (s, 3H); MS (FAB): 269 (M+H$^+$).

EXAMPLE 12

Synthesis of 2-(Benzo[1,3]dioxol-5-yl)-6-chloro-3-hydroxy-4H-chromen-4-one

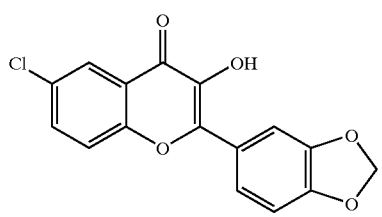

1 g (3.31 mmol) of the compound obtained in Preparation 5 was dissolved in 5 ml of methanol, and 2 ml of aqueous 10% sodium hydroxide solution and 2 mg of 30% hydrogen peroxide solution were added thereto. Then the mixture was stirred at room temperature for 3 hours. The mixture was diluted with 5 ml of water, and acidified with 4N of hydrochloric acid. Then the resulting product was filtered to give 0.83 g (Yield 80%) of the title compound as pale yellow solid.

$^1$H NMR (CDCl$_3$, ppm); δ 8.20 (1H, br s), 7.75 (1H, s), 7.70 (1H, d), 7.54 (1H, d), 7.50 (1H, s), 6.99 (2H, m); FAB MS (m/e)=317 [M$^+$+1].

EXAMPLE 13

Synthesis of 2-(Benzo[1,3]dioxol-5-yl)-6-bromo-3-hydroxy-4H-chromen-4-one

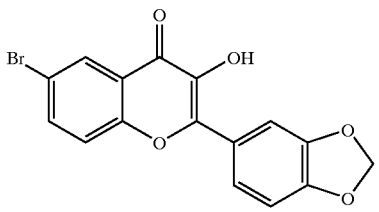

0.89 g (Yield 85%) of the title compound was obtained according to the same procedure as Example 12 except that 1 g (2.89 mmol) of the compound obtained in Preparation 6 was used instead of the compound obtained in Preparation 5.

$^1$H NMR (CDCl$_3$+DMSO-d$_6$, ppm); δ 8.47 (1H, s), 8.32 (1H, s), 7.95–7.75 (3H, m), 6.96 (1H, d), 6.07 (2H, s); FAB MS (m/e)=362 [M$^+$+1].

EXAMPLE 14

Synthesis of 2-(Benzo[1,3]dioxol-5-yl)-6-fluoro-3-hydroxy-4H-chromen-4-one

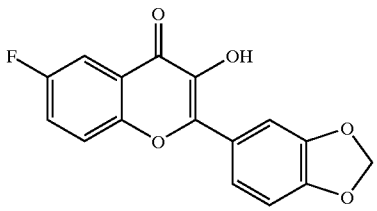

0.85 g (Yield 81%) of the title compound was obtained according to the same procedure as Example 12 except that 1.0 g (3.48 mmol) of the compound obtained in Preparation 8 was used instead of the compound obtained in Preparation 5.

$^1$H NMR (CDCl$_3$, ppm); δ 8.30 (1H, br s), 7.79 (1H, s), 7.70 (1H, d), 7.54 (1H, d), 7.50 (1H, s), 6.99 (2H, m); FAB MS (m/e)=301 [M$^+$+1].

EXAMPLE 15

Synthesis of 2-(Benzo[1,3]dioxol-5-yl)-6-methyl-3-hydroxy-4H-chromen-4-one

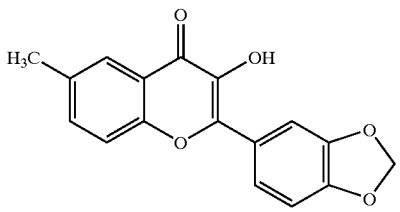

1.3 g (Yield 82%) of the title compound was obtained according to the same procedure as Example 12 except that 1.5 g (5.3 mmol) of the compound obtained in Preparation 9 was used instead of the. compound obtained in Preparation 5.

$^1$H NMR (CDCl$_3$, ppm); δ 7.78 (1H, br s), 7.45 (1H, s), 7.40 (1H, d), 7.34 (1H, d), 7.30 (1H, s), 6.99 (2H, m); FAB MS (m/e)=297 [M$^+$+1].

EXAMPLE 16

Synthesis of 2-(Benzo[1,3]dioxol-5-yl)-6,8-dichloro-3-hydroxy-4H-chromen-4-one

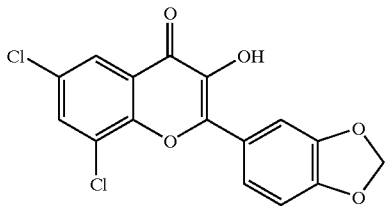

1.3 g (Yield 89%) of the title compound was obtained according to the same procedure as Example 12 except that 1.4 g (4.1 mmol) of the compound obtained in Preparation 10 was used instead of the compound obtained in Preparation 5.

$^1$H NMR (CDCl$_3$, ppm); δ 10.00 (1H, br s), 8.46 (1H, s), 8.20 (1H, s), 7.95 (1H, d), 7.75 (1H, s), 7.53 (1H, d), 6.15 (2H, s); FAB MS (m/e)=351 [M$^+$+1].

EXAMPLE 17

Synthesis of 2-(Benzo[1,3]dioxol-5-yl)-6,8-dibromo-3-hydroxy-4H-chromen-4-one

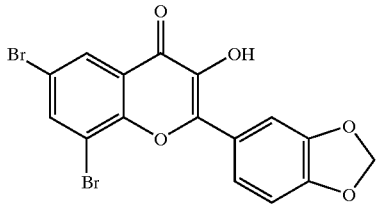

1.86 g (Yield 62%) of the title compound was obtained according to the same procedure as Example 12 except that 2.9 g (6.79 mmol) of the compound obtained in Preparation 11 was used instead of the compound obtained in Preparation 5.

¹H NMR (CDCl₃, ppm); δ 10.05 (1H, br s), 8.35 (1H, s), 8.15 (1H, s), 7.90 (1H, d), 7.75 (1H, s), 7.53 (1H, d), 6.15 (2H, s); FAB MS (m/e)=441 [M⁺+1].

EXAMPLE 18

Synthesis of 2-(Benzo[1,3]dioxol-5-yl)-6,8-difluoro-3-hydroxy-4H-chromen-4-one

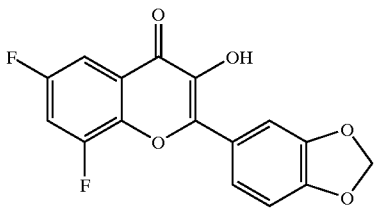

1.5 g (Yield 89%) of the title compound was obtained according to the same procedure as Example 12 except that 1.6 g (5.2 mmol) of the compound obtained in Preparation 12 was used instead of the compound obtained in Preparation 5.

¹H NMR (CDCl₃, ppm); δ 10.00 (1H, br s), 8.37 (1H, s), 8.19 (1H, s), 7.91 (1H, d), 7.75 (1H, s), 7.53 (1H, d), 6.15 (2H, s); FAB MS (m/e)=319 [M⁺+1].

EXAMPLE 19

Synthesis of 2-(Benzo[1,3]dioxol-5-yl)-6chloro-3-hydroxy-7-methyl-4H-chromen-4-one

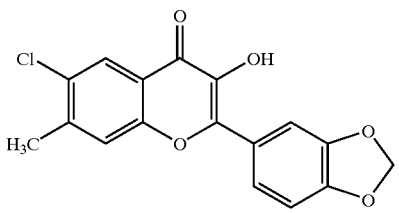

44 mg (Yield 85%) of the title compound was obtained according to the same procedure as Example 12 except that 50 mg (157 pmol) of the compound obtained in Preparation 13 was used instead of the compound obtained in Preparation 5.

¹H NMR (CDCl₃, ppm); δ 8.20 (1H, br s), 7.75 (1H, s), 7.70 (1H, d), 7.54 (1H, d), 7.50 (1H, s), 6.99 (2H, m); FAB MS (m/e)=331 [M⁺+1].

EXAMPLE 20

Synthesis of 2-(Benzo[1,3]dioxol-5-yl)-3-hydroxy-7,8-dimethoxy-4H-chromen-4-one

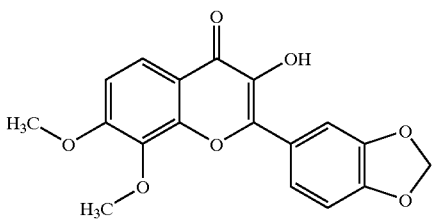

80 mg (Yield 76%) of the title compound was obtained according to the same procedure as Example 12 except that 100 mg (303 pmol) of the compound obtained in Preparation 15 was used instead of the compound obtained in Preparation 5.

¹H NMR (CDCl₃, ppm); δ 7.87 (1H, d), 7.77 (1H, d), 7.56 (1H, s), 7.51 (1H, m), 6.98 (1H, d), 6.07 (2H, s), 3.92 (6H, s); FAB MS (m/e)=343 [M⁺+1].

EXAMPLE 21

Synthesis of 2-(Benzo[1,3]dioxol-5-yl)-3-hydroxy-8-methoxy-4H-chromen-4-one

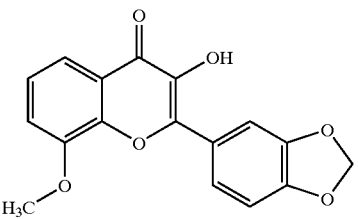

80 mg (Yield 76%) of the title compound was obtained according to the same procedure as Example 12 except that 100 mg (335 pmol) of the compound obtained in Preparation 16 was used instead of the compound obtained in Preparation 5.

¹H NMR (CDCl₃, ppm); δ 7.87 (1H, d), 7.77 (1H, d), 7.56 (1H, s), 7.51 (1H, m), 7.31–7.26 (2H, m), 6.98 (1H, d), 6.07 (2H, s), 3.92 (3 H, s); FAB MS (m/e)=313 [M⁺+1].

EXAMPLE 22

Synthesis of 2-(Benzo[1,3]dioxol-5-yl)-3-hydroxy-6,7-dimethyl-4H-chromen-4-one

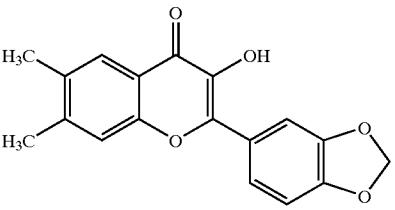

95 mg (Yield 90%) of the title compound was obtained according to the same procedure as Example 12 except that 100 mg (337 pmol) of the compound obtained in Preparation 17 was used instead of the compound obtained in Preparation 5.

¹H NMR (CDCl₃, ppm); δ 7.84 (1H, s), 7.37 (2H, m), 7.18 (1H, s), 6.91 (1H, m), 6.07 (2H, s), 2.39 (6H, s); FAB MS (m/e)=311 [M⁺+1].

EXAMPLE 23

Synthesis of N-[2-(Benzo[1,3]dioxol-5-yl)-3-hydroxy-4-oxo-4H-chromen-6-yl]acetamide

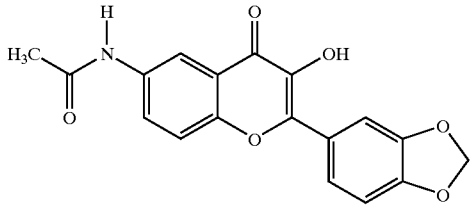

4 g (12.3 mmol) of the compound obtained in Preparation 19 was dissolved in 50 ml of methanol, and 10 ml of aqueous 10% sodium hydroxide solution and 10 ml of 30% hydrogen peroxide solution were added thereto. Then the mixture was stiffed at room temperature for 5 hours. The mixture was diluted with 50 ml of water, and acidified with 4N of hydrochloric acid. Then the resulting product was filtered to give 3.29 g (Yield 79%) of the title compound as pale yellow solid.

$^1$H NMR (DMSO-d$_6$, ppm); δ 10.24 (1H, br s), 9.49 (1H, br s), 8.40 (1H, s), 7.90–7.71 (4H, m), 7.12 (1H, d), 2.08 (3H, s); FAB MS (m/e)=340 [M$^+$+1].

EXAMPLE 24

Synthesis of 6-amino-2-(Benzo[1,3]dioxol-5-yl)-3-hydroxy-4H-chromen-4-one

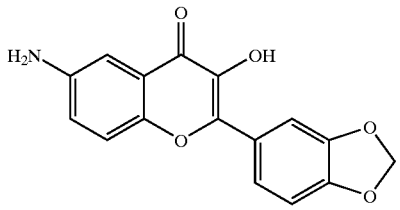

3 g (8.85 mmol) of the compound obtained in Example 23 was stirred in 30 ml of aqueous 80% ethanol solution and 10 ml of aqueous 30% sulfuric acid solution at 120° C. for 18 hours. After the reaction was completed, the mixture was cooled to room temperature, and neutralized with conc. ammonia water. Then the obtained solid was filtered, washed with water, and dried to give 1.8 g of the title compound in a yield of 68%.

$^1$H NMR (CDCl$_3$, ppm); δ 7.85 (1H, d), 7.75 (1H, s), 7.39 (1H, d), 7.08 (1H, d), 6.97 (2H, m), 6.05 (2H, s), 3.86 (2H, br s); FAB MS (m/e)=298 [M$^+$+1].

EXAMPLE 25

Synthesis of N-[2-(Benzo[1,3]dioxol-5-yl-1)-3-hydroxy-4-oxo-4H-chromen-6-yl]-4-methylbenzenesulfonamide

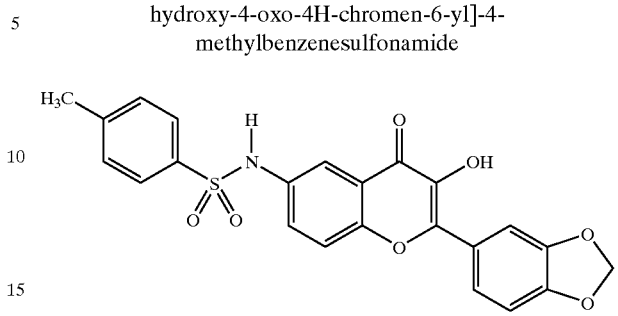

50 mg (168 pmol) of 6-amino-2-(benzo[1,3]dioxol-5-yl)-3-hydroxy-4H-chromen-4-one obtained in Example 24 was dissolved in 5 ml of methylenechloride, then 2 molar equivalents of 4-toluenesulfonyl chloride (p-TsCl) and 3 molar equivalents of triethyl amine were added thereto. The mixture was reacted at room temperature for 10 hours. The resulting product was concentrated under reduced pressure, and separated by preparative TLC to give 34 mg of the title compound in a yield of 45%.

$^1$H NMR (CDCl$_3$, ppm); δ 7.79 (2H, d), 7.50–7.20 (8H, m), 6.99 (1H, d), 6.05 (2H, s), 2.47 (3H, s). FAB MS (m/e)=452 [M$^+$+1].

EXAMPLE 26

Synthesis of N-[2-(Benzo[1,3]dioxol-5-yl)-3-hydroxy-4-oxo-4H-chromen-6-yl]-4-bromobenzenesulfonamide

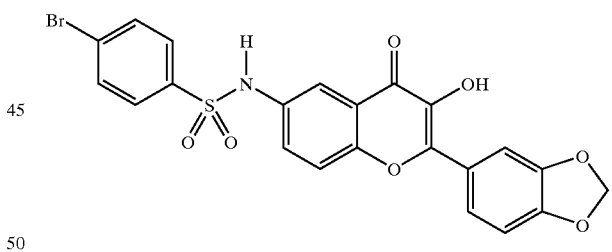

100 mg (336 pmol) of 6-amino-2-(benzo[1,3]dioxol-5-yl)-3-hydroxy-4H-chromen-4-one obtained in Example 24 was dissolved in 3 ml of pyridine, and the mixture was reacted with 2 molar equivalents of 4-bromobenzenesulfonylchloride at room temperature for 5 hours. After the reaction was completed, the product was diluted with 10 ml. of water, and the obtained solid was filtered. Then the resulting product was washed with water and ethylether, and dried to give 159 mg of the title compound in a yield of 91.6%.

$^1$H NMR (MeOH-d$_4$, ppm); δ 8.69 (1H, s), 8.11 (1H, s), 7.92–7.70 (6H, m), 7.58 (1H, m), 7.01 (1H, d), 6.06 (2H, s). FAB MS (m/e)=517 [M$^+$+1].

EXAMPLE 27

Synthesis of N-[2-(Benzo[1,3]dioxol-5-yl)-3-hydroxy-4-oxo-4H-chromen-6-yl]-3-bromobenzenesulfonamide

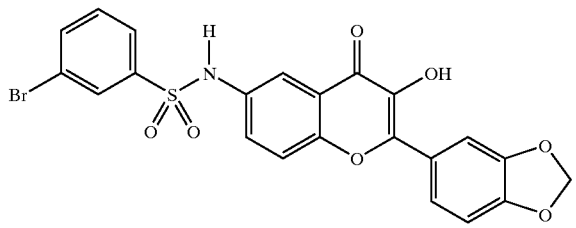

24 mg (Yield 69.4%) of the title compound was obtained according to the same procedure as Example 26 except that 3-bromobenzenesulfonylchloride and 20 mg (67 pmol) of 6-amino-2-(benzo[1,3]dioxol-5-yl)-3-hydroxy-4H-chromen4-one were used instead of 4-bromobenzenesulfonylchloride.

$^1$H NMR (DMSO-d$_6$, ppm); δ 10.70 (11H, br s), 9.55 (1H, s), 7.91 (1H, s), 7.85 (1H, d), 7.80 (1H, d), 7.72 (4H, m), 7.50 (2H, m), 7.11 (1H, d), 6.12 (2H, s). FAB MS (m/e)=517 [M$^+$+1].

EXAMPLE 28

Synthesis of N-[2-(Benzo[1,3]dioxol-5-yl)-3-hydroxy-4-oxo-4H-chromen-6-yl]-2-naphthalenesulfonamide

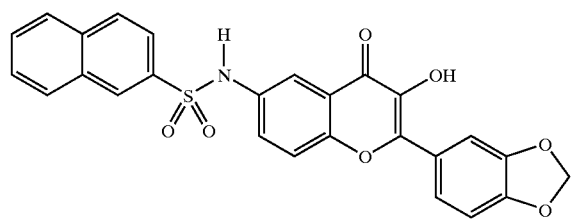

27 mg (Yield 82.5%) of the title compound was obtained according to the same procedure as Example 26 except that 2-naphthalenesulfonylchloride was used instead of 4-bromobenzene sulfonylchlonrde.

$^1$H NMR (DMSO-d$_6$, ppm); δ 10.69 (1H, br s), 9.48 (1H, s), 8.45 (1H, s), 8.15 (2H, m), 8.00 (1H, d), 7.78–7.55 (8H, m), 7.09 (1H, d), 6.11 (2H, s). FAB MS (m/e)=488 [M$^+$+1].

EXAMPLE 29

Synthesis of N-[2-(Benzo[1,3]dioxol-5-yl)-3-hydroxy-4-oxo-4H-chromen-6-yl]-5-(dimethylamino)-1-naphthalenesulfonamide

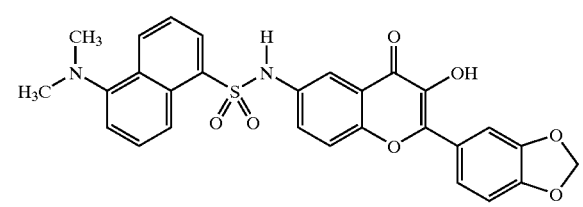

22 mg (Yield 61.7%) of the title compound was obtained according to the same procedure as Example 26 except that 5-dimethylamino-1-naphthalenesulfonylchloride(Dansyl chloride) was used instead of 4-bromobenzenesulfonylchloride.

$^1$H NMR (DMSO-d$_6$, ppm); δ 10.97 (1H, br s), 9.46 (1H, s), 8.44 (1H, d), 8.38 (1H, d), 8.22 (1H, d), 7.75–7.61 (6H, m), 7.45 (1H, d), 7.26 (1H, d), 7.07 (1H, d), 6.11 (2H, s), 2.79 (6H, s). FAB MS (m/e)=531 [M$^+$+1].

EXAMPLE 30

Synthesis of N-[2-(Benzo[1,3]dioxol-5-yl)-3-hydroxy-4-oxo-4H-chromen-6-yl]-2-(1-naphthyl)-ethanesulfonamide

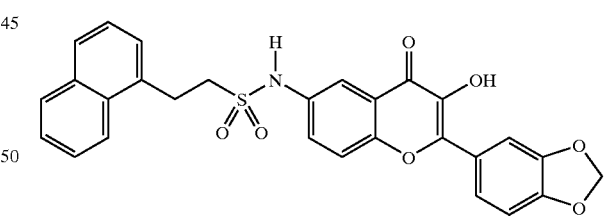

32 mg (Yield 92.6%) of the title compound was obtained according to the same procedure as Example 26 except that 2-(1-naphthyl)-ethanesulfonylchloride was used instead of 4-bromobenzene sulfonylchloride.

$^1$H NMR (DMSO-d$_6$, ppm); δ 10.34 (1H, br s), 9.58 (1H, s), 7.98 (1H, s), 7.90–7.70 (7H, m), 7.50–7.40 (4H, m), 7.13 (1H, d), 6.14 (2H, d), 3.47 (2H, m), 3.30 (2H, m). FAB MS (m/e)=516 [M$^+$+1].

EXAMPLE 31

Synthesis of N-[2-(Benzo[1,3]dioxol-5-yl)-3-hydroxy-4-oxo-4H-chromen-6-yl]-4,5-dibromo-2-thiophenesulfonamide

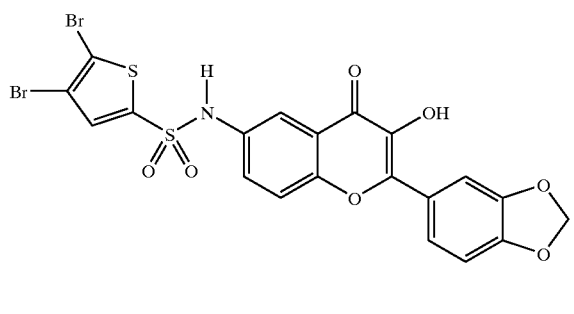

33 mg (Yield 82%) of the title compound was obtained according to the sane procedure as Example 26 except that 4,5-thiopheinesulfonyl chloride was used instead of 4-bromobenzene sulfonylchloride.

$^1$H NMR (DMSO-d$_6$, ppm); δ 9.60 (1H, s), 7.85–7.74 (4H, m), 7.57 (2H, m), 7.12 (1H, s), 6.16 (2H, s). FAB MS (m/e)=602 [M$^+$+1].

EXAMPLE 32

Synthesis of N-[2-(Benzo[1,3]dioxol-5-yl)-3-hydroxy-4-oxo-4H-chromen-6-yl]-[1,1'-biphenyl]-4-sulfonamide

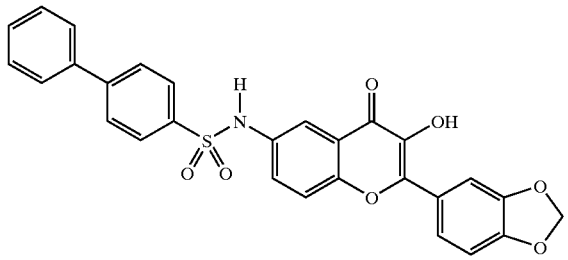

34 mg (Yield 98.8%) of the title compound was obtained according to the same procedure as Example 26 except that 4-biphenyl sulfonylchloride was used instead of 4-bromobenzene sulfonylchloride.

$^1$H NMR (DMSO-d$_6$, ppm); δ 10.67 (1H, br s), 9.56 (1H, s), 8.00–7.47 (14H, m), 7.12 (1H, d), 6.12 (2H, s). FAB MS (m/e)=514 [M$^+$+1].

EXAMPLE 33

Synthesis of N-[2-(Benzo[1,3]dioxol-5-yl)-3-hydroxy-4-oxo-4H-chromen-6-yl]-5-(isooxazolyl)-2-thiophenesulfonamide

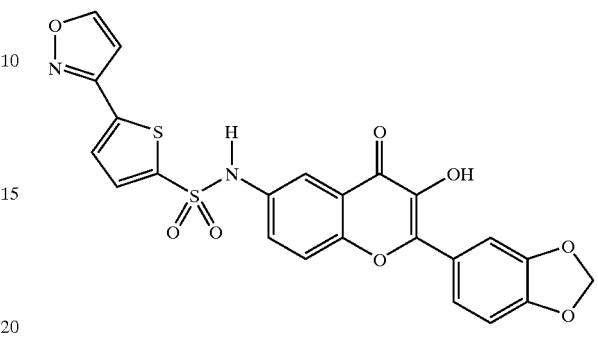

30 mg (Yield 87.7%) of the title compound was obtained according to the same procedure as Example 26 except that 5 (isooxazolyl)-2-thiophenesulfonylchloride was used instead of 4-bromo benzenesulfonylchloride.

$^1$H NMR (DMSO-d$_6$, pp); δ 11.00 (1H, br s), 9.58 (1H, s), 8.70 (1H, s), 7.90–7.50 (7H, m), 7.15–7.07 (2H, m), 6.13 (2H, s). FAB MS (m/e)=511 [M$^+$+1 ].

EXAMPLE 34

Synthesis of N-[2-(Benzo[1,3]dioxol-5-yl)-3-hydroxy-4-oxo-4H-chromen-6-yl]-5-(2-pyridinyl)-2-thiophenesulfonamide

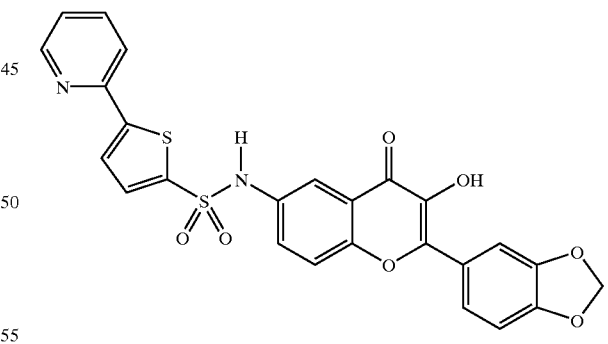

30 mg (Yield 86%) of the title compound was obtained according to the same procedure as Example 26 except that 5-(2-pyridinyl)-2-thiophenesulfonylchloride was used instead of 4-bromo benzenesulfonylchloride.

$^1$H NMR (DMSO-d$_6$, ppm); δ 10.84 (1H, br s), 9.56 (1H, s), 8.53 (1H, s), 8.00–7.70 (7H, m), 7.56 (2H, m), 7.40 (1H, m), 7.11 (1H, m), 6.12 (2H, s). FAB MS (m/e)=521 [M$^+$+1].

EXAMPLE 35

Synthesis of N-[2-(Benzo[1,3]dioxol-5-yl)-3-hydroxy-4-oxo-4H-chromen-6-yl]-3,4-difluorobenzenesulfonamide

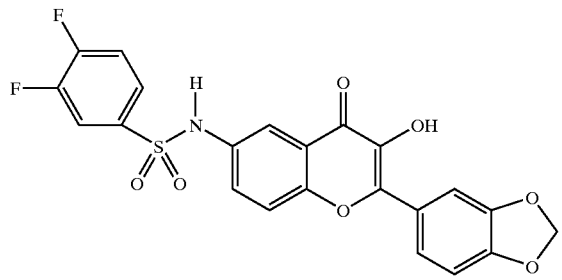

22 mg (Yield 69.4%) of the title compound was obtained according to the same procedure as Example 26 except that 3,4-difluorobenzenesulfonylchloride was used instead of 4-bromobenzene sulfonylchloride.

$^1$H NMR (DMSO-d$_6$, ppm); δ 10.70 (1H, br s), 9.57 (1H, s), 7.82–7.52 (8H, m), 7.11 (1H, d), 6.13 (2H, s). FAB MS (m/e)=474 [M$^+$+1].

EXAMPLE 36

Synthesis of N-[2-(Benzo[1,3]dioxol-5-yl)-3-hydroxy-4-oxo-4H-chromen-6-yl]-4-(trifluoromethyl)benzenesulfonamide

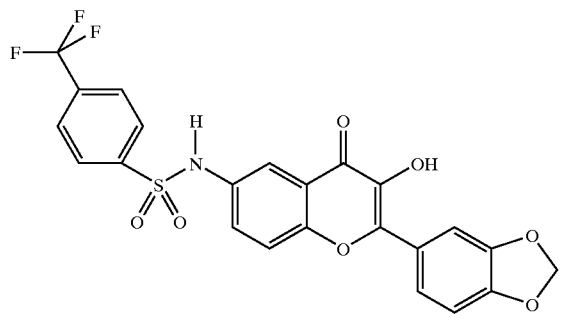

24 mg (Yield 70.8%) of the title compound was obtained according to the same procedure as Example 26 except that 4-(trifluoromethyl)benzenesulfonylchloride was used instead of 4-bromo benzenesulfonylchloride.

$^1$H NMR (DMSO-d$_6$, ppm); δ 10.84 (1H, br s), 9.57 (1H, s), 7.95 (4H, m), 7.79–7.71 (4H, m), 7.52 (1H, d), 7.11 (1H, d), 6.13 (2H, s). FAB MS (m/e)=506 [M$^+$+1].

EXAMPLE 37

Synthesis of N-[2-(Benzo[1,3]dioxol-5-yl)-3-hydroxy-4-oxo-4H-chromen-6-yl]-4-chloro-3-nitrobenzenesulfonamide

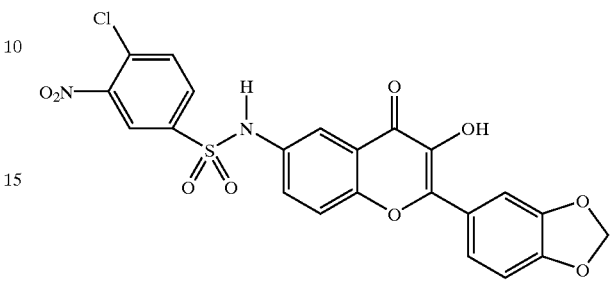

81 mg (Yield 93.4%) of the title compound was obtained according to the same procedure as Example 26 except that 4-chloro-3-nitrobenzenesulfonylchloride and 50 mg (168 pmol) of 6-amino-2-(benzo[1,3]dioxol-5-yl)-3-hydroxy-4H-chromen-4-one were used instead of 4-bromo benzenesulfonylchloride.

$^2$H NMR(DMSO-d$_6$, ppm); δ 10.90 (1H, br s), 9.58 (1H, s), 8.42 (1H, s), 7.95 (2H, m), 7.80–7.70 (4H, m), 7.53 (1H, d), 7.12 (1H, d), 6.12 (2H, s). FAB MS (m/e)=517 [M$^+$+1].

EXAMPLE 38

Synthesis of N-[2-(Benzo[1,3]dioxol-5-yl)-3-hydroxy-4-oxo-4H-chromen-6-yl]-3-chloro-1-propanesulfonamide

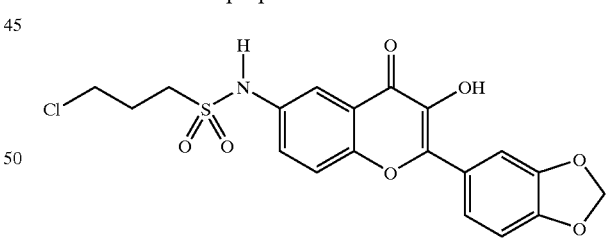

61 mg (Yield 84.4%) of the title compound was obtained according to the same procedure as Example 37 except that 3-chloro-1-propanesulfonylchloride was used instead of 4-chloro-3-nitro benzenesulfonylchloride.

$^1$H NMR (DMSO-d$_6$, ppm); δ 10.21 (1H, br s), 9.58 (1H, s), 7.89 (1H, s), 7.81 (2H, m), 7.75 (1H, s), 7.62 (1H, d), 7.13 (1H, d), 6.13 (2H, s), 3.72 (2H, m), 3.26 (2H, m), 2.12 (2H, m). FAB MS (m/e)=438 [M$^+$+1].

EXAMPLE 39

Synthesis of N-[2-(Benzo[1,3]dioxol-5-yl)-3-hydroxy-4-oxo-4H-chromen-6-yl]-2,4-difluorobenzenesulfonamide

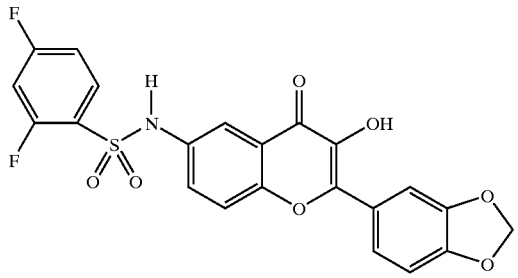

76 mg (Yield 95.2%) of the title compound was obtained according to the same procedure as Example 37 except that 2,4-difluorobenzenesulfonylchloride was used instead of 4-chloro-3-nitro benzenesulfonylchloride.

$^1$H NMR (DMSO-d$_6$, ppm); δ (10.96 (1H, s), 9.54 (1H, s), 7.90 (1H, m), 7.79–7.70 (4H, m), 7.54 (2H, m), 7.25 (1H, m), 7.11 (1, d), 6.12 (2H, s). FAB MS (m/e)=474 [M$^+$+1].

EXAMPLE 40

Synthesis of N-[2-(Benzo[1,3]dioxol-5-yl)-3-hydroxy-4-oxo-4H-chromen-6-yl]-4-fluorobenzenesulfonamide

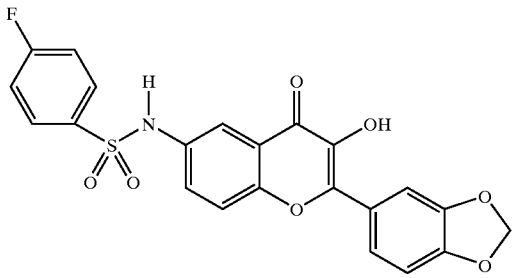

72 mg (Yield 94%) of the title compound was obtained according to the same procedure as Example 37 except that 4-fluorobenzene sulfonylchloride was used instead of 4-chloro-3-nitrobenzenesulfonyl chloride.

$^1$H NMR (DMSO-d$_6$, ppm); δ 10.59 (1H, s), 9.55 (1H, s), 7.79–7.71 (6H, m), 7.50 (1H, d), 7.39 (2H, m), 7.12 (1H, d), 6.12 (2H, s). FAB MS (m/e)=456 [M+−1].

EXAMPLE 41

Synthesis of N-[2-(Benzo[1,3]dioxol-5-yl)-3-hydroxy-4-oxo-4H-chromen-6-yl]-2-(2,2,2-trifluoroacetyl)-1,2,3,4-tetrahydro-7-isoquinolinesulfonamide

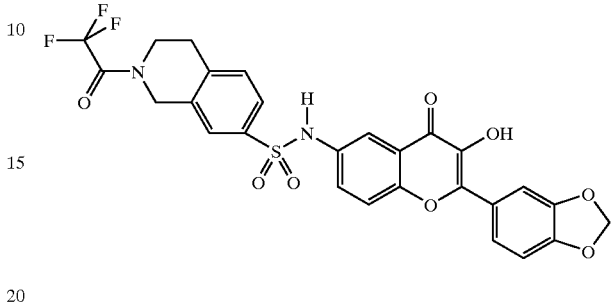

49 mg (Yield 82.4%) of the title compound was obtained according to the same procedure as Example 26 except that 2-(2,2,2-trifluoroacetyl)-1,2,3,4-tetrahydro-7-isoquinolinesulfonylchlonrde and 30 mg (101 pmol) of 6-amino-2-(benzo[1,3]dioxol-5-yl)-3-hydroxy-4H-chromen-4-one were used instead of 4-bromobenzene sulfonylchloride.

$^1$H NMR (DMSO-d$_6$, ppm); δ 10.65 (1H, br s), 9.54 (1H, s), 7.90–7.70 (5H, m), 7.60–7.50 (2H, m), 7.40 (1H, m), 7.11 (1H, d), 6.12 (2H, s), 4.78 (2H, d), 3.76 (2H, d), 2.94 (2H, m). FAB MS (m/e)=589 [M$^+$+1].

EXAMPLE 42

Synthesis of 4-({[2-(Benzo[1,3]dioxol-5-yl)-3-hydroxy-4-oxo-4H-chromen-6y]amino}sulfonyl)benzoic acid

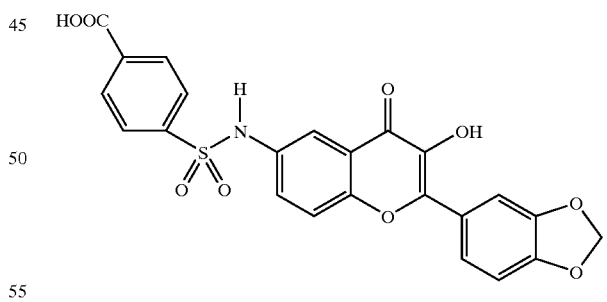

47 mg (Yield 96%) of the title compound was obtained according to the same procedure as Example 41 except that 4-chlorosulfonylbenzoic acid was used instead of 2-(2,2,2-trifluoroacetyl)-1,2,3,4-tetrahydro-7-isoquinolinesulfonylchloride.

$^1$H NMR (DMSO-d$_6$, ppm); δ 10.71 (1H, br s), 9.55 (1H, s), 8.07 (2H, d), 7.86–7.70 (6H, m), 7.52 (1H, d), 7.11 (1H, d), 6.12 (2H, s). FAB MS (m/e)=482 [M$^+$+1].

EXAMPLE 43

Synthesis of N-[2-(Benzo[1,3]dioxol-5-yl)-3-hydroxy-4-oxo-4H-chromen-6-y]1,2,3,4-tetrahydro-7-isoquinolinesulfonamide

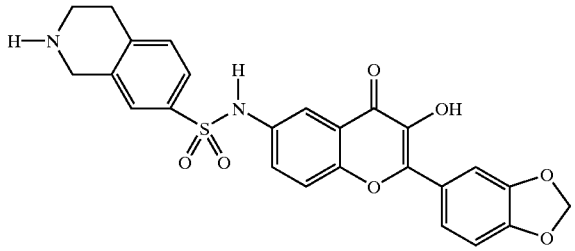

20 mg (34 pmol) of the compound obtained in Example 38 was dissolved in methanol, 0.1 ml of aqueous 1N sodium hydroxiden solution was added thereto, and the mixture was stirred at room temperature for 1 hours. The mixture was concentrated, diltuted with water, acidified with 1N hydrochloric acid, and then neutralized with sodium bicarbonate. The produced solid was filtered, washed with water, and dried to give 14.4 mg of the title compound in a yield of 85.8%.

$^1$H NMR (DMSO-d$_6$, ppm); δ 7.76–7.66 (4H, m), 7.48 (3H, m), 7.23 (1H, d), 7.11 (1H, d), 6.12 (2H, s), 3.85 (2H, m), 2.92 (2H, m), 2.70 (2H, m). FAB MS (m/e)=493 [M$^+$+1].

EXAMPLE 44

Synthesis of N-[2-(Benzo[1,3]dioxol-5-yl)-3-hydroxy-4-oxo-4H-chromen-6-yl]-N'-cyclohexylsulfamide

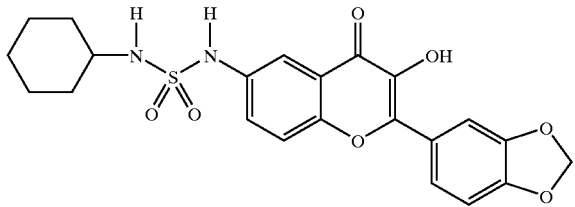

30 mg (101 pmol) of 6-amino-2-(benzo[1,3]dioxol-5-yl)-3-hydroxy-4H-chromen-4-one obtained in Example 24 was dissolved in 3 ml of pyridine, and the mixture was reacted with excess amount of cyclohexylamino sulfonylchloride at room temperature for 15 hours. After the reaction was completed, the resulting product was diluted with 10 ml of water. The produced solid was filtered, washed with water and ethylether, and then dried to give 6 mg of the title compound in a yield of 13%.

$^1$H NMR (DMSO-d$_6$, ppm); δ 7.82–7.55 (5H, m), 7.13 (1H, d), 6.13 (2H, s), 3.15 (1H, m), 1.67–1.40 (4H, m), 1.20–1.05 (6H, m). FAB MS (m/e)=459 [M$^+$].

EXAMPLE 45

Synthesis of N-[2-(Benzo[1,3]dioxol-5-yl)-3-hydroxy-4-oxo-4H-chromen-6-yl]-4-(4-morpholinyl)-3-nitrobenzenesulfonamide

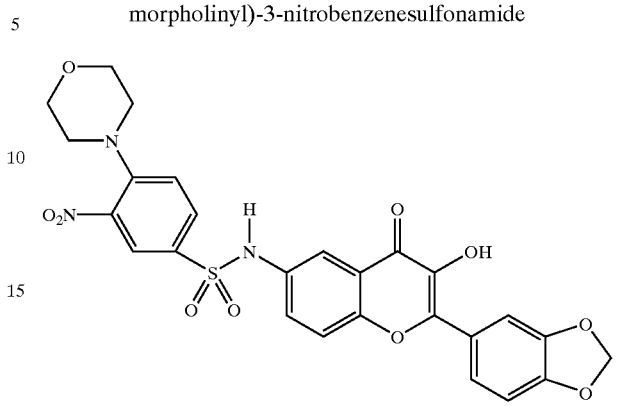

10 mg (19.3 pmol) of the compound obtained in Example 37, excess amount of morpholine and potassium carbonate were introduced into 5 ml of acetonitrile, and boiled for 4 hours. The mixture was cooled to room temperature, and ethylether was added thereto. The mixture was stirred for 10 minutes. The produced solid was filtered, washed with water and ethylether, and then dried to give 5 mg of the title compound in a yield of 45.5%.

$^1$H NMR (DMSO-d$_6$, ppm); δ 10.60 (1H, br s), 9.55 (1H, br s), 8.16 (1H, s), 7.80–7.70 (5H, m), 7.53 (1H, d), 7.36 (1H, d), 7.11 (1H, d), 6.12 (2H, s), 3.64 (4H, m), 3.10 (4H, m). FAB MS (m/e)=568 [M$^+$+1].

EXAMPLE 46

Synthesis of N-[2-(Benzo[1,3]dioxol-5-yl)-3-hydroxy-4-oxo-4H-chromen-6-yl]-4-(4-methyl-1-piperazinyl)-3-nitrobenzenesulfonamide

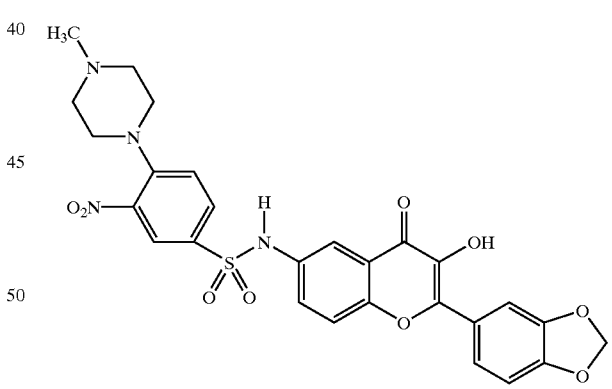

20 mg (38.7 pmol) of the compound obtained in Example 37, excess amount of N-methylpiperazine and potassium carbonate were introduced into 5 ml of acetonitrile, and boiled for 4 hours. The mixture was cooled to room temperature, concentrated under reduced pressure, dissolved in 10% methanol/methylenechloride, and then filtered through silica gel pad. The filtrate was concentrated to give 4.5 mg of the title compound in a yield of 20%.

$^1$H NMR (DMSO-d$_6$, ppm); δ 89.50 (1H, br s), 8.13 (1H, s), 7.79–7.70 (5H, m), 7.52 (1H, m), 7.35 (1H, d), 7.11 (1H, d), 6.12 (2H, s), 3.10 (4H, m), 2.36 (4H, m), 2.17 (3H, s). FAB MS (m/e)=581 [M$^+$+1].

EXAMPLE 47

Synthesis of N-[2-(Benzo[1,3]dioxol-5-yl)-3-hydroxy-4-oxo-4H-chromen-6-yl]-benzamide

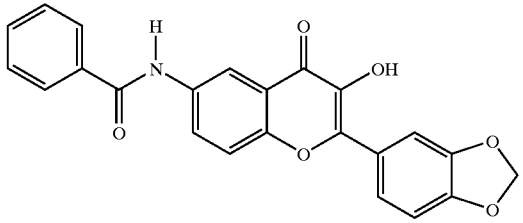

30 mg (101 pmol) of 6-amino-2-(benzo[1,3]dioxol-5-yl)-3-hydroxy-4H-chromen-4-one obtained in Example 24 was dissolved in 2 ml of methylenechloride, and the mixture was reacted with 10 molar equivalents of benzoylchloride and excess amount of potassium carbonate at room temperature for 10 hours. The resulting product was filtered, washed with methylenechloride and water, and dried to give 32 mg of the title compound in a yield of 79%.

$^1$H NMR (DMSO-$d_6$, ppm); δ 10.54 (1H, s), 9.55 (1H, br s), 8.61 (1H, s), 8.17 (1H, d), 8.02 (2H, d), 7.85–7.78 (3H, m), 7.62–7.55 (2H, m) 7.14 (1H, d), 6.14 (2H, s); FAB MS (m/e)=402 [M$^+$+1].

EXAMPLE 48

Synthesis of N-[2-(Benzo[1,3]dioxol-5-yl)-3-hydroxy-4-oxo-4H-chromen-6-yl]-4-chlorobenzamide

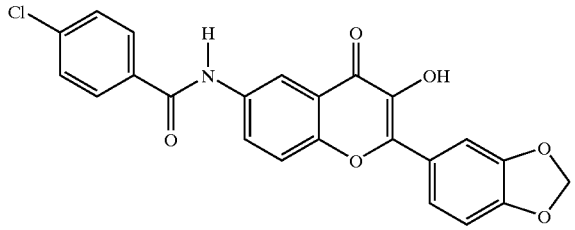

43.5 mg (Yield 99%) of the title compound was obtained according to the same procedure as Example 47 except that 4-chloro benzoylchloride was used instead of benzoylchloride.

$^1$H NMR (DMSO-d, ppm); δ 10.63 (1H, br s), 9.61 (1H, br s), 8.59 (1H, s), 8.15 (1H, d), 8.05 (2H, d), 8.90–8.70 (3H, m), 7.65 (2H, d), 7.14 (1H, s), 6.14 (2H, s); FAB MS (m/e)=436 [M$^+$+1].

EXAMPLE 49

Synthesis of N-[2-(Benzo[1,3]dioxol-5-yl)-3-hydroxy-4-oxo-4H-chromen-6-yl]3-N'-benzylurea

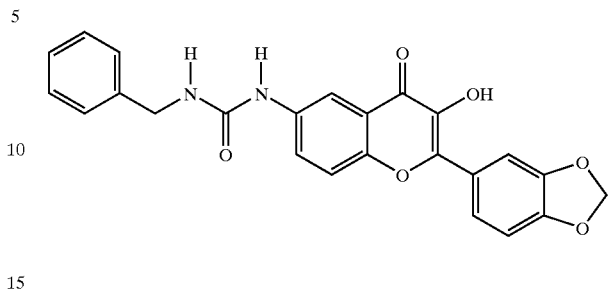

30 mg (101 pmol) of 6-amino-2-(benzo[1,3]dioxol-5-yl)-3-hydroxy-4H-chromen-4-one and 1.5 molar equivalents of benzylisocyanate were stirred in 3 ml of methylenechloride at room temperature for 15 hours. The resulting product was filtered, washed with methylenechloride, and then dried to give 35.9 mg of the title compound in a yield of 82.5%.

$^1$H NMR (DMSO-$d_6$, ppm); δ 9.40 (1H, br s), 8.96 (1H, s), 8.24 (1H, s), 7.85–7.65 (4H, m), 7.34 (2H, m) 7.25 (1H, m), 7.12 (1H, d), 6.80 (1H, m), 6.13 (2H, s), 4.33 (2H, d). FAB MS (m/e)=431 [M$^+$+1].

EXAMPLE 50

Synthesis of N-[2-(Benzo[1,3]dioxol-5-yl)-3-hydroxy-4-oxo-4H-chromen-6-yl]-N'-(4-bromophenyl)urea

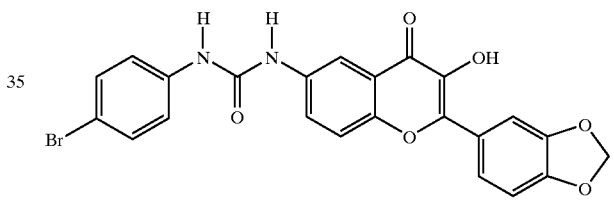

34.8 mg (Yield 69.6%) of the title compound was obtained according to the same procedure as Example 49 except that 4-bromophenylisocyanate was used instead of benzylisocyanate.

$^1$H NMR (DMSO-$d_6$, ppm); δ 7.78 (1H, d), 7.72 (1H, s), 7.55–7.40 (4H, m), 7.20–7.05 (4H, m), 6.13 (2H, s). FAB MS (m/e)=496 [M$^+$+1].

EXAMPLE 51

Synthesis of N-[2-(Benzo[1,3]dioxol-5-yl)-3-hydroxy-4-oxo-4H-chromen-6-yl]-N'-phenylurea

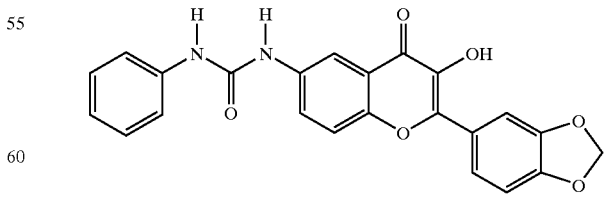

28.5 mg (Yield 67.8%) of the title compound was obtained according to the same procedure as Example 49 except that phenylisocyanate was used instead of benzylisocyanate.

¹H NMR (DMSO-d₆, ppm); δ 9.10 (1H, s), 8.80 (1H, s), 8.31 (1H, s), 7.84 (1H, d), 7.77 (1H, s), 7.72 (2H, s), 7.49 (1H, d), 7.29 (2H, m), 7.13 (1H, d), 6.98 (1H, d), 6.14 (2H, s). FAB MS (m/e)=417 [M⁺+1].

EXAMPLE 52

Synthesis of N-[2-(Benzo[1,3dioxol-5-yl)-3-hydroxy-4-oxo-4H-chromen-6-yl]-N'-benzoylurea

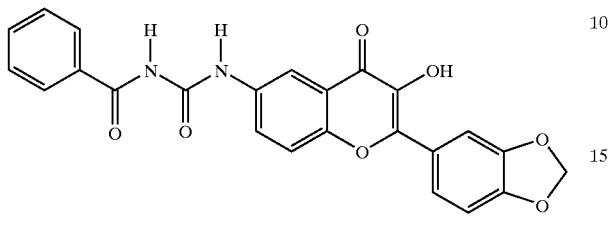

36 mg (Yield 80%) of the title compound was obtained according to the same procedure as Example 49 except that benzoylisocyanate was used instead of benzylisocyanate.

¹H NMR (DMSO-d₄, ppm); δ 11.1 (1H, s), 11.0 (1H, s), 9.55 (1H, s), 8.42 (1H, m), 8.04 (2H, m), 7.88–7.56 (6H, m), 7.13 (2H, m), 6.14 (2H, s). FAB MS (m/e)=445 [M⁺+1].

EXAMPLE 53

Synthesis of N-[2-(Benzo[1,3]dioxol-5-yl)-3-hydroxy-4-oxo-4H-chromen-6-yl]-N'-(3-bromophenyl)urea

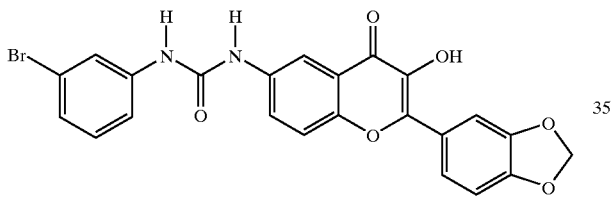

36 mg (Yield 72%) of the title compound was obtained according to the same procedure as Example 49 except that 3-bromophenyl isocyanate was used instead of benzylisocyanate.

¹H NMR (DMSO-d₆, ppm); δ 9.50 (1H, br s), 9.09 (1H, s), 8.97 (1H, s), 8.30 (1H, s), 7.88 (1H, s), 7.82 (1H, d), 7.76 (1H, s), 7.73 (2H, s), 7.34 (1H, d), 7.25 (1H, t), 7.18 (1H, d), 7.12 (1H, d), 6.14 (1H, s). FAB MS (m/e)=496 [M⁺+1].

EXAMPLE 54

Synthesis of N-[2-(Benzo[1,3]dioxol-5-yl)-3-hydroxy-4-oxo-4H-chromen-6-yl]-N'-(2,4-dichlorophenyl)urea

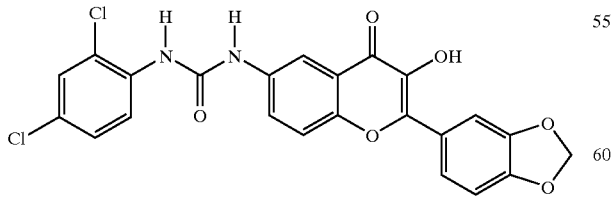

39 mg (Yield 79.6%) of the title compound was obtained according to the same procedure as Example 49 except that 2,4-dichlorophenylisocyanate was used instead of benzylisocyanate.

¹H NMR (DMSO-d₆, ppm); δ 9.75 (1H, s), 9.50 (1H, br s), 8.44 (1H, s), 8.34 (1H, s), 8.23 (1H, d), 7.84–7.65 (5H, m), 7.42 (1H, d), 7.13 (1H, d), 6.14 (2H, s). FAB MS (m/e)=486 [M⁺+1].

EXAMPLE 55

Synthesis of N-[2-(Benzo[1,3]dioxol-5-yl)-3-hydroxy-4-oxo-4H-chromen-6-yl]-N'-(3-cyanophenyl)urea

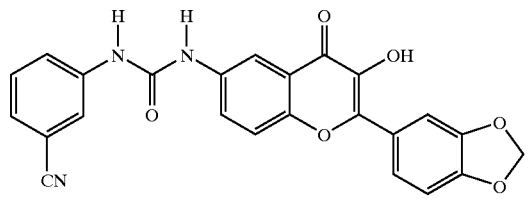

40mg (Yield 89.6%) of the title compound was obtained according to the same procedure as Example 49 except that 3-cyanophenylisocyanate was used instead of benzylisocyanate.

¹H NMR (DMSO-d₆, ppm); δ 9.56 (1H, s), 9.15 (1H, s), 8.32 (1H, s), 8.01 (1H, m), 7.84 (1H, d), 7.80–7.45 (6H, m), 7.14 (1H, d), 6.14 (2H, s). FAB MS (m/e)=442 [M⁺+1].

EXAMPLE 56

Synthesis of N-[2-(Benzo[1,3]dioxol-5-yl)-3-hydroxy-4-oxo-4H-chromen-6-yl]-N'-(4-nitrophenyl)urea

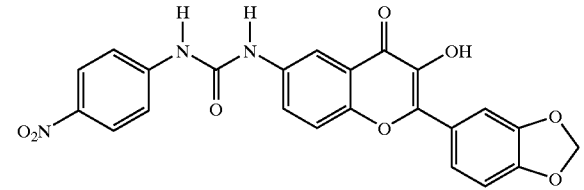

37.5 mg (Yield 80.5%) of the title compound was obtained according to the same procedure as Example 49 except that 4-nitrophenylisocyanate was used instead of benzylisocyanate.

¹H NMR (DMSO-d₆, ppm); δ 9.57 (1H, s), 9.53 (1H, s), 8.33 (1H, s), 8.21 (2H, m), 7.82–7.74 (6H, m), 7.13 (1H, d), 6.14 (2H, s). FAB MS (m/e)=462 [M⁺+1].

EXAMPLE 57

Synthesis of 6-Chloro-2-(3,4-dihydroxyphenyl)-3-hydroxy-4H-chromen-4-one (Compound 12)

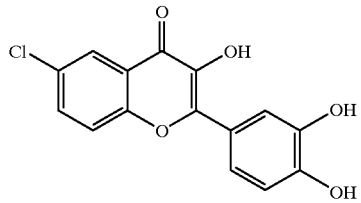

10 mg (31.6 pmol) of the compound obtained in Example 12 was dissolved in 2 ml of methylenechloride, 3 molar equivalents of boron tribromide (BBr₃) was added thereto, and then the mixture was stirred at room temperature for 2 hours. The remained boron tribromide (BBr₃) was decomposed with methanol. The residue was concentrated under reduced pressure, and purified by preparative TLC to give 7 mg of the title compound in a yield of 72%.

$^1$H NMR (MeOH-$d_4$, ppm); δ 8.09 (1H, s), 7.80 (1H, s), 7.70 (3H, m), 6.90 (1H, d); FAB MS (m/e)=305 [M$^+$+1].

EXAMPLE 58

Synthesis of 6-Bromo-2-(3,4-dihydroxyphenyl)-3-hydroxy-4H-chromen-4one (Compound 13)

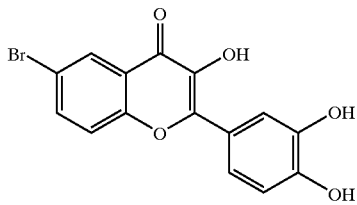

7.8 mg (Yield 16%) of the title compound was obtained according to the same procedure as Example 57 except that 50 mg (138 pmol) of the compound obtained in Example 13 was used instead of the compound obtained in Example 12.

$^1$H NMR (MeOH-$d_4$, ppm); δ 8.26 (1H, s), 7.83 (1H, d), 7.80 (1H, s), 7.72 (1H, d), 7.60 (1H, d), 6.91 (1H, d); FAB MS (m/e)=350 [M$^+$+1].

EXAMPLE 59

Synthesis of 2-(3,4-Dihydroxyphenyl)-3,6-dihydroxy-4H-chromen-4-one (Compound 14)

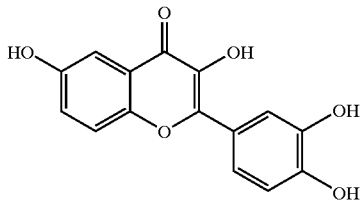

The reaction was conducted according to the same procedure as Example 57 except that 50 mg (159 pmol) of the compound obtained in Example 5 instead of the compound obtained in Example 12 and 5.0 molar equivalents of boron tribromide (BBr₃) were used. Then the resulting product was separated by preparative TLC to give 23 mg of the title compound in a yield of 51%.

$^1$H NMR (DMSO-$d_6$, ppm); δ 7.47–6.48 (6H, m); FAB MS (m/e)=287 [M$^+$+1].

EXAMPLE 60

Synthesis of 6-Amino-2-(3,4-dihydroxyphenyl)-3-hydroxy-4H-chromen-4-one (Compound 15)

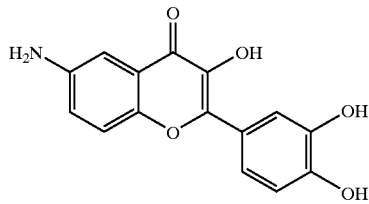

The reaction was conducted according to the same procedure as Example 57 except that 10 mg (5 pmol) of the compound obtained in Preparation 35 was used instead of the compound obtained in Example 12. The resulting product was concentrated, and the solid was produced from 10% methanol/methylenechloride solution. The produced solid was filtered to give 9.5 mg of the title compound in a yield of 99%.

$^1$H NMR (MeOH-$d_4$, ppm); δ 8.11 (1H, s), 7.85–7.82 (2H, m), 7.75–7.67 (2H, m), 7.62 (1H, d); FAB MS (m/e)=286 [M$^+$+1].

EXAMPLE 61

Synthesis of 2-(3,4-Dihydroxyphenyl)-3-hydroxy-6-methoxy-4H-chromen-4-one (Compound 16)

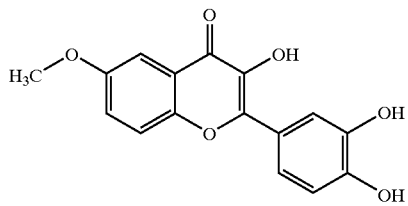

The reaction was conducted according to the same procedure as Example 57 except that 50 mg (159 pmol) of the compound obtained in Example 5 instead of the compound obtained in Example 12 and 1.5 molar equivalents of boron tribromide (BBr₃) were used. Then the resulting product was separated by preparative TLC to give 28 mg of the title compound in a yield of 60%.

$^1$H NMR (MeOH-$d_4$, ppm); δ 7.78 (1H, m), 7.65 (1H, m), 7.50 (2H, m), 6.91 (1H, m), 6.80 (1H, m), 3.90 (3H, s); FAB MS (m/e)=301 [M$^+$+1].

EXAMPLE 62

Synthesis of 6-Fluoro-2-(3,4-dihydroxyphenyl)-3-hydroxy-4H-chromen-4-one (Compound 17)

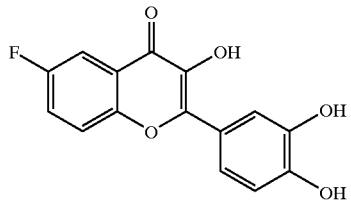

40 mg (Yield 83%) of the title compound was obtained according to the same procedure as Example 57 except that 50 mg (166 pmol) of the compound obtained in Example 14 was used instead of the compound obtained in Example 12.

$^1$H NMR (MeOH-d$_4$, ppm); δ 8.26 (1H, d), 7.83 (1H, t), 7.80 (1H, s), 7.72 (1H, d), 7.60 (1H, d), 6.91 (1H, d); FAB MS (m/e)=289 [M$^+$+1].

EXAMPLE 63

Synthesis of 6-Methyl-2-(3,4-dihydroxyphenyl)-3-hydroxy-4f1-chromen-4-one (Compound 18)

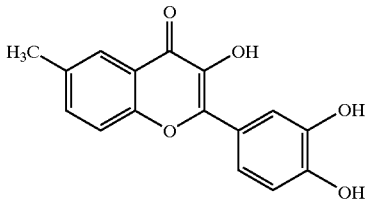

40 mg (Yield 83%) of the tide compound was obtained according to the same procedure as Example 57 except that 50 mg (168 pmol) of the compound obtained in Example 15 was used instead of the compound obtained in Example 12.

$^1$H NMR (MeOH-d$_4$, ppm); δ 8.02 (1H, s), 7.63 (1H, d), 7.80 (1H, s), 7.72 (1H, d), 7.60 (1H, d), 6.91 (1H, d), 2.54 (3H, s); FAB MS (m/e)=285 [M$^+$+1].

EXAMPLE 64

Synthesis of 6,8-Dichloro-2-(3,4-dihydroxyphenyl)-3-hydroxy-4H-chromen-4-one (Compound 19)

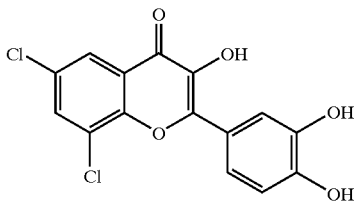

20 mg (Yield 69%) of the title compound was obtained according to the same procedure as Example 57 except that 30 mg (85 pmol) of the compound obtained in Example 16 was used instead of the compound obtained in Example 12.

$^1$H NMR (DMSO-d$_6$, ppm); δ 9.76 (1H, s), 9.72 (1H, s), 9.36 (1H, s), 8.33 (1H, s), 8.15 (1, s), 7.83 (1H, s), 7.68 (1H, d), 6.93 (1H, d); FAB MS (m/e)=339 [M$^+$+1].

EXAMPLE 65

Synthesis of 6,8-Dibromo-2-(3,4-dihydroxyphenyl)-3-hydroxy-4H-chromen-4-one (Compound 20)

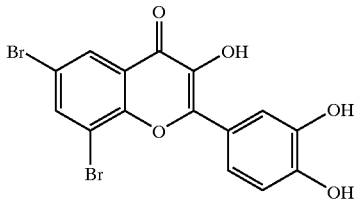

22.8 mg (Yield 78%) of the title compound was obtained according to the same procedure as Example 57 except that 30 mg (68 pmol) of the compound obtained in Example 17 was used instead of the compound obtained in Example 12.

$^1$H NMR (DMSO-d$_6$, ppm); δ 9.75 (1H, s), 9.69 (1H, s), 9.36 (1H, s), 8.33 (1H, s), 8.15 (1H, s), 7.83 (1H, s), 7.68 (1H, d), 6.93 (1H, d); FAB MS (m/e)=429 [M$^+$+1].

EXAMPLE 66

Synthesis of 6,8-Difluoro-2-(3,4-dihydroxyplenyl)-3-hydroxy-4H-chromen-4-one (Compound 21)

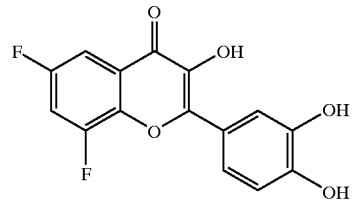

25 mg (Yield 86%) of the title compound was obtained according to the same procedure as Example 57 except that 30 mg (94 pmol) of the compound obtained in Example 18 was used instead of the compound obtained in Example 12.

$^1$H NMR (DN4SO-d$_6$, ppm); δ (9.75 (1H, s), 9.69 (]H, s), 9.36 (1H, s), 8.33 (1H, s), 8.15 (1H, s), 7.83 (1H, s), 7.68 (1H, d), 6.93 (1H, d); FAB MS (m/e)=307 [M$^+$+1].

EXAMPLE 67

Synthesis of 6Chloro-2-(3,4-dihydroxyphenyl)-3-hydroxy-7-methyl-4H-chromen-4-one (Compound 22)

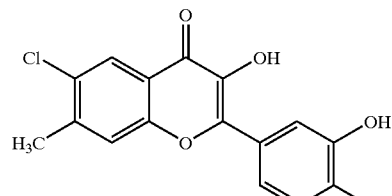

21.0 mg (Yield 73%) of the title compound was obtained according to the same procedure as Example 57 except that 30 mg (91 pmol) of the compound obtained in Example 19 was used instead of the compound obtained in Example 12.

$^1$H NMR (MeOH-d$_4$, ppm); δ 8.07 (1H, s), 7.79 (1H, s), 7.70 (1H, d), 7.61 (1H, s), 6.90 (1H, d), 2.52 (3H, s); FAB MS (m/e)=319 [M$^+$+1].

EXAMPLE 68

Synthesis of 2-(3,4-Dihydroxyphenyl)-3-hydroxy-7-methoxy-4H-chromen-4-one (Compound 23)

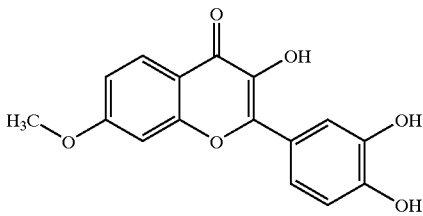

The reaction was conducted according to the same procedure as Example 57 except that 50mg (159 pmol) of the compound obtained in Example 6 instead of the compound obtained in Example 12 and 1.5 molar equivalents of boron tribromide (BBr$_3$) were used. Then the resulting product was separated by preparative TLC to give 28 mg of the title compound in a yield of 60%.

$^1$H NMR (MeOH-d$_4$, ppm); δ 7.78 (1H, m), 7.65 (1H, m), 7.50 (2H, m), 6.91 (1H, m), 6.80 (1H, m), 3.90 (3H, s); FAB MS (m/e)=301 [M$^+$+1].

EXAMPLE 69

Synthesis of 2-(3,4-Dihydroxyphenyl)-3,8-dihydroxy-7-methoxy-4H-chromen-4-one (Compound 24)

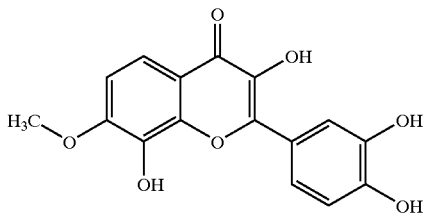

15 mg (Yield 54%) of the title compound was obtained according to the same procedure as Example 57 except that 30 mg (87 pmol) of the compound obtained in Example 20 was used instead of the compound obtained in Example 12.

$^1$H NMR (MeOH-d$_4$, ppm); δ 8.07 (1H, s), 7.79 (1H, s), 7.70 (1H, d), 7.61 (1H, s), 6.90 (1H, d), 3.84 (3H, s); FAB MS (m/e)=317 [M$^+$+1].

EXAMPLE 70

Synthesis of 2-(3,4-Dihydroxyphenyl)-3,8-dihydroxy-4H-chromen-4-one (Compound 25)

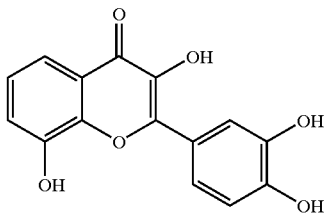

16 mg (Yield 58%) of the title compound was obtained according to the same procedure as Example 57 except that 30 mg (96 pmol) of the compound obtained in Example 21 was used instead of the compound obtained in Example 12.

$^1$H NMR (MeOH-d$_4$, ppm); δ 8.07 (1H, s), 7.79 (1H, s), 7.70 (1H, d), 7.61 (1H, s), 7.54 (1H, m), 6.90 (1H, d); FAB MS (m/e)=287 [M$^+$+1].

EXAMPLE 71

Synthesis of 2-(3,4-Dihydroxyphenyl)-6,7-dimethyl-3-hydroxy-4H-chromen-4one (Compound 26)

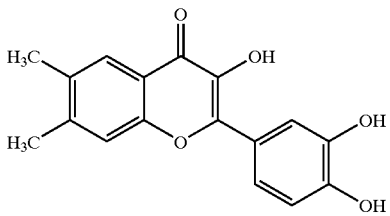

25 mg (Yield 86%) of the title compound was obtained according to the same procedure as Example 57 except that 30 mg (96 pmol) of the compound obtained in Example 22 was used instead of the compound obtained in Example 12.

$^1$H NMR (MeOH-d$_4$, ppm); δ 8.07 (1H, s), 7.79 (1H, s), 7.70 (1H, d), 7.61 (1H, s), 6.90 (1H, d), 2.52 (6H, s); FAB MS (m/e)=299 [M$^+$+1].

EXAMPLE 72

Synthesis of 2-(3,4-Dihydroxyphenyl)-3-hydroxy-5-methoxy-4H-chromen-4-one (Compound 27)

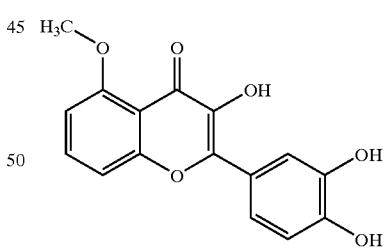

The reaction was conducted according to the same procedure as Example 57 except that 60 mg (190 pmol) of the compound obtained in Example 4 instead of the compound obtained in Example 12 and 1.5 molar equivalents of boron tribromide (BBr$_3$) were used. Then the resulting product was separated by preparative TLC to give 23 mg of the title compound in a yield of 40%.

$^1$H NMR (d$_6$-DMSO, ppm); δ 6 7.71–6.47 (m, 6H), 3.91 (s, 3H); FAB MS (m/e)=301 [M$^+$+1].

EXAMPLE 73

Synthesis of N-[2-(3,4-Dihydroxyphenyl)-3-hydroxy-4-oxo-4H-chromen-6-yl]-4-methylbenzenesulfonamide (Compound 28)

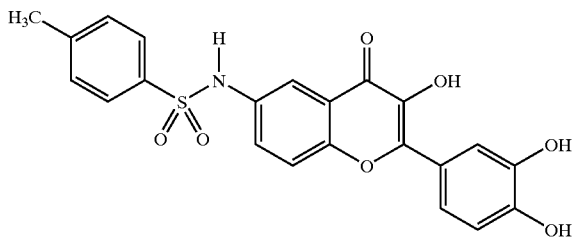

20 mg (44.3 pmol) of the compound obtained in Example 25 was reacted with excess amount of boron tribromide (BBr$_3$) in 3 ml of methylene chloride at room temperature for 3 hours. After the reaction was completed, the resulting product was concentrated under reduced pressure, and then was separated by preparative TLC using 10% methanol/methylenechloride solvent to give 2.8 mg of the title compound in a yield of 14.3%.

$^1$H NMR (MeOH-d$_4$, ppm); δ 7.75–7.48 (7H, m), 7.21 (2H, d), 6.90 (1H, d), 2.32 (3H, s). FAB MS (m/e)=440 [M$^+$+1].

EXAMPLE 74

Synthesis of 4-Bromo-N-[2-(3,4-dihydroxyphenyl)-3-hydroxy-4-oxo-4H-chromen-6-yl]benzenesulfonamide (Compound 29)

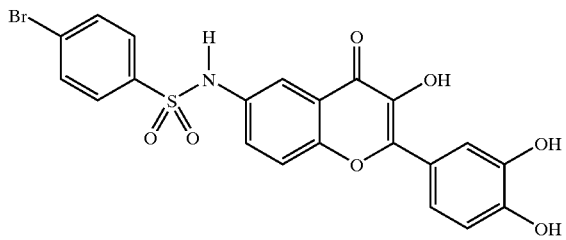

14 mg (Yield 71.5%) of the title compound was obtained according to the same procedure as Example 73 except that 20 mg (38.7 pmol) of the compound obtained in Example 26 was used instead of the compound obtained in Example 25.

$^1$H NMR (DMSO-d$_6$, ppm); δ 7.73 (2H, m), 7.57 (3H, m), 7.46 (2H, m), 6.89 (2H, m). FAB MS (m/e)=505 [M$^+$+1].

EXAMPLE 75

Synthesis of 3-Bromo-N-[2-(3,4-dihydroxyphenyl)-3-hydroxy-4-oxo-4H-chromen-6-yl]benzenesulfonamide (Compound 30)

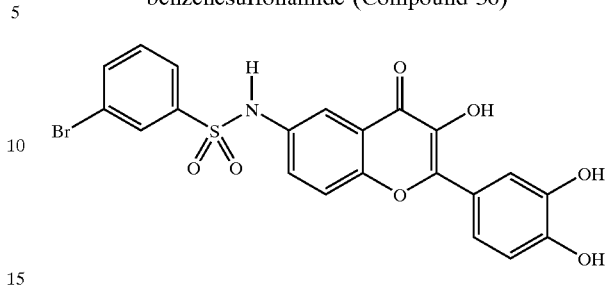

16 mg (Yield 54.5%) of the title compound was obtained according to the same procedure as Example 73 using 30 mg (58.1 pmol) of the compound obtained in Example 27.

$^1$H NMR (MeOH-d$_4$, ppm); δ 7.92 (1H, s), 7.78–7.67 (5H, m), 7.59 (1H, m), 7.54 (1H, m), 7.39 (1H, m), 6.89 (1H, d). FAB MS (m/e)=517 [M$^+$+1].

EXAMPLE 76

Synthesis of N-[2-(3,4-Dihydroxyphenyl)-3-hydroxy-4-oxo-4H-chromen-6-yl]-2-naphthalenesulfonamide (Compound 31)

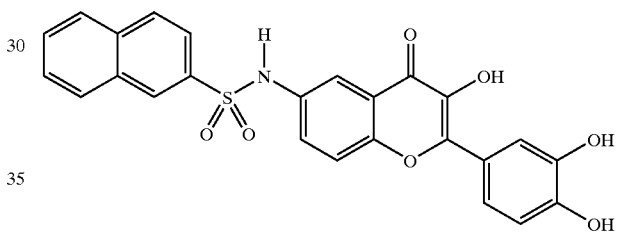

11 mg (Yield 41.7%) of the title compound was obtained according to the same procedure as Example 73 using 27 mg (55.4 pmol) of the compound obtained in Example 28.

$^1$H NMR (MeOH-d$_4$, ppm); δ 8.37 (1H, s), 7.96–7.53 (11H, m), 6.87 (1H, d). FAB MS (m/e)=476 [M$^+$+1].

EXAMPLE 77

Synthesis of N-[2-(3,4-Dihydroxyphenyl)-3-hydroxy-4-oxo-4H-chromen-6-yl]-5-(dimethylamino)-1-naphthalenesulfonamide (Compound 32)

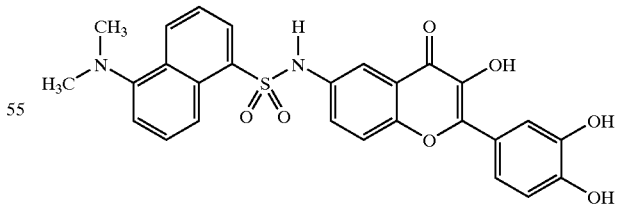

11 mg (Yield 51%) of the title compound was obtained according to the same procedure as Example 73 using 22 mg (41.5 pmol) of the compound obtained in Example 29.

$^1$H NMR (MeOH-d$_4$, ppm); δ 8.49 (1H, d), 8.42 (1H, d), 8.24 (1H, d), 7.73–7.59 (4H, m), 7.47–7.41 (3H, m), 7.25 (1H, d), 6.86 (1H, d), 2.81 (6H, s). FAB MS (m/e)=519 [M$^+$+1].

EXAMPLE 78

Synthesis of N-[2-(3,4-Dihydroxyphenyl)-3-hydroxy-4-oxo-4H-chromen-6-yl]-2-(1-naphthyl)-1-ethanesulfonamide (Compound 33)

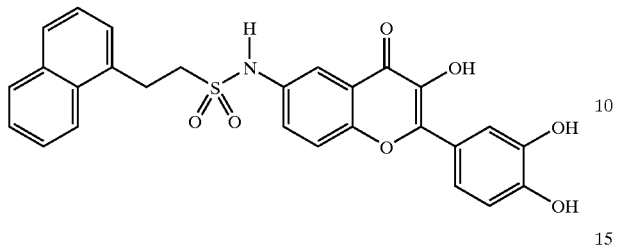

9 mg (Yield 28.8%) of the title compound was obtained according to the same procedure as Example 73 using 32 mg (62 pmol) of the compound obtained in Example 30.

$^1$H NMR (MeOH-d$_4$, ppm); δ 7.96 (1H, s), 7.81–7.71 (5H, m), 7.61 (2H, s), 7.36 (4H, m), 6.91 (1H, d), 3.55–3.50 (4H, m). FAB MS (m/e)=504 [M$^+$+1].

EXAMPLE 79

Synthesis of 4,5-Dibromo-N-[2-(3,4-dihydroxyphenyl)-3-hydroxy-4-oxo-4H-chromen-6-yl]-2-thiophenesulfonamide (Compound 34)

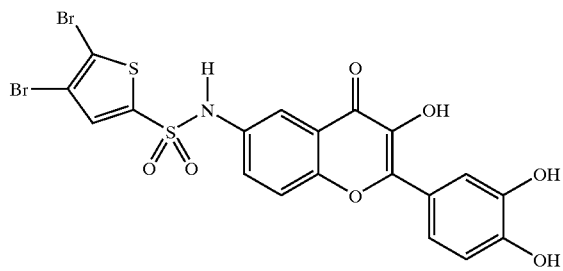

10 mg (Yield 50.9%) of the title compound was obtained according to the same procedure as Example 73 using 20 mg (33.2 pmol) of the compound obtained in Example 31.

$^1$H NMR (DMSO-d$_6$, ppm); δ 11.00 (H, br s), 9.40 (1H, br s), 7.79 (1H, s), 7.71 (2H, m), 7.59–7.53 (3H, m), 6.89 (1H, d). FAB MS (m/e)=590 [M$^+$+1].

EXAMPLE 80

Synthesis of N-[2-(3,4-Dihydroxyphenyl)-3-hydroxy-4-oxo-4H-chromen-6-yl]-[1,1'-biphenyl]-4-sulfonamide (Compound 35)

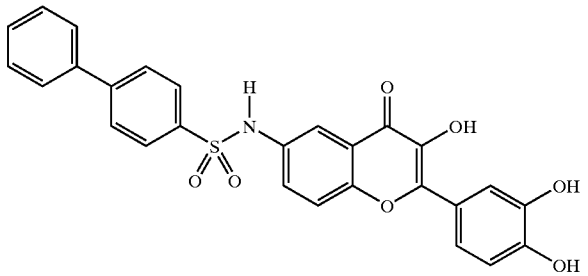

7.2 mg (Yield 21%) of the title compound was obtained according to the same procedure as Example 73 using 35 mg (68.2 pmol) of the compound obtained in Example 32.

$^1$H NMR (DMSO-d$_6$, ppm); δ 10.63 (1H, br s), 9.60 (1H, br s), 9.28 (2H, br s), 7.84–7.40 (1H, m), 6.87 (1H, d). FAB MS (m/e)=502 [M$^+$$_{+1}$].

EXAMPLE 81

Synthesis of N-[2-(3,4-Dihydroxyphenyl)-3-hydroxy-4-oxo-4H-chromen-6-yl]-5-(isooxazolyl)-2-thiophenesulfonamide (Compound 36)

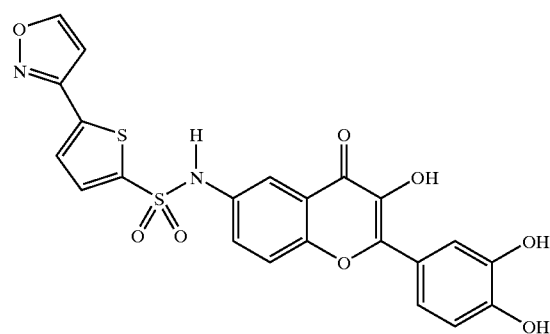

18.7 mg (Yield 66%) of the title compound was obtained according to the same procedure as Example 73 using 29 mg (56.8 pmol) of the compound obtained in Example 33

$^1$H NMR (DMSO-d$_6$, ppm); δ 10.93 (1H, br s) 9.58 (1H, br s), 9.32 (1H, br s), 8.70 (1H, s), 7.84 (1H, s), 7.68 (3H, m), 7.60–7.50 (3H, m), 7.07 (1H, s), 6.88 (1H, d). FAB MS (m/e)=499 [M$^+$+1].

EXAMPLE 82

Synthesis of N-[2-(3,4-Dihydroxyphenyl)-3-hydroxy-4-oxo-4H-chromen-6-yl]-5-(2-pyridinyl)-2-thiophenesulfonamide (Compound 37)

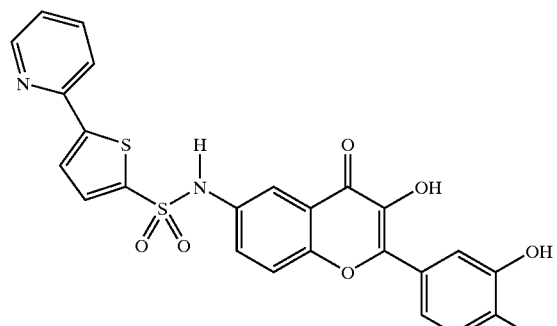

29 mg (Yield 99%) of the title compound was obtained according to the same procedure as Example 73 using 30 mg (57.6 pmol) of the compound obtained in Example 34.

$^1$H NMR (DMSO-d$_6$, ppm); δ 10.80 (1H, s), 8.53 (1H, d), 7.98 (1H, d), 7.87 (2H, m), 7.77 (1H, d), 7.69 (2H, m), 7.55 (3H, m), 7.38 (1H, m), 6.88 (1H, m). FAB MS (m/e)=509 [M$^+$+1].

EXAMPLE 83

Synthesis of N-[2-(3,4-Dihydroxyphenyl)-3-hydroxy-4-oxo-4H-chromen-6-yl]-3,4-difluorobenzenesulfonamide (Compound 38)

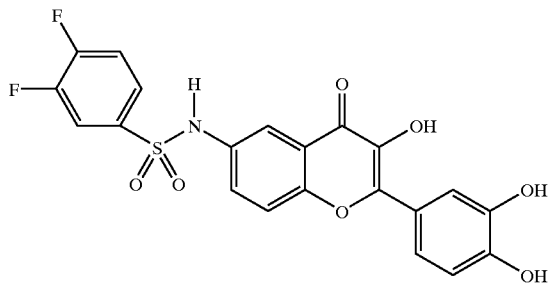

11.4 mg (Yield 53.1%) of the title compound was obtained according to the same procedure as Example 73 using 22 mg (46.5 pmol) of the compound obtained in Example 35.

$^1$H NMR (DMSO-d$_6$, ppm); δ 10.65 (1H, s), 9.58 (1H, s), 9.31 (1H, s), 9.29 (1H, s), 7.82 (1H, t), 7.72–7.50 (7H, m), 6.88 (1H, d). FAB MS (m/e)=462 [M$^+$+1].

EXAMPLE 84

Synthesis of N-[2-(3,4-Dihydroxyphenyl)-3-hydroxy-4-oxo-4H-chromen-6-yl]-4-(trifluoromethyl)benzenesulfonamide (Compound 39)

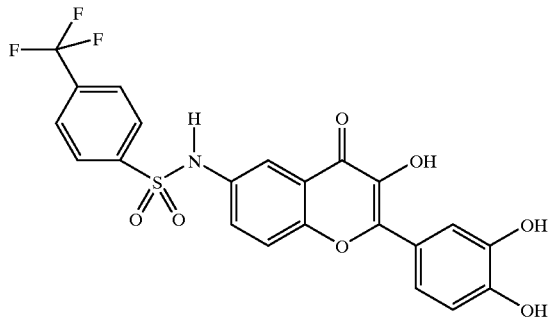

10 mg (Yield 85.5%) of the title compound was obtained according to the same procedure as Example 73 using 12 mg (23.7 pmol) of the compound obtained in Example 36.

$^1$H NMR (DMSO-d$_6$, ppm); δ 10.78 (1H, s), 7.95 (4H, m), 7.73–7.50 (5H, m), 6.88 (1H, d). FAB MS (m/e)=494 [M$^+$+1].

EXAMPLE 85

Synthesis of 4-Chloro-N-[2-(3,4-dihydroxyphenyl)-3-hydroxy-4-oxo-4H-chromen-6-yl]-3-nitrobenzenesulfonamide (Compound 40)

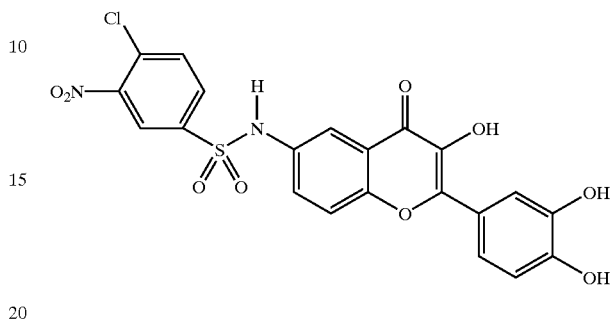

19 mg (Yield 97.3%) of the title compound was obtained according to the same procedure as Example 73 using, 20 mg (38.7 pmol) of the compound obtained in Example 37.

$^1$H NMR (DMSO-d$_6$, ppm), δ

10.84 (1H, s), 9.60 (1H, br s), 9.35 (1H, s), 9.30 (1H, br s), 8.41 (1H, s), 7.96 (2H, m), 7.74–7.66 (3H, m), 7.56–7.50 (2H, m), 6.89 (1H, d). FAB MS (m/e)=505 [M$^+$+1].

EXAMPLE 86

Synthesis of 3-Chloro-N-[2-(3,4-dihydroxyphenyl)-3-hydroxy-4-oxo-4H-chromen-6-yl]-1-propanesulfonamide (Compound 41)

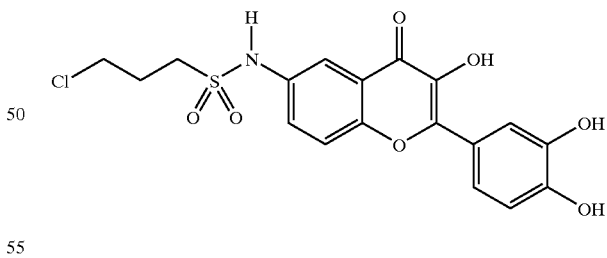

19 mg (Yield 97.8%) of the title compound was obtained according to the same procedure as Example 73 using 20 mg (45.7 pmol) of the compound obtained in Example 38.

$^1$H NMR (DMSO-d$_6$, ppm); δ 10.20 (1H, s), 9.30 (1H, br s), 7.89 (1H, s), 7.72 (2H, m), 7.59 (2H, m), 6.90 (1H, d), 3.71 (2H, m), 3.26 (2H, m), 2.12 (2H, m). FAB MS (m/e)=426 [M$^+$+1].

EXAMPLE 87

Synthesis of N-[2-(3,4-Dihydroxyphenyl)-3-hydroxy-4-oxo-4H-chromen-6-yl]-2,4-difluorobenzenesulfonamide (Compound 42)

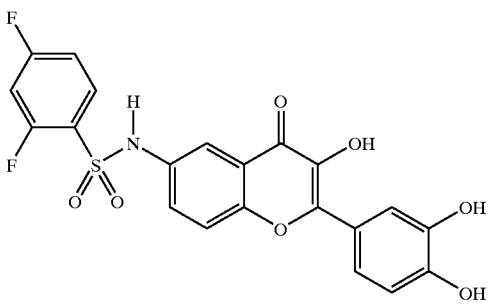

9.4 mg (Yield 48.6%) of the title compound was obtained according to the same procedure as Example 73 using 20 mg (42 pmol) of the compound obtained in Example 39.

$^1$H NMR (DMSO-d$_6$, ppm); δ 10.94 (1H, s), 9.30 (1H, br s), 7.90 (1H, m), 7.74 (1H, m), 7.68 (2H, m), 7.54 (3H, m), 7.25 (1H, m), 6.88 (1H, d). FAB MS (m/e)=462 [M$^+$+1].

EXAMPLE 88

Synthesis of N-[2-(3,4-Dihydroxyphenyl)-3-hydroxy-4-oxo-4H-chromen-6-yl]-4-fluorobenzenesulfonamide (Compound 43)

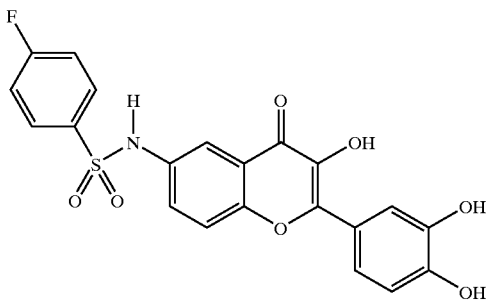

5.2 mg (Yield 26.5%) of the title compound was obtained according to the same procedure as Example 73 using 20 mg (44 pmol) of the compound obtained in Example 40.

$^1$H NMR (DMSO-d$_6$, ppm); δ 10.57 (1H, br s), 9.60 (1H, br s), 9.30 (1H, br s), 7.79 (2H, m), 7.72 (3H, m), 7.50 (2H, m), 7.41 (2H, m), 6.88 (1H, d). FAB MS (m/e)=444 [M$^+$+1].

EXAMPLE 89

Synthesis of N-[2-(3,4-Dihydroxyphenyl)-3-hydroxy-4-oxo-4H-chromen-6-yl]-2-(2,2,2-trifluoroacetyl)-1,2,3,4-tetrahydro-7-isoquinolinesulfonamide (Compound 44)

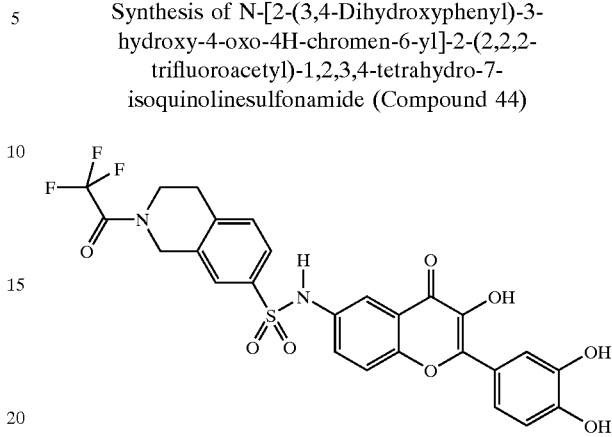

3.5 mg (Yield 17.6%) of the title compound was obtained according to the same procedure as Example 73 using 20 mg (34 pmol) of the compound obtained in Example 41.

$^1$H NMR (DMSO-d$_6$, ppm); δ 9.70–9.00 (4H, br m), 7.74–7.20 (8H, m), 6.88 (1H, d), 4.30 (2H, m), 3.80 (2H, m), 3.01 (2H, m). FAB MS (m/e)=577 [M$^+$+1].

EXAMPLE 90

Synthesis of 4-({[2-(3,4-Dihydroxyphenyl)-3-hydroxy-4-oxo-4H-chromen-6-yl]amino}sulfonyl) benzoic Acid (Compound 45)

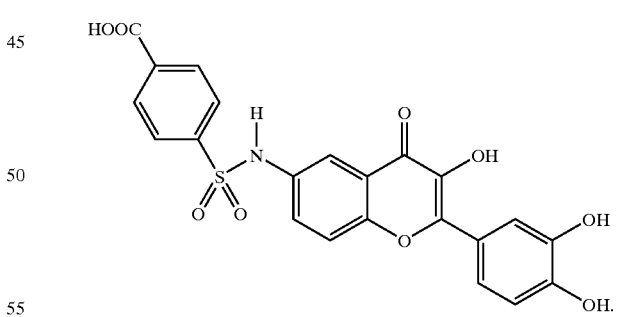

9.6 mg (Yield 49%) of the title compound was obtained according to the same procedure as Example 73 using 20 mg (41.5 pmol) of the compound obtained in Example 42.

$^1$H NMR (DMSO-d$_6$, ppm); δ 10.56 (1H, s), 9.30 (1H, br s), 8.10–7.50 (9H, m), 6.89 (1H, m). FAB MS (m/e)=470 [M$^+$+1].

EXAMPLE 91

Synthesis of N-[2-(3,4-Dihydroxyphenyl)-3-hydroxy-4-oxo-4H-chromen-6-yl]-1,2,3,4-tetrahydro-7-isoquinolinesulfonamide (Compound 46)

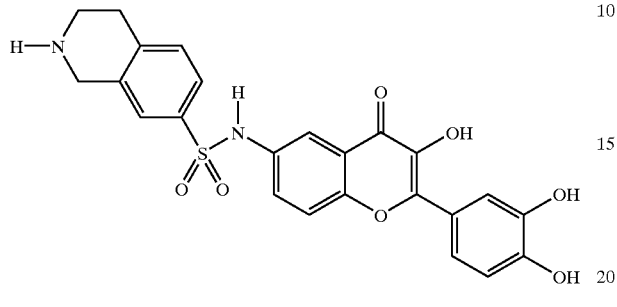

7.8 mg (Yield 55.6%) of the title compound was obtained according to the same procedure as Example 73 using 14.4 mg (29.2 pmol) of the compound obtained in Example 43.

$^1$H NMR (DMSO-$d_6$, ppm); δ 10.64 (1H, s), 9.63 (1H, s), 9.29 (1H, br s), 9.0 (1H, m), 7.74–7.40 (8H, m), 6.89 (1H, d), 4.30 (2H, m), 3.47 (2H, m), 3.00 (2H, m). FAB MS (m/e)=481 [M$^+$+1].

EXAMPLE 92

Synthesis of N-Cyclohexyl-N'-[2-(3,4-dihydroxyphenyl)-3-hydroxy-4-oxo-4H-chromen-6-yl]sulfamide (Compound 47)

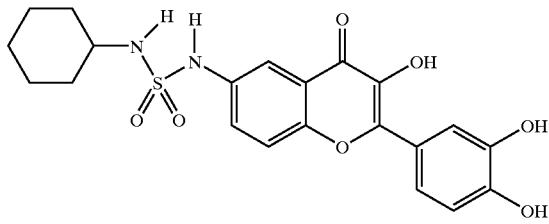

1.5 mg (Yield 25.8%) of the title compound was obtained according to the same procedure as Example 73 using 6 mg (13 pmol) of the compound obtained in Example 44.

$^1$H NMR (MeOH-$d_4$, ppm); δ 7.89–7.50 (5H, m), 6.91 (1H, d), 3.15 (1H, m), 1.79–1.16 (10H, m). FAB MS (m/e)=447 [M$^+$+1].

EXAMPLE 93

Synthesis of N-[2-(3,4-Dihydroxyphenyl)-3-hydroxy-4-oxo-4H-chromen-6-yl]-4-(4-morpholinyl)-3-nitrobenzenesulfonamide (Compound 48)

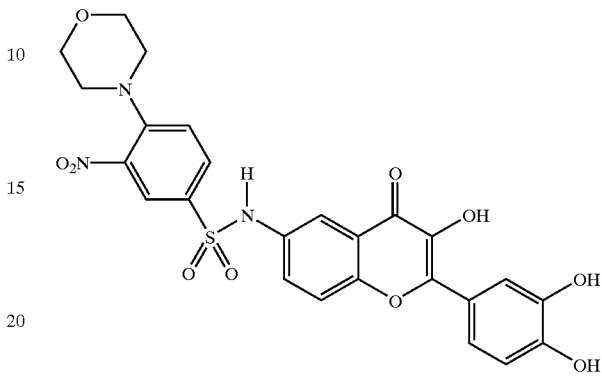

5 mg (Yield 25.5%) of the title compound was obtained according to the same procedure as Example 73 using 20 mg (35.2 pmol) of the compound obtained in Example 45.

$^1$H NMR (MeOH-$d_4$, ppm); δ 7.92 (1H, s), 7.53 (31H, m), 7.45 (1H, d), 7.36 (2H, m), 7.01 (1H, d), 6.65 (1H, d), 3.49 (4H, m), 2.90 (4H, m). FAB MS (m/e)=556 [M$^+$+1].

EXAMPLE 94

Synthesis of N-[2-(3,4-Dihydroxyphenyl)-3-hydroxy-4-oxo-4H-chromen-6-yl]-4-(4-methyl-1-piperazinyl)-3-nitrobenzenesulfonamide (Compound 49)

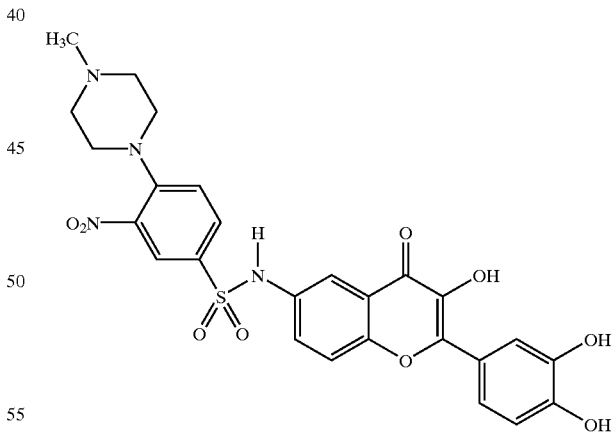

22.5 mg (Yield 76.5%) of the title compound was obtained according to the same procedure as Example 73 using 30 mg (51.7 pmol) of the compound obtained in Example 46.

$^1$H NMR (MeOH-$d_4$, ppm); δ 8.30 (1H, s), 7.90 (1H, m), 7.78 (2H, m), 7.69 (1H, d), 7.60 (2H, m), 7.40 (1H, m), 6.89 (1H, d), 3.57 (4H, m), 3.40 (4H, m), 2.94 (3H, s). FAB MS (m/e)=569 [M$^+$+1].

EXAMPLE 95

Synthesis of 3-amino-N-[2-(3,4-Dihydroxyphenyl)-3-hydroxy-4-oxo-4H-chromen-6-yl]-4-(4-methyl-1-piperazinyl)benzenesulfonamide (Compound 50)

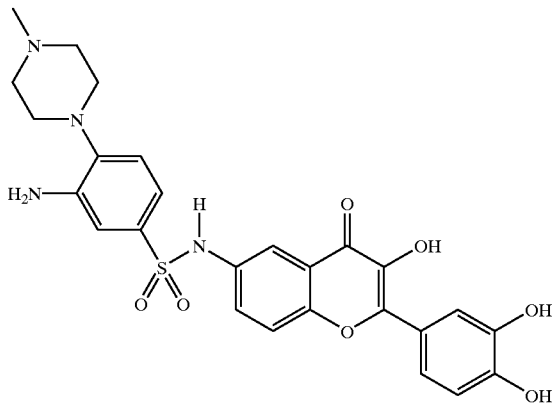

10 mg (17.6 pmol) of the compound obtained in Example 94 was dissolved in 5 ml of methanol, catalytic amount of 10% Pd/C was added thereto, and the mixture was reacted under 1atm of hydrogen gas at room temperature for 3 hours. The resulting product was filtered through celite pad, and washed with methanol. The filtrate was concentrated, and dried to give 6.4 mg of the title compound in a yield of 67.5%.

$^1$H NMR (MeOH-d$_4$, ppm); δ 7.77 (2H, d), 7.69 (1H, d), 7.55 (2H, m), 7.17 (1H, s), 7.06 (1H, d), 7.01 (1H, d), 6.89 (1H, d), 3.34 (8H, m), 2.85 (3H, s). FAB MS (m/e)=539 [M$^+$+1].

EXAMPLE 96

Synthesis of N-[2-(3,4-Dihydroxyphenyl)-3-hydroxy-4-oxo-4H-chromen-6-yl]acetamide (Compound 51)

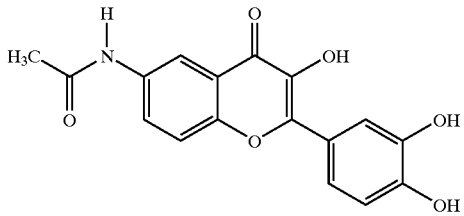

20 mg (59pmol) of the compound obtained in Example 23 was dissolved in 2 ml of methylenechloride, and the mixture was reacted with excess amount of boron tribromide (BBr$_3$) at room temperature for 3 hours. The resulting product was concentrated. Then the produced solid was washed with methylenechloride and 10% methanol/methylenechloride, filtered, and dried to give 18 mg of the title compound in a yield of 93%.

$^1$H NMR (MeOH-d$_4$, ppm); δ 8.32 (1H, s), 7.94 (1H, d), 7.80 (1H, s), 7.72 (1H, d), 7.69 (1H, d), 6.91 (1H, d), 2.16 (314, s). FAB MS (m/e)=328 [M$^+$+1].

EXAMPLE 97

Synthesis of N-[2-(3,4-Dihydroxyphenyl)-3-hydroxy-4-oxo-4H-chromen-6-yl]benzamide (Compound 52)

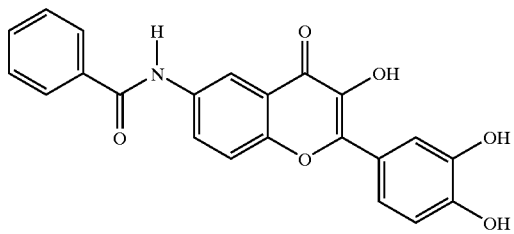

24.8 mg (Yield 85%) of the title compound was obtained according to the same procedure as Example 96 except that 30 mg (74.8 pmol) of the compound obtained in Example 47 was used instead of the compound obtained in Example 23.

$^1$H NMR (MeOH-d$_4$+DMSO-d$_6$, ppm); δ 11.07 (1H, s), 9.25 (1H, s), 8.80 (1H, d), 8.69 (2H, d), 8.51 (1H, s), 8.39 (2H, m), 8.30–8.20 (3H, m), 7.63 (1H, d). FAB MS (m/e)= 390 [M$^+$+1].

EXAMPLE 98

Synthesis of 4-Chloro-N-[2-(3,4-dihydroxyphenyl)-3-hydroxy-4-oxo-4H-chromen-6-yl]benzamide (Compound 53)

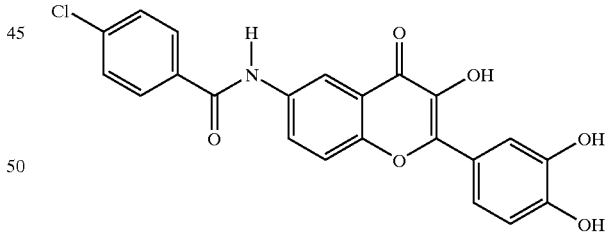

13 mg (Yield 66.7%) of the title compound was obtained according to the same procedure as Example 96 except that 20 mg (46 pmol) of the compound obtained in Example 48 was used instead of the compound obtained in Example 23.

$^1$H NMR (DMSO-d$_6$, ppm); δ 10.59 (1H, s), 9.25 (1H, br s), 8.57 (1H, s), 8.16 (1H, d), 8.05 (2H, d), 7.75 (2H, m), 7.65 (1H, d), 7.63 (1H, d), 6.91 (1H, d). FAB MS (m/e)=424 [M$^+$+1].

EXAMPLE 99

Synthesis of N-Benzyl-N'-[2-(3,4-dihydroxyphenyl)-3-hydroxy-4-oxo-4H-chromen-6-yl]urea (Compound 54)

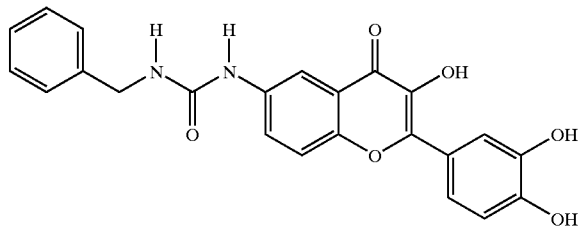

30 mg (69.7 pmol) of the compound obtained in Example 49 was introduced into 3 ml of methylenechloride, and the mixture was reacted with 3 molar equivalents of boron tribromide (BBr$_3$) at room temperature for 3 hours. The remained boron tribromide (BBr$_3$) was decomposed with methanol, and the residue was concentrated under reduced pressure. The produced solid was washed with methylenechloride and 10% methanol/methylenechloride, filtered, and then dried to give 23 mg of the title compound in a yield of 78.9%.

$^1$H NMR (MeOH-d$_4$, ppm); δ 8.83 (1H, s), 8.50 (3H, m), 8.38 (1H, d), 8.29 (1H, d), 8.04 (4H, m), 7.61 (1H, d). FAB MS (m/e)=419 [M$^+$+1].

EXAMPLE 100

Synthesis of N-(4-Bromophenyl)-N'-[2-(3,4-dihydroxyphenyl)-3-hydroxy-4-oxo-4H-chromen-6-yl]urea (Compound 55)

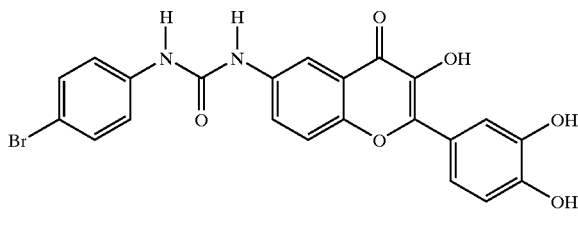

18 mg (Yield 92.5%) of the title compound was obtained according to die same procedure as Example 99 except that 20 mg (40 pmol) of the compound obtained in Example 50 was used instead of the compound obtained in Example 49.

$^1$H NMR (DMSO-d$_6$, ppm); δ 7.73 (2H, m), 7.57 (3H, m), 7.46 (2H, m), 7.30 (1H, m), 6.89 (2H, m). FAB MS (m/e)=484 [M$^+$+1].

EXAMPLE 101

Synthesis of N-[2-(3,4-Dihydroxyphenyl)-3-hydroxy-4-oxo-4H-chromen-6-yl]-N'-phenylurea (Compound 56)

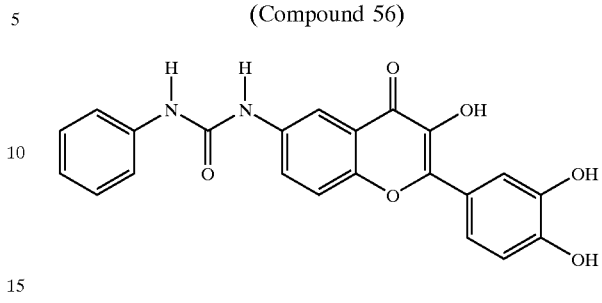

15 mg (Yield 81%) of the title compound was obtained according to the same procedure as Example 99 except that 19 mg (45.6 pmol) of the compound obtained in Example 51 was used instead of the compound obtained in Example 49.

$^1$H NMR (MeOH-d$_4$, ppm); δ 8.13 (1H, s), 7.91 (1H, d), 7.81 (1H, s), 7.72 (1H, m), 7.62 (1H, s), 7.45 (2H, d), 7.29 (2H, m), 7.04 (1H, m), 6.91 (1H, m). FAB MS (m/e)=405 [M$^+$+1].

EXAMPLE 102

Synthesis of N-Benzyl-N'-[2-(3,4-dihydroxyphenyl)-3-hydroxy-4-oxo-4H-chromen-6-yl]urea (Compound 57)

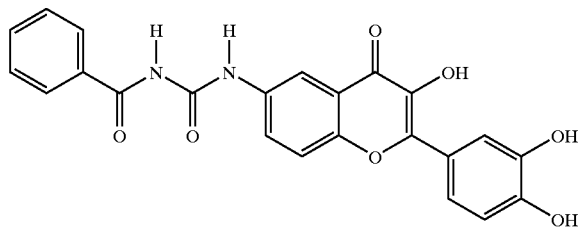

18 mg (Yield 77%) of the title compound was obtained according to the same procedure as Example 99 except that 24 mg (54 pmol) of the compound obtained in Example 52 was used instead of the compound obtained in Example 49.

$^1$H NMR (DMSO-d$_6$, ppm); δ 11.14 (1H, s), 11.02 (1H, s), 8.40 (1H, s), 8.05 (1H, d), 7.90 (1H, d), 7.75–7.54 (6H, m), 6.91 (1H, d). FAB MS (m/e)=433 [M$^+$+1].

EXAMPLE 103

Synthesis of N-(3-Bromophenyl)-N'-[2-(3,4-dihydroxyphenyl)-3-hydroxy-4-oxo-4H-chromen-6-yl]urea (Compound 58)

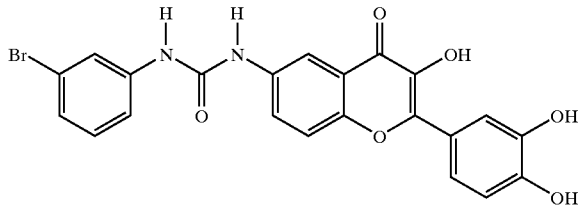

20 mg (Yield 85.5%) of the title compound was obtained according to the same procedure as Example 99 except that 24 mg (48.4 pmol) of the compound obtained in Example 53 was used instead of the compound obtained in Example 49.

$^1$H NMR (MeOH-d$_4$, ppm); δ 8.14 (1H, s), 7.92 (1H, d), 7.81 (2H, m), 7.13 (1H, d), 7.64 (1H, d), 7.36 (1H, d), 7.20–7.17 (2H, m), 6.91 (1H, d). FAB MS (m/e)=484 [M$^+$+1].

EXAMPLE 104

Synthesis of N-(2,4-Dichlorophenyl)-N'-[2-(3,4-dihydroxyphenyl)-3-hydroxy-4-oxo-4H-chromen-6-yl]urea (Compound 59)

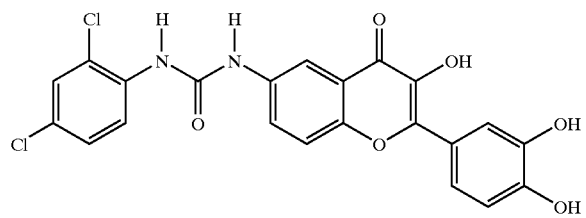

25 mg (Yield 98.5%) of the title compound was obtained according to the same procedure as Example 99 except that 26 mg (53.6 pmol) of the compound obtained in Example 54 was used instead of the compound obtained in Example 49.

$^1$H NMR (MeOH-d$_4$, ppm); δ 8.20 (2H, m), 7.90 (1H, d), 7.81 (1H, s), 7.73 (1H, d), 7.65 (1H, d), 7.48 (1H, s), 7.32 (1H, d), 6.91 (1H, d). FAB MS (m/e)==474 [M$^+$+1].

EXAMPLE 105

Synthesis of N-(3-Cyanophenyl)-N'-[2-(3,4-dihydroxyphenyl)-3-hydroxy-4-oxo-4H-chromen-6-yl]urea (Compound 60)

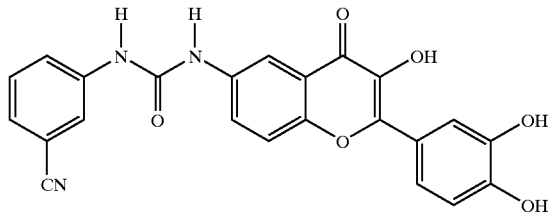

4.9 mg (Yield 50.4%) of the title compound was obtained according to the same procedure as Example 99 except that 10 mg (22.6 pmol) of the compound obtained in Example 55 was used instead of the compound obtained in Example 49.

$^1$H NMR (DMSO-d$_6$, ppm); δ 9.19 (1H, s), 9.13 (1H, s), 8.82 (1H, s), 8.31 (1H, s), 8.01 (1H, s), 7.93 (1H, s), 7.89 (1H, s), 7.74–7.34 (7H, m), 6.90 (1H, s). FAB MS (m/e)=430 [M$^+$+1].

EXAMPLE 106

Synthesis of N-[2-(3,4-Dihydroxyphenyl)-3-hydroxy-4-oxo-4H-chromen-6-yl]-N'-(4-nitrophenyl)urea (Compound 61)

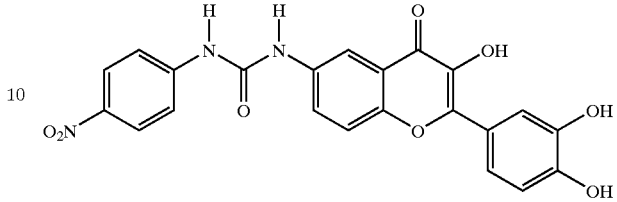

24 mg (Yield 98%) of the title compound was obtained according to the same procedure as Example 99 except that 25 mg (54 pmol) of the compound obtained in Example 56 was used instead of the compound obtained in Example 49.

$^1$H NMR (DMSO-d$_6$, ppm); δ 9.57 (1H, s), 9.28 (1H, s), 8.32 (1H, s), 8.22 (2H, d), 7.74–7.60 (6H, m), 6.90 (1H, d). FAB MS (m/e)=450 [M$_+$+1].

EXAMPLE 107

Synthesis of N-(4-Aminophenyl)-N'-[2-(3,4-dihydroxyphenyl)-3-hydroxy-4-oxo-4H-chromen-6-yl]urea (Compound 62)

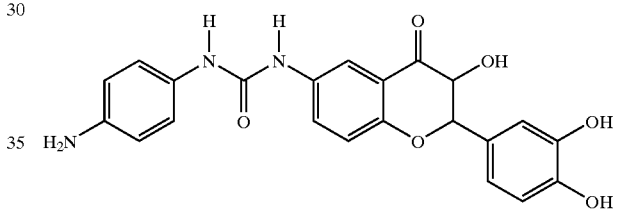

16 mg (35.6 pmol) of the compound obtained in Example 106 was dissolved in 2 ml of methanol, catalytic amount of 10% Pd/C was added thereto, and the mixture was reacted under 1atm of hydrogen gas for 3 hours. The resulting product was filtered through celite pad, and washed with methanol. Then the filtrate was concentrated under reduced pressure to give 3.5 mg of the title compound in a yield of 23%.

$^1$H NMR (DMSO-d$_6$, ppm); δ 9.55 (1H, s), 9.28 (1H, s), 9.20 (1H, s), 8.93 (1H, s), 8.43 (1H, s), 8.25 (1H, s), 7.73–7.59 (4H, m), 7.21 (2H, d), 6.90 (1H, d), 6.69 (2H, d). FAB MS (m/e)=420 [M$^+$+1].

Experimental Example 1

Analysis of inhibitory activity against CDK2/cyclin A and CDK4/cyclin D1 enzyme.

The inhibitory activity against CDK2 is measured by referring to Kitagawa, M. et al., *Oncogene* 9:2549, 1994 and the inhibitory activity against CDK4 is measured by referring to Carlson, B. A. et al., *Cancer Research* 56:2473,1996.

As for CDK2, either the extract from the insect cell infected both with baculovirus which expresses CDK2 gene and baculovirus which expresses cyclin A gene or the active enzyme which had been purified therefrom was used. CDK4 enzyme was also obtained from the insect cell infected both with baculovirus expressing CDK4 gene and baculovirus expressing cyclin D1 gene. As the substrate for CDK2, either histon H1 or Rb protein was used. Rb protein was also used as the substrate for CDK4.

Specifically the activities of enzymes CDK2/cyclin A and CDK4/cyclin D1 were determined according to the following procedure.

100 ng of enzyme was reacted in a total 1000 μl of 20 mM Tris (pH 8.0), 100 mM NaCl, 10 mM MgCl$_2$ buffer solution containing 20 μg of GST-RB protein, 100 μM of ATP and 5 μCi of P$_{32}$-γ-ATP at 30° C. for 30 minutes. Then, the enzyme reaction was stopped by adding EDTA to a concentration of 20 mM. Subsequently, 30 μl of 50% glutathione bead (purchased from Pharmacia) was added to attach GST-RB to the bead, which was washed three times with 20mM Tris (pH 8.0), 100 mM NaCl, 10 mM EDTA solution, and then scintillation counting was carried out. To analyze the inhibitory activity of the compound, the inhibitor having a proper concentration was added to the enzyme reaction solution, and then the enzyme activity was measured according to the above method.

The inhibitory activity of the compound of formula (1) according to the present invention against CDK2 and CDK4 is represented as IC$_{50}$ value. The test results are shown in the following Table 1. The compounds which are not included in Examples(compound 63, 64, 65 and 66) were synthesized and purified according to the same procedure as examples, and then IC$_{50}$ thereof was measured.

TABLE 1

| Co. No. | Structure | M.W. | CDK2 IC$_{50}$ (μM) | CDK4 IC$_{50}$ (μM) |
|---|---|---|---|---|
| 1 | (7-MeO, 4'-Cl flavone) | 286 | >200 | >200 |
| 2 | (7-MeO flavone) | 252 | >200 | >200 |
| 3 | (7-HO flavone) | 238 | >200 | >200 |
| 4 | (5-OMe, 3-OH, 2-(benzo[d][1,3]dioxol-5-yl) flavone) | 312 | >100 | >100 |
| 5 | (6-MeO, 3-OH, 2-(benzo[d][1,3]dioxol-5-yl) flavone) | 312 | >100 | >100 |

TABLE 1-continued

| Co. No. | Structure | M.W. | CDK2 IC$_{50}$ ($\mu$M) | CDK4 IC$_{50}$ ($\mu$M) |
|---|---|---|---|---|
| 6 | 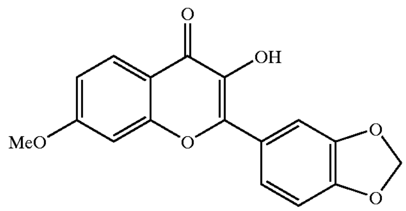 | 312 | >100 | >100 |
| 7 | 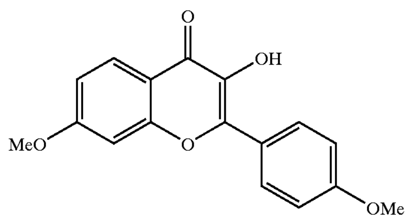 | 298 | >100 | >100 |
| 8 | 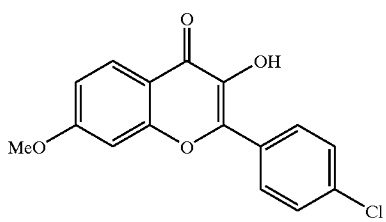 | 302 | >100 | >100 |
| 9 | 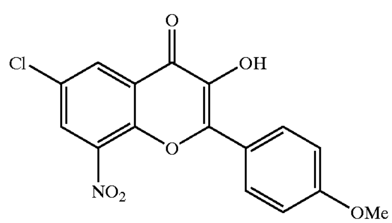 | 347 | >100 | >100 |
| 10 | 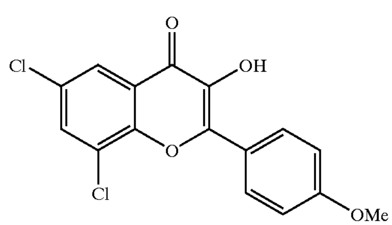 | 336 | >100 | >100 |
| 11 | 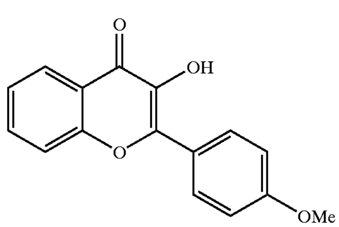 | 268 | >100 | >100 |

TABLE 1-continued

| Co. No. | Structure | M.W. | CDK2 IC$_{50}$ ($\mu$M) | CDK4 IC$_{50}$ ($\mu$M) |
|---|---|---|---|---|
| 12 | 6-Cl, 3-OH, 3',4'-diOH flavone | 305 | <5 | <10 |
| 13 | 6-Br, 3-OH, 3',4'-diOH flavone | 350 | <5 | <5 |
| 14 | 6-OH, 3-OH, 3',4'-diOH flavone | 286 | <5 | <5 |
| 15 | 6-NH$_2$, 3-OH, 3',4'-diOH flavone | 285 | <5 | <5 |
| 16 | 6-OCH$_3$, 3-OH, 3',4'-diOH flavone | 300 | <10 | <10 |
| 17 | 6-F, 3-OH, 3',4'-diOH flavone | 289 | <10 | <10 |

TABLE 1-continued
| Co. No. | Structure | M.W. | CDK2 IC$_{50}$ ($\mu$M) | CDK4 IC$_{50}$ ($\mu$M) |
|---|---|---|---|---|
| 18 | 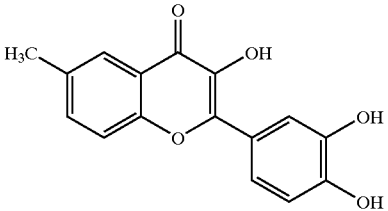 | 285 | <10 | <10 |
| 19 | 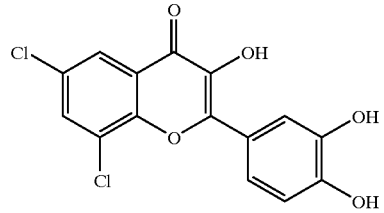 | 339 | <10 | <10 |
| 20 | 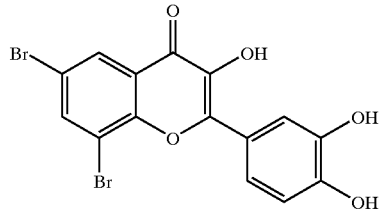 | 429 | <5 | <5 |
| 21 | 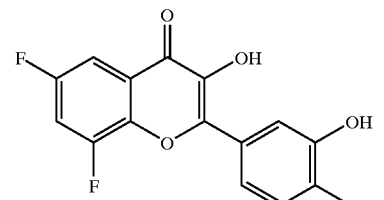 | 307 | <10 | <10 |
| 22 | 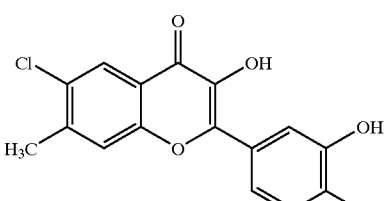 | 319 | <10 | <10 |
| 23 | 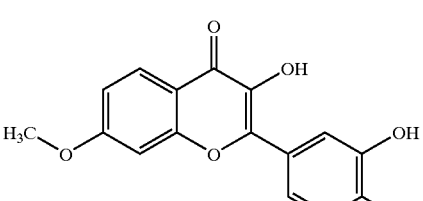 | 300 | <30 | <30 |

TABLE 1-continued

| Co. No. | Structure | M.W. | CDK2 IC$_{50}$ ($\mu$M) | CDK4 IC$_{50}$ ($\mu$M) |
|---|---|---|---|---|
| 24 | 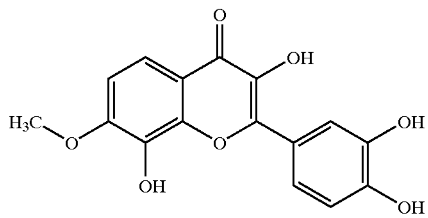 | 317 | <10 | <10 |
| 25 | 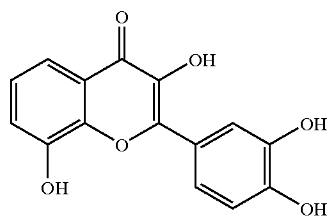 | 287 | <10 | <10 |
| 26 | 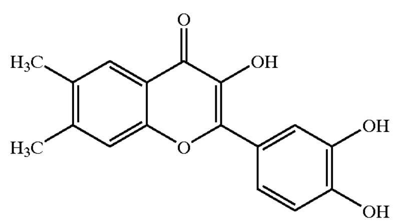 | 299 | <10 | <10 |
| 27 | 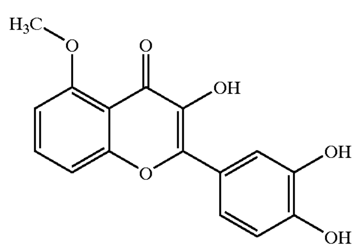 | 300 | <10 | <10 |
| 28 | 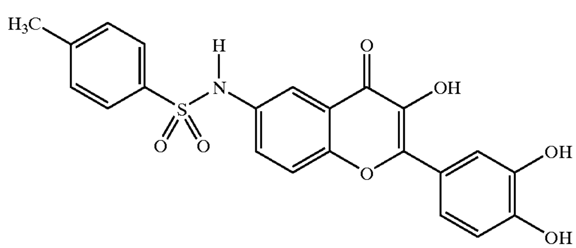 | 439 | 56 | 7.8 |
| 29 | 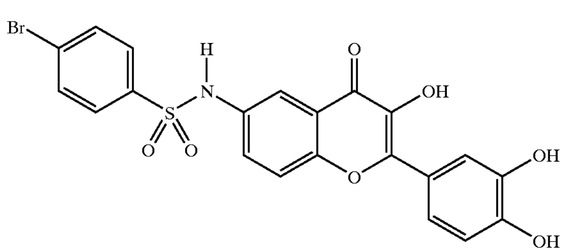 | 504 | 17.8 | 1.8 |

TABLE 1-continued

| Co. No. | Structure | M.W. | CDK2 IC$_{50}$ ($\mu$M) | CDK4 IC$_{50}$ ($\mu$M) |
|---|---|---|---|---|
| 30 | 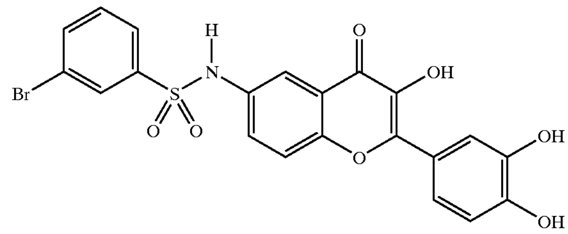 | 504 | 14 | 2.1 |
| 31 | 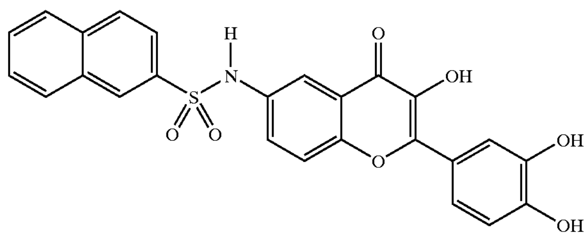 | 475 | 35.5 | 4.2 |
| 32 | 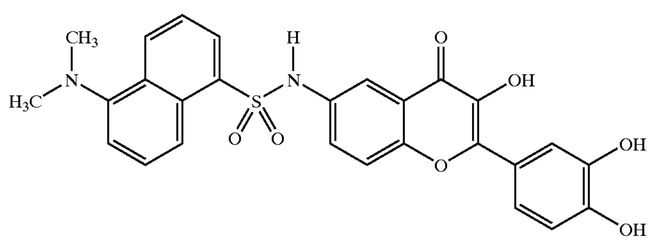 | 518 | 35.5 | 4.2 |
| 33 | 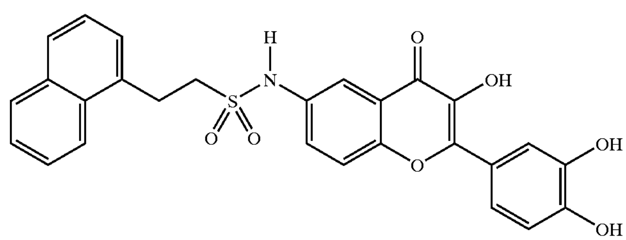 | 503 | 63 | 5 |
| 34 | 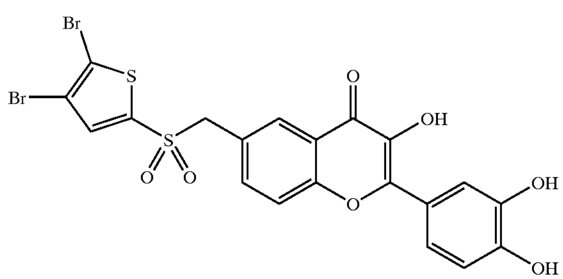 | 589 | 3.0 | 1.0 |
| 35 | 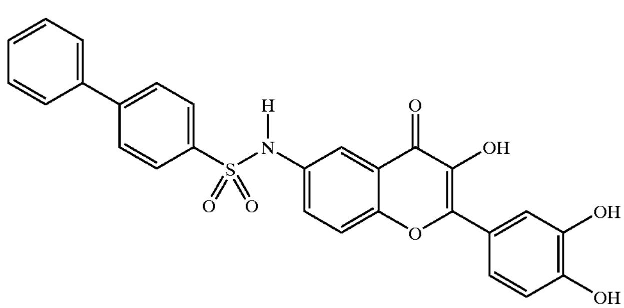 | 501 | 4.0 | 2.0 |

TABLE 1-continued

| Co. No. | Structure | M.W. | CDK2 IC$_{50}$ ($\mu$M) | CDK4 IC$_{50}$ ($\mu$M) |
|---|---|---|---|---|
| 36 | 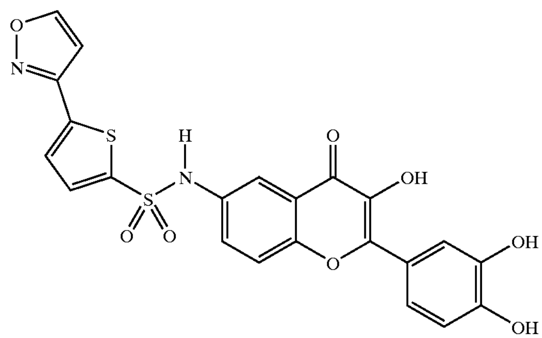 | 498 | 12.0 | 3.5 |
| 37 | 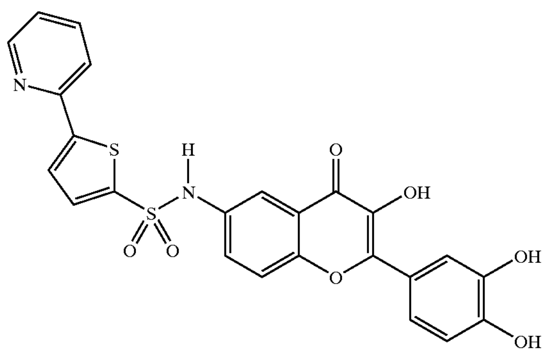 | 508 | 12.5 | 4.2 |
| 38 | 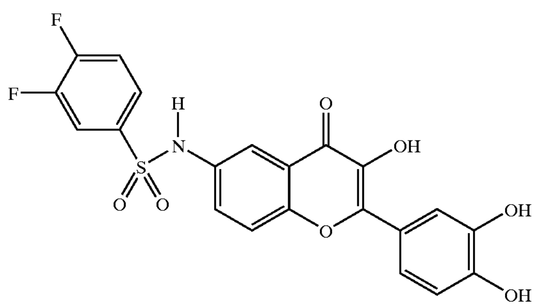 | 461 | 19.0 | 2.6 |
| 39 | 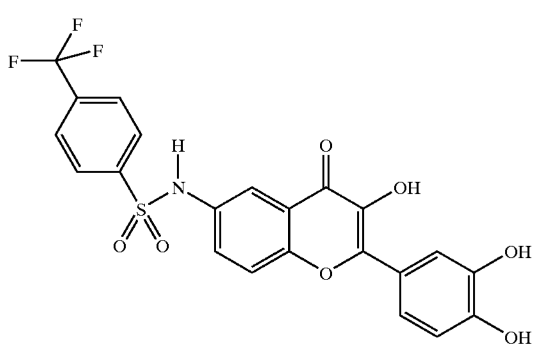 | 493 | 55.0 | 6.4 |

TABLE 1-continued

| Co. No. | Structure | M.W. | CDK2 IC$_{50}$ ($\mu$M) | CDK4 IC$_{50}$ ($\mu$M) |
|---|---|---|---|---|
| 40 | 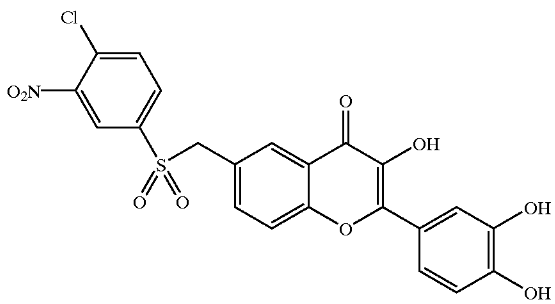 | 504 | 80.0 | 2.5 |
| 41 | 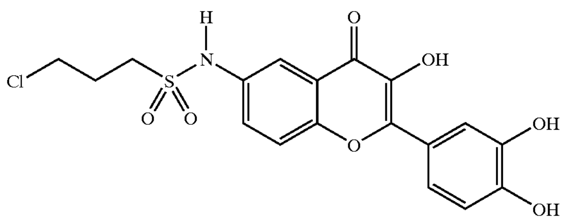 | 425 | 20.0 | 6.5 |
| 42 | 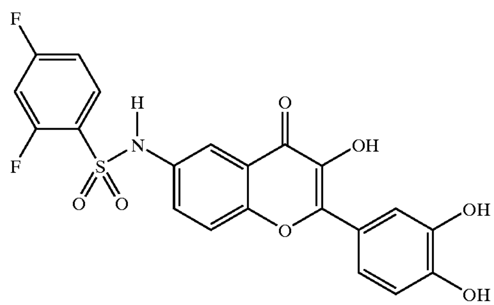 | 461 | 46.0 | 4.3 |
| 43 | 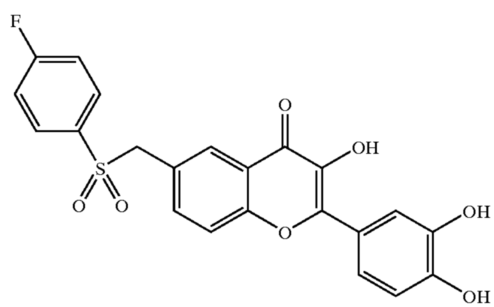 | 443 | 8.6 | 2.1 |
| 44 | 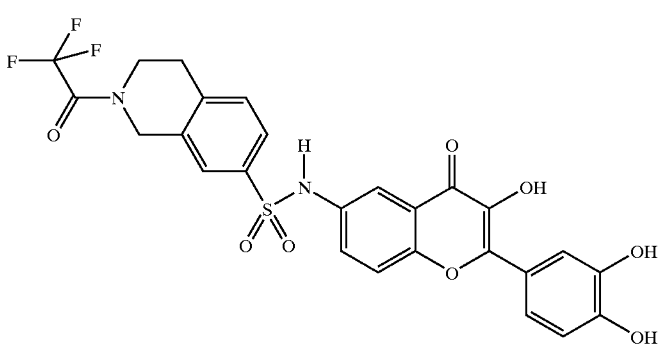 | 576 | 4.1 | 2.3 |

TABLE 1-continued

| Co. No. | Structure | M.W. | CDK2 IC$_{50}$ ($\mu$M) | CDK4 IC$_{50}$ ($\mu$M) |
|---|---|---|---|---|
| 45 | 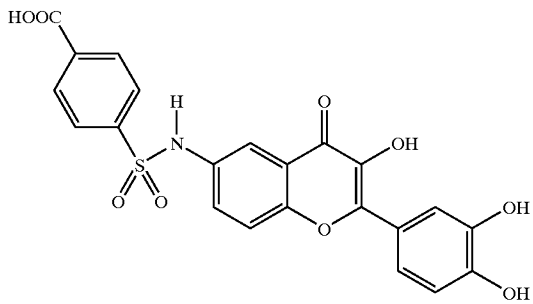 | 469 | 28.2 | 6.0 |
| 46 | 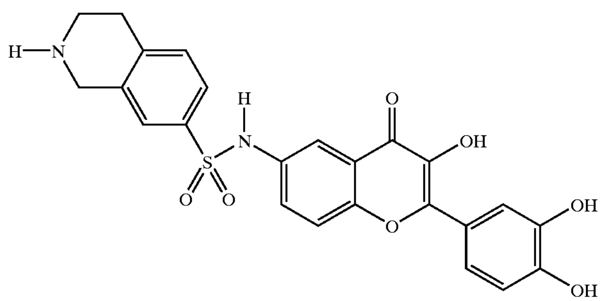 | 480 | 82.0 | 6.3 |
| 47 | 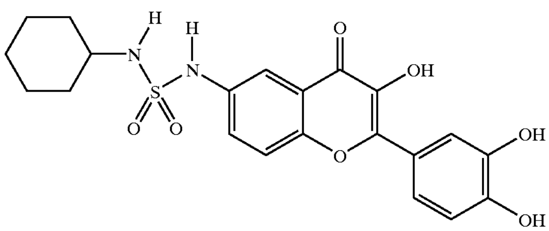 | 446 | 65.0 | 2.0 |
| 48 | 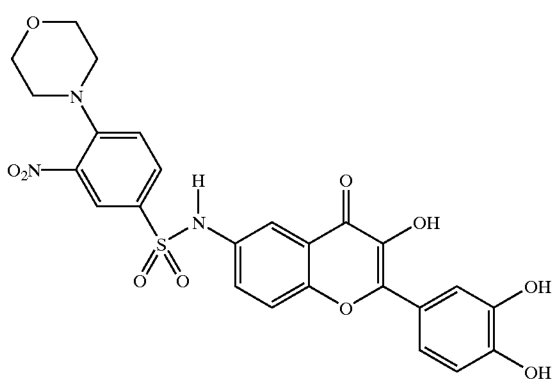 | 555 | 200 | 0.94 |

TABLE 1-continued

| Co. No. | Structure | M.W. | CDK2 IC$_{50}$ ($\mu$M) | CDK4 IC$_{50}$ ($\mu$M) |
|---|---|---|---|---|
| 49 | 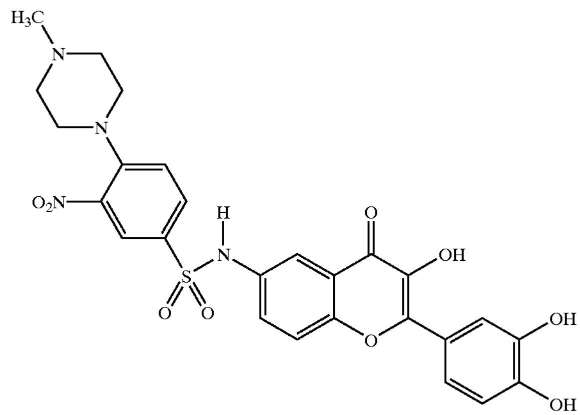 | 568 | 31 | 1.6 |
| 50 | 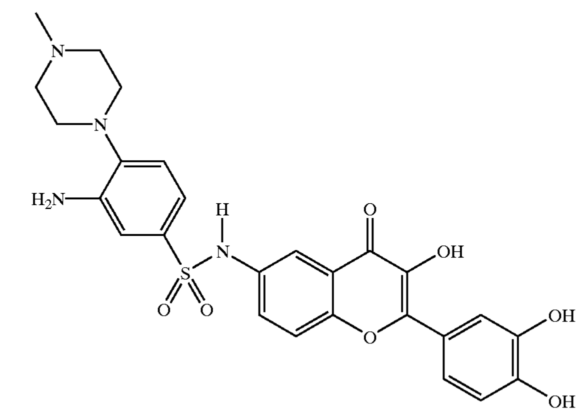 | 538 | >200 | 30 |
| 51 | 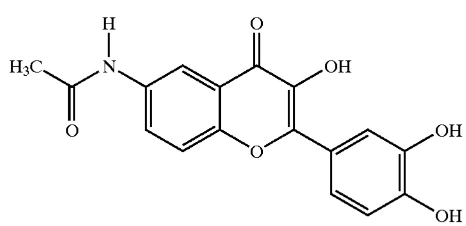 | 327 | 5.6 | 5.6 |
| 52 | 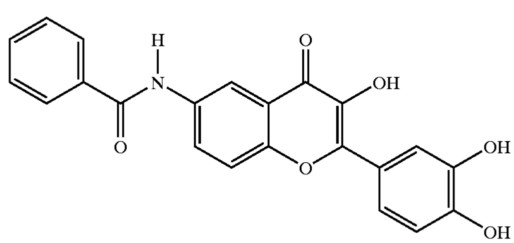 | 389 | 23 | 6 |
| 53 | 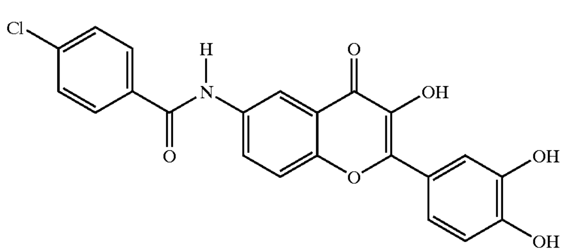 | 423 | >100 | 5.6 |

TABLE 1-continued

| Co. No. | Structure | M.W. | CDK2 IC$_{50}$ ($\mu$M) | CDK4 IC$_{50}$ ($\mu$M) |
| --- | --- | --- | --- | --- |
| 54 | 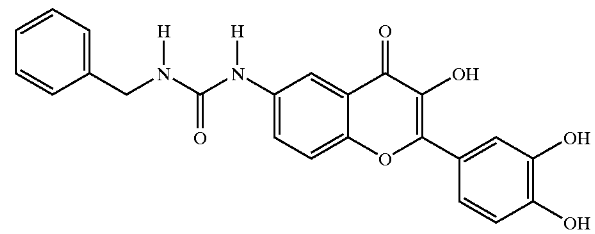 | 418 | 2.3 | 2.8 |
| 55 | 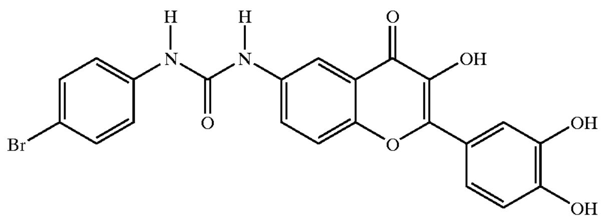 | 483 | 1.3 | 0.7 |
| 56 | 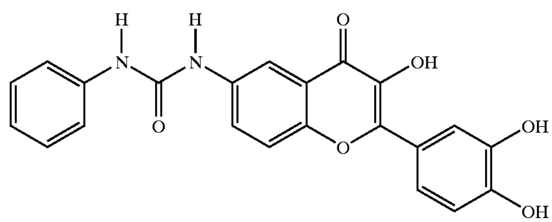 | 404 | 5.0 | 4.2 |
| 57 | 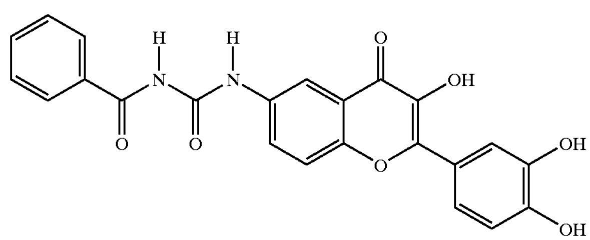 | 432 | 22.4 | 18.0 |
| 58 | 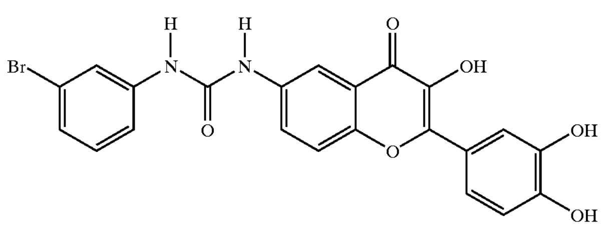 | 483 | 4.2 | 4.2 |
| 59 | 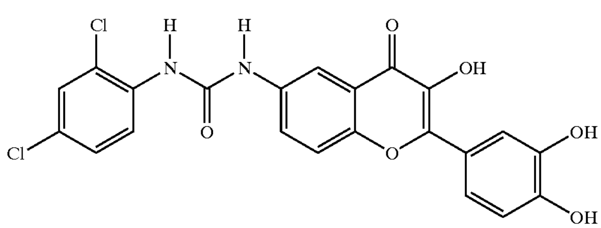 | 473 | 20.0 | 10.0 |

TABLE 1-continued

| Co. No. | Structure | M.W. | CDK2 IC$_{50}$ ($\mu$M) | CDK4 IC$_{50}$ ($\mu$M) |
|---|---|---|---|---|
| 60 | 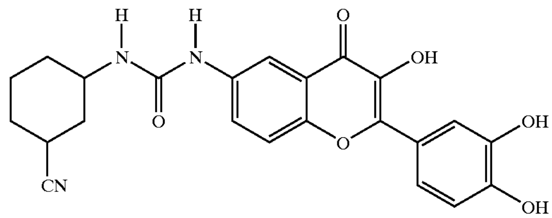 | 429 | 4.7 | 2.7 |
| 61 | 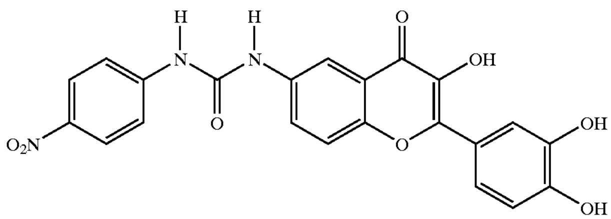 | 449 | 5.6 | 1.7 |
| 62 | 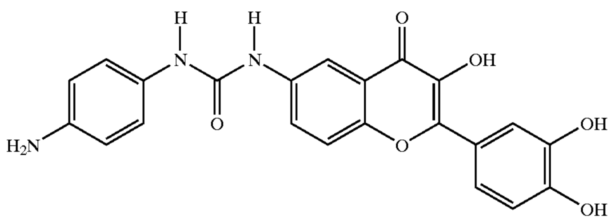 | 419 | 2.6 | 2.3 |
| 63 | 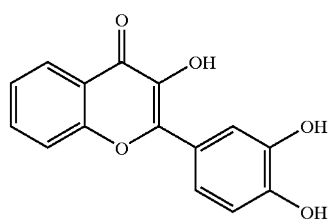 | 270 | <10 | <10 |
| 64 | 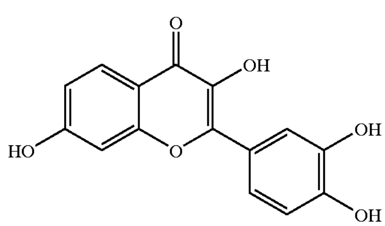 | 286 | <5 | <10 |
| 65 | 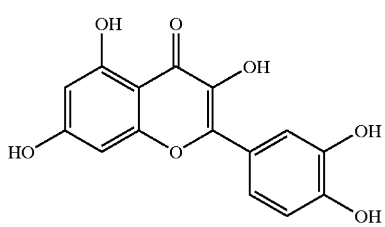 | 302 | <50 | <50 |

TABLE 1-continued

| Co. No. | Structure | M.W. | CDK2 IC$_{50}$ ($\mu$M) | CDK4 IC$_{50}$ ($\mu$M) |
|---|---|---|---|---|
| 66 | 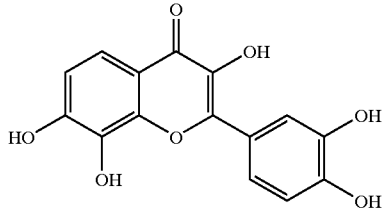 | 302 | <10 | <10 |

As can be seen from the results described in the above Table 1, since novel flavone derivative of formula (1) according to the present invention has an excellent inhibitory activity against CDK2 and CDK4, it can be used advantageously as an anti-cancer agent.

In addition, it can be useful as an agent for treating neurodegenerative disease because it has an inhibitory activity against CDK5 which is a homology with CDK2 and is included in the same family (Ref.: John Leu et al., "Neuronal CDC2-like kinase", TIBS., January 1995, pp33~37).

Experimental Example 2

Acute Toxicity Experiment

The acute oral toxcities of the compounds 14, 17, 28, 39, 51 and 57 each of which is obtained in Examples 14, 17, 73,84, 96 and 102, respectively are investigated in the following.

Solutions containing a compound in several different concentrations from each other were prepared, and they were administered orally to ICR male mouse with a dose of 10 ml/kg.

After administration, lethality and symptoms for 7 days were observed, and LD$_{50}$ (mg/kg) was calculated according to Litchfield-Wilcoxon' method. The result are represented in the following Table 2.

TABLE 2

| Test Compound No. | LD$_{50}$ (mg/kg) |
|---|---|
| 14 | >3,000 |
| 17 | >3,000 |
| 28 | >3,000 |
| 39 | >3,000 |
| 51 | >3,000 |
| 57 | >3,000 |

What is claimed is:

1. A compound represented by the following formula (1):

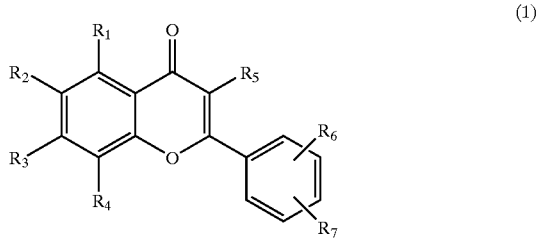

(1)

In which
R$_1$, R$_3$, and R$_4$ each independently represent hydrogen, halogen, hydroxy, alkyl, lower alkoxy, amino or nitro,
R$_2$ represents

wherein
A represents amino which may be optionally substituted with alkyl, cycloalkyl, aralkyl, acyl, or aryl which is optionally substituted with one or two subsituents selected from the group consisting of halogen, cyano, nitro and amino; or 1,2,3,4-tetrahydroisoquinoline which may be optionally substituted with halogenoalkylcarbonyl; or alkyl, aryl, aralkyl or heteroaryl each of which may be optionally substituted with one or two substituents selected from the group consisting of alkyl, halogenoalkyl, halogen, dialkylamino, phenyl, nitro, amino, isooxazolyl, pyridine, carboxy, morpholine, methylpiperazine and cyano,
Y represents SO$_2$,
B represents hydrogen or alkyl,
R$_5$ represents hydrogen or hydroxy, and
R$_6$ and R$_7$ are substituted at o-, m- or p-position from each other and each independently represents hydrogen, hydroxy, halogen or lower alkoxy or together represent lower alkylenedioxy, or
a pharmaceutically acceptable salt, hydrate, solvate and isomer thereof.

2. The compound of claim 1, wherein
R$_1$, R$_3$ and R$_4$ each independently represent hydrogen, halogen, hydroxy, alkyl or amino, provided that two or more of these three substituents are hydrogen, R₂ represents

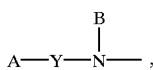

wherein
A represents amino which may be optionally substituted with alkyl, cycloalkyl, aralkyl, acyl, or aryl which is optionally substituted with one or two substituents selected from the group consisting of halogen, cyano, nitro and amino; or 1,2,3,4-tetrahydroisoquinoline which may be optionally substituted with halogenoalkylcarbonyl; or alkyl, aryl, aralkyl or heteroaryl each of which may by optionally substituted with one or two substituents selected from the group consisting of alkyl, halogenoalkyl, halogen, dialkylamino, phenyl, nitro, amino, isooxazole, pyridine, carboxy, morpholine, methylpiperazinc and cyano,
Y represents SO₂,
B represents hydrogen or alkyl,
R₅ represents hydroxy, and
R₆ and R₇ represent 3-hydroxy and 4-hydroxy respectively.

3. The compound of claim 2, wherein
R₁, R₃ and R₄ each represent hydrogen,
A represents amino which may be optionally substituted with cycloalkyl; or 1,2,3,4-tetrahydroisoquinoline which may be optionally substituted with halogenoalkylcarbonyl; or alkyl, aryl, aralkyl or heteroaryl each of which may be optionally substituted with one or two substituents selected from the group consisting of alkyl, halogenoalkyl, halogen, dialkylamino, phenyl, nitro, amino, isooxazole, pyridine, carboxy, morpholine and methylpiperazine,
Y represents SO₂, and
B represents hydrogen.

4. The compound of claim 3, wherein A represents 1,2,3,4-tetrahydroisoquinoline which may be optionally substituted with halogenoalkylcarbonyl; or aryl or heteroaryl each of which may be optionally substituted with one or two substituents selected from the group consisting of alkyl, halogenoalkyl, halogen, dialkylamino, phenyl, nitro, amino, isooxazole, pyridine, carboxy, morpholine and methylpiperazine.

5. The compound of claim 1 which is selected from a group consisting of
N-[2-(3,4-dihydroxyphenyl)-3-hydroxy-4-oxo-4H-chromen-6-yl]-4-methylbenzencsulfonatnide,
4-bromo-N-[2-(3,4-dihydroxyphenyl)-3-hydroxy-4-oxo-4H-chromen-6-yl]benzenesulfonamide,
3-bromo-N-[2-(3,4-dihydroxyphenyl)-3-hydroxy-4-oxo-4H-chromen-6-yl]benzenesulfonamide,
N-[2-(3,4-dihydroxyphenyl)-3-hydroxy-4-oxo-4H-chromen-6-yl]-2-naphthalenesulfonamide,
N-[2-(3,4-dihydroxyphonyl)-3-hydroxy-4-oxo-4H-chromen-6-yl]-5-(di-methylamino)-1-niphthalenesulfonamide,
N-[2-(3,4-dihydroxyphonyl)-3-hydroxy-4-oxo-4H-chromen-6-yl]-2-(1-naphthyl)-1-ethanesulfonamide,
4,5-dibromo-N-[2-(3,4-dihydroxyphenyl)-3-hydroxy-4-oxo-4H-chromen-6-yl]-2-thiophenesulfonamide,
N-[2-(3,4-dihydroxyphenyl)-3-hydroxy-4-oxo-4H-chromen-6-yl]-[-1,1'-biphenyl]-4-sulfonamide,
N-[2-(3,4-dihydroxyphenyl)-3-hydroxy-4-oxo-4H-chromen-6-yl]-5-(iso-oxazolyl)-2-thiophenesulfonamide,
N-[2-(3,4-dihydroxyphenyl)-3-hydroxy-4-oxo-4H-chromen-6-yl]-5-(2-pyridinyl)-2-thiophenesulfonamide,
N-[2-(3,4-dihydroxyphenyl)-3-hydroxy-4H-chromen-6-yl]-3,4-di-fluorobenzenesulfonamide,
N-[2-(3,4-dihydroxyphenyl)-3-hydroxy-4-oxo-4H-chromen-6-yl]4-(tri-fluoromethyl)benzenesulfonamide,
4-chloro-N-[2-(3,4-dihydroxyphenyl)-3-hydroxy-4-oxo-4H-chromen-6-yl]-3-nitrobenzenesulfonamide,
3-chloro-N-[2-(3,4-dihydroxyphenyl)-3-hydroxy-4-oxo-4H-chromen-6-yl]-1-propanesulfonamide,
N-[2-(3,4-dihydroxyphenyl)-3-hydroxy-4-oxo-4H-chromen-6-yl]-2,4-di-fluorobenzenesulfonamide,
N-[2-(3,4-dihydroxyphonyl)-3-hydroxy-4-oxo-4H-chromen-6-yl]4-fluorobenzenesulfonamide,
N-[2-(3,4-dihydroxyphenyl)-3-hydroxy-4-oxo-4-H-chromen-6-yl]-2-(2,2,2-trifluoroacetyl)-1,2,3,4-tetrahydro-7-isoquinolinesulfonamide,
4-({(2-(3,4-dihydroxypbenyl)-3-hydroxy-4-oxo-4H-chromen-6-yl]-amino}sulfonyl)benzoic acid,
N-[2-(3,4-dihydroxyphenyl)-3-hydroxy-4-oxo-4H-chromen-6-yl]-1,2,3,4-tetrahydro-7-isoquinolinesulfonamnide,
N-cyclohexyl-N'-[2-(3,4-dihydroxyphenyl)-3-hydroxy-4-oxo-4H-chromen-6-yl]-sulfide,
N-[2-(3,4-dihydroxyphenyl)-3-hydroxy-4-oxo-4H-chromen-6-yl ]-4-(4-morpholinyl)-3-nitrobenzenesulfonamide,
N-[2-(3,4-dihydroxyphenyl)-3-hydroxy-4-oxo-4H-chromen-6-yl ]-4-(4-methyl-1-piperazinyl)-3-nitrobenzenesulfonamide, and
3-amino-N-[2-(3,4-dihydroxyphenyl)-3-hydroxy-4-oxo-4H-chromen-6-yl]-4-(4-methyl-1-piperazinyl)benzenesulfonamide.

6. A process for preparing the compound of formula (1) as defined in claim 1, characterized in that
a) a compound of formula (5):

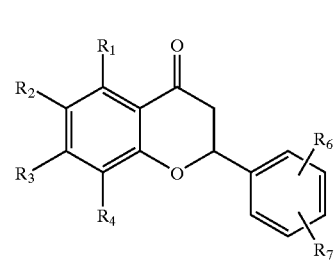

(5)

wherein R₁, R₂, R₃, R₄, R₆ and R₇ are defined as claim 1, is prepared by cyclizing a compound of formula (4):

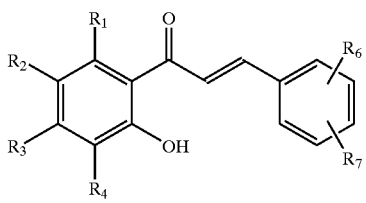
(4)

wherein $R_1$, $R_2$, $R_3$, $R_4$, $R_6$ and $R_7$ are defined as claim 1, in the presence of trifluoroacetic acid, then thus obtained compound of formula (5) is oxidized in the presence of a oxidizing agent in a solvent to produce a compound of formula (1a):

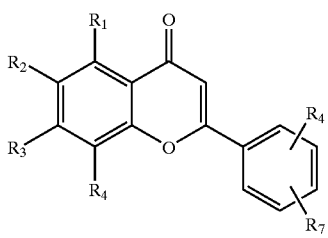
(Ia)

wherein $R_1$, $R_2$, $R_3$, $R_4$, $R_6$ and $R_7$ are defined as claim 1; or b) a compound of formula (6):

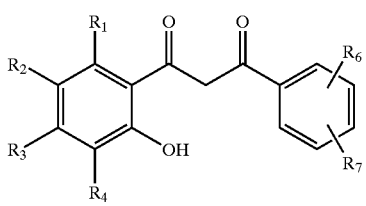
(6)

wherein $R_1$, $R_2$, $R_3$, $R_4$, $R_6$ and $R_7$ are defined as claim 1, is cyclized in the presence of sodium acetate in a solvent to produce the compound of formula (1a); or c) the compound of formula (4) is cyclized in the presence of a base and hydrogen peroxide in a solvent to produce a compound of formula (1b)

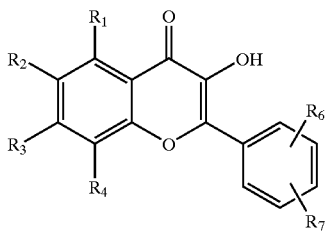
(Ib)

wherein $R_1$, $R_2$, $R_3$, $R_4$, $R_6$ and $R_7$ are defined as claim 1; or d) one to six lower alkoxy groups or alkylenedioxy group in the compound of formula (1) are deprotected in the presence of boron tribromide ($B3r_3$) and converted into hydroxy or dihydroxy group to produce a compound of formula (1) wherein one to six of the sustainments $R_1$, $R_2$, $R_3$, $R_4$, $R_6$ and $R_7$ are hydroxy; or c) a compound of formula (4a)

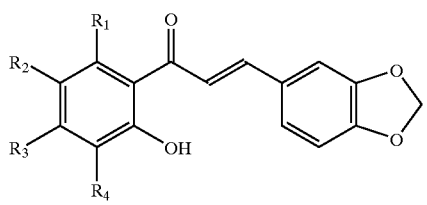
(4a)

wherein $R_1$, $R_2$, $R_3$, and $R_4$ are defined as claim 1, is prepared by reacting 2-hydroxyacetophenone derivative of formula (7):

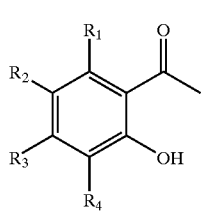
(7)

wherein $R_1$, $R_2$, $R_3$, and $R_4$ are defined as claim 1, with piperonal of formula (8a):

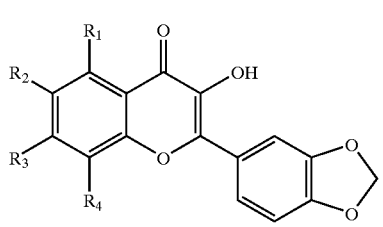
(1cc)

in the presence of a base in a solvent, then thus obtained compound or formula (4a) is cyclized in the presence of hydroxy peroxide to produce a compound of formula (1cc):

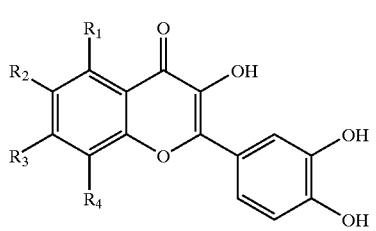
(1dd)

wherein $R_1$, $R_2$, $R_3$ and $R_4$ are defined as claim 1; or f) the produced compound or formula (1cc) is reacted with boron tribromide ($BBr_3$) to produce a compound of formula a (1dd):

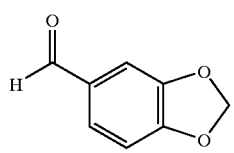

(8a)

wherein $R_1$, $R_2$, $R_3$ and $R_4$ are defined as claim 1; or g) a compound of formula (4b):

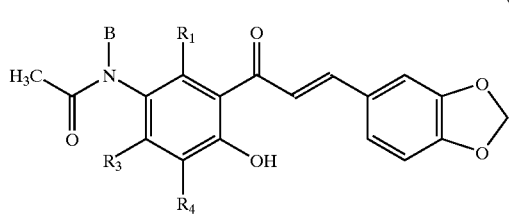

(4b)

wherein $R_1$, $R_3$, $R_4$ and B are defined as claim 1, is prepared by reacting 2-hydroxyacelophenone derivative of formula (7a):

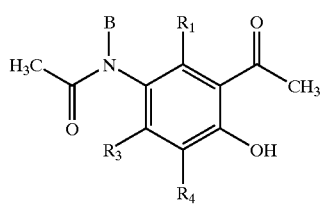

(7a)

wherein $R_1$, $R_3$, $R_4$, and B are defined as claim 1, the piperonal of formula (8a), and sodium hydroxide in the aqueous ethanol solution solvent, then thus obtained compound of formula (4b) is reacted with aqueous sodium hydroxide and hydrogen peroxide in methanol solvent to produce to a compound of formula (1e):

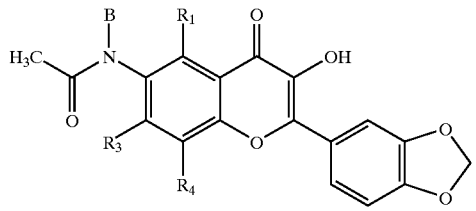

(1e)

wherein $R_1$, $R_3$, $R_4$ and B are defined in claim 1; or h) a compound of formula (9a):

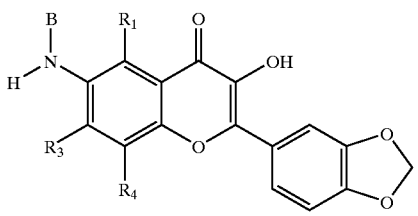

(9a)

wherein $R_1$, $R_1$, $R_4$ and B are defined as claim 1, is prepared by hydrolyzing the produced compound of formula (1e) with aqueous sulfuric acid solution in alcoholic solvent, then thus obtained compound of formula (9a) is reacted with a compound of formula (10)

 A—Y—X (10)

wherein A and Y are defined as claim 1 and X is a leaving group to produce a compound of formula (1hh):

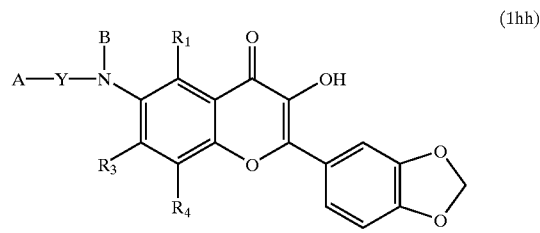

(1hh)

wherein $R_1$, $R_3$, $R_4$, A, Y and B are defined as claim 1; or i) the produced compound of formula (1hh) is reacted with boron tribromide (BBr$_3$) in methylenechloride solvent to produce a compound of formula (1i):

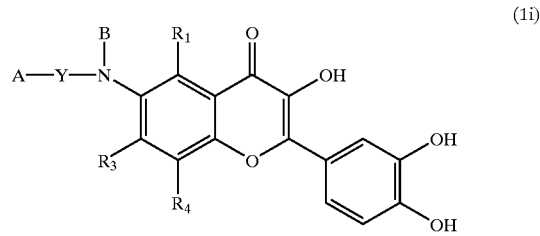

(1i)

wherein $R_1$, $R_3$, $R_4$, A, Y and B are defined as claim 1.

7. A composition for the treatment of cancer or neurodegenerative disease comprising the compound of formula (1), pharmaceutically acceptable salt, hydrate, solvate or isomer thereof as defined in claim 1 as an active ingredient with pharmaceutically acceptable carriers.

* * * * *